United States Patent
Yu et al.

(10) Patent No.: US 6,632,643 B2
(45) Date of Patent: Oct. 14, 2003

(54) USE OF α-1,4-GLUCAN LYASE FOR PREPARATION OF 1,5-D-HYDROFRUCTOSE

(75) Inventors: Shukun Yu, Malmo (SE); Kirsten Bojsen, Allerod (DK); Karsten Kragh, Viby J (DK); Maja Bojko, Gentofte (DK); John Nielsen, Copenhagen S (DK); Jan Marcussen, Copenhagen K (DK); Tove Christensen, Allerod (DK)

(73) Assignee: Danisco A/S, Copenhagen K (DK)

( * ) Notice: Subject to any disclaimer, the term of this patent is extended or adjusted under 35 U.S.C. 154(b) by 0 days.

(21) Appl. No.: 09/280,197

(22) Filed: Mar. 29, 1999

(65) Prior Publication Data

US 2002/0142403 A1 Oct. 3, 2002

Related U.S. Application Data

(63) Continuation of application No. 08/633,719, filed as application No. PCT/EP94/03397 on Oct. 15, 1994, now abandoned.

(30) Foreign Application Priority Data

| Oct. 15, 1993 | (GB) | ................................ | 932132 |
| Oct. 15, 1993 | (GB) | ................................ | 9321301 |
| Oct. 15, 1993 | (GB) | ................................ | 9321302 |
| Oct. 15, 1993 | (GB) | ................................ | 9321303 |
| Oct. 15, 1993 | (GB) | ................................ | 9321304 |
| Oct. 15, 1993 | (GB) | ................................ | 9321305 |

(51) Int. Cl.$^7$ .................. C12P 9/02; C12N 15/00; C12N 1/20; C12Q 1/68; C13K 5/00
(52) U.S. Cl. .................. 435/105; 435/320.1; 435/252.3; 435/6; 536/123.13
(58) Field of Search .................. 435/100, 320.1, 435/252.3, 6, 105; 536/123.13

(56) References Cited

FOREIGN PATENT DOCUMENTS

| EP | 0 177 477 | 4/1986 |
| FR | 2 617 502 | 1/1989 |
| WO | WO 94/09122 | 4/1994 |
| WO | 94/09122 | * 4/1994 |

OTHER PUBLICATIONS

Baute et al., Phytochemistry, 27, 3401–3403, Jun. 1988.*
Shukun Yu et al., *a–1,4–Glucan lyase, a new class of starch/glycogen degrading enzyme*, Biochimica et Biophysica Acta, vol. 1156, No. 3, 1993, pp. 313–320.
Shukun Yu et al., *a–1,4–Glucan lyase, a new class of starch/glycogen–degrading enzyme*, Planta, vol. 191, 1993, pp. 137–143.
Mme. M.A. Baute et al., *Bioconversions Fongiques Produisant, A Partir De Sucres, Des Composes Pyrontiques Inhabituels A Active Antibiotique*, Bull. Soc. Pharm. Bordeaux, vol. 128, 1989, pp. 9–18.

F. Sanger et al., *DNA sequencing with chain–terminating inhibitors*, Proc. Natl. Acad. Sci. USA, vol. 74, No. 12, Dec. 1977, pp. 5463–5467.
F.W. Lichtenthaler et al., *A Convenient Access To 1,5–Anhydroketoses*, Tetrahedron Letters, vol. 21, pp. 1429–1432.
Stephen L. Dellaporta et al., *A Plant DNA Minipreparation: Version II*, Plant Molecular Biology Reporter, vol. 1, No. 4, 1983, pp. 19–21.
Frank P. Buxton et al., *Transformation of Aspergillus niger using the argB gene of Aspergillus nidulans*, Gene, vol. 37, 1985, pp. 207–214.
David B. Collinge et al., *Gene expression in Brassica campestris showing a hypersensitive response to the incompatible pathogen Xanthomonas campestris pv. vitians*, Plant Molecular Biology, vol. 8, 1987, pp. 405–414.
Michael A. Frohman et al., *Rapid production of full–length cDNAs from rare transcripts: Amplification using a single gene–specific oligonucleotide primer*, Proc. Natl. Acad. Sci. USA, vol. 85, Dec. 1988, pp. 8998–9002.
Marie–Antoinette Baute et al., *Fungal Enzymic Activity Degrading 1,4–a–D–Glucans To 1,5–D–Anhydrofructose*, Phytochemistry, vol. 27, No. 11, 1988, pp. 3401–3403.
M. J. Daboussi et al., *Transformation of seven species of filamentous fungi using the nitrate reductase gene of aspergillus nidulans*, Current Genetics, vol. 15, 1989, pp. 453–456.
Peter J. Punt, *Intracellular and extracellular production in Aspergillus under the control of expression signals of the highly expressed Aspergillus nidulans gpdA gene*, Journal of Biotechnology, vol. 17, 1991, pp. 19–33.
Peter J. Punt et al., *Transformation of Filamentous Fungi Based on Hygromycin B and Phleomycin Resistance Markers*, Methods in Enzymology, vol. 216, 1992, pp. 447–457.
David B. Archer et al., *Proteolytic Degradation of Heterologous Proteins Expressed in Aspergillus Niger*, Biotechnology Letters, vol. 14, No. 5, May 1992, pp. 357–362.
Kevin Jorgensen et al., *Carotenoid scavenging of radicals*, Zeitschrift für Lebensmittel–Untersuchung und–Forschung, vol. 196, 1993, pp. 423–429.
Gary W. Saunders, *Gel Purification of Red Algal Genomic DNA: An Inexpensive and Rapid Method for the Isolation of Polymerase Chain Reaction–Friendly DNA*, J. Phycol., vol. 29, 1993, pp. 251–254.
Nancy LeGendre et al., *Gel Electrophoresis, Purification of Proteins and Peptides by SDS–Page*, pp. 74–101.

(List continued on next page.)

Primary Examiner—Maryam Monshipouri
(74) Attorney, Agent, or Firm—Nixon & Vanderhye, P.C.

(57) ABSTRACT

A method of preparing the sugar 1,5-D-anhydrofructose is described. The method comprises treating an α-1,4-glucan with an α-1,4-glucan lyase wherein the enzyme is used in substantially pure form. In a preferred embodiment, if the glucan contains links other than and in addition to the α-1,4-links, the α-1,4-glucan lyase is used in conjunction with a suitable reagent that can break the other links.

24 Claims, 26 Drawing Sheets

OTHER PUBLICATIONS

Martin L. Pall et al., *A series of six compact fungal transformation vectors containing polylinkers with multiple unique restriction sites*, Fungal Genetics Newsletter, No. 40, 1993, pp. 59–63.

Jane A. Langdale et al., *Cellular pattern of photosynthetic gene expression in developing maize leaves*, Genes & Development, vol. 2, 1988, pp. 106–115.

Curt M. Pueschel, *An Expanded Survey of the Ultrastructure of Red Algal Pit Plugs*, J. Phycol. vol. 25, 1989, pp. 625–636.

* cited by examiner

Calcoflour White stainings revealing fungi in upper part and lower part of Gracilaria lemnaeformis. (108x and 294x).

PAS / Anilinblue Black staining of Gracilaria lemnaeformis with fungi. The fungi have a significant higher content of carbohydrates.

The micrograph shows longitudinal and grazing sections of two thin-walled fungal hypha (f) growing between thick walls (w) of algal cells. Note thylacoid membranes in the algal chloroplast (arrows).

The antisense detections with clone 2 probe (upper row) are restricted to the fungi illustrated by the Calcoflour White staining of the succeding section (lower row). (46x and 108x).

Intense antisense detections with clone 2 probe are found over the fungi in Gracilaria lemnaeformis (294x).

```
MFSTLAFVAP  SALGASTFVG  AEVRSNVRIH  SAFPAVHTAT  RKTNRLNVSM
TALSDKQTAT  AGSTDNPDGI  DYKTYDYVGV  WGFSPLSNTN  WFAAGSSTPG
GITDWTATMN  VNFDRIDNPS  ITVQHPVQVQ  VTSYNNNSYR  VRFNPDGPIR
DVTRGPILKQ  QLDWIRTQEL  SEGCDPGMTF  TSEGFLTFET  KDLSVIIYGN
FKTRVTRKSD  GKVIMENDEV  GTASSGNKCR  GLMFVDRLYG  NAIASVNKNF
RNDAVKQEGF  YGAGEVNCKY  QDTYILERTG  IAMTNYNYDN  LNYNQWDLRP
PHHDGALNPD  YYIPMYYAAP  WLIVNGCAGT  SEQYSYGWFM  DNVSQSYMNT
GDTTWNSGQE  DLAYMGAQYG  PFDQHFVYGA  GGGMECVVTA  FSLLQGKEFE
NQVLNKRSVM  PPKYVFGFFQ  GVFGTSSLLR  AHMPAGENNI  SVEEIVEGYQ
NNNFPFEGLA  VDVDMQDNLR  VFTTKGEFWT  ANRVGTGGDP  NNRSVFEWAH
DKGLVCQTNI  TCFLRNDNEG  QDYEVNQTLR  ERQLYTKNDS  LTGTDFGMTD
DGPSDAYIGH  LDYGGGVECD  ALFPDWGRPD  VAEWWGNNYK  KLFSIGLDFV
WQDMTVPAMM  PHKIGDDINV  KPDGNWPNAD  DPSNGQYNWK  TYHPQVLVTD
MRYENHGREP  MVTQRNIHAY  TLCESTRKEG  IVENADTLTK  FRRSYIISRG
GYIGNQHFGG  MWVGDNSTTS  NYIQMMIANN  INMNMSCLPL  VGSDIGGFTS
YDNENQRTPC  TGDLMVRYVQ  AGCLLPWFRN  HYDRWIESKD  HGKDYQELYM
YPNEMDTLRK  FVEFRYRWQE  VLYTAMYQNA  AFGKPIIKAA  SMYNNDSNVR
RAQNDHFLLG  GHDGYRILCA  PVVWENSTER  ELYLPVLTQW  YKFGPDFDTK
PLEGAMNGGD  RIYNYPVPQS  ESPIFVREGA  ILPTRYTLNG  ENKSLNTYTD
EDPLVFEVFP  LGNNRADGMC  YLDDGVTTN   AEDNGKFSVV  KVAAEQDGGT
ETITFTNDCY  EYVFGGPFYV  RVRGAQSPSN  IHVSSGAGSQ  DMKVSSATSR
AALFNDGENG  DFWVDQETDS  LWLKLPNVVL  PDAVITIT
```

Fig. 8

```
GL1 - MFSTLAFVAPSALGASTFVGAEV-RSNVRIHSAFPAVHTATRKTNRLNVS       -49
      :. ::.::::::::: ::   . ::  . :::   :::   : ::.:::::::
GL2 - MYPTLTFVAPSALGARTFTCVGIFRSHILIHSVVPAVRLAVRKSNRLNVS       -50

GL1 - MTALSDKQTATAGSTDNPDGIDYKTYDYVGVWGFSPLSNTNWFAAGSSTP       -99
      :.::  :: :: ..:  :::: : : :::::  ::  : :::::::::::::
GL2 - MSALFDKPTAVTGGKDNPDNINYTTYDYVPVWRFDPLSNTNWFAAGSSTP       -100

GL1 - GGITDWTATMNVNFDRIDNPSITVQHPVQVQVTSYNNNSYRVRFNPDGPI       -149
      : :  ::::::::::::::::::  :.     :::::::::  :.:::::::::
GL2 - GDIDDWTATMNVNFDRIDNPSFTLEKPVQVQVTSYKNNCFRVRFNPDGPI       -150

GL1 - RDVTRGPILKQQLDWIRTQELSEGCDPGMTFTSEGFLTFETKDLSVIIYG       -199
      ::: :::::  ::: :::  ::  :  :: :  :: ::::   ::::::  :::::
GL2 - RDVDRGPILQQQLNWIRKQEQSKGFDPKMGFTKEGFLKFETKDLNVIIYG       -200

GL1 - NFKTRVTRKSDGKVIMENDEVGTASSGNKCRGLMFVDRLYGNAIASVNKN       -249
      :::::::::: :::  ::::  ::  :  .  :::::::::::::::: ::::::  :
GL2 - NFKTRVTRKRDGKGIMENNEVPAGSLGNKCRGLMFVDRLYGTAIASVNEN       -250

GL1 - FRNDAVKQEGFYGAGEVNCKYQDT------YILERTGIAMTNYNYDNLNY       -293
      .:::    . :::::::::::  . :.        ::::::::::::::::   ::
GL2 - YRNDPDRKEGFYGAGEVNCEFWDSEQNRNKYILERTGIAMTNYNYDNYNY       -300

GL1 - NQWDLRPPHHDGALNPDYYIPMYYAAPWLIVNGCAGTS-EQYSYGWFMDN       -342
      :: ::   :         :  .::::::::.::  :::  :  : :::::::::::
GL2 - NQSDLIAP--GYPSDPNFYIPMYFAAPWVVVKGCSGNSDEQYSYGWFMDN       -348

GL1 - VSQSYMNTGDTTWNSGQEDLAYMGAQYGPFDQHFVYGAGGGMECVVTAFS       -392
      :::.:::::: :..:: : :  ::::::::: :::::::::::::   : : ..:  :: :::
GL2 - VSQTYMNTGGTSWNCGEENLAYMGAQCGPFDQHFVYGDGDGLEDVVQAFS       -398

GL1 - LLQGKEFENQVLNKRSVMPPKYVFGFFQGVFGTSSLLRAHMPAGENNISV       -442
      :::::::::::::::::::::::.::::::::::::::::::::.....     : :  : :::::
GL2 - LLQGKEFENQVLNKRAVMPPKYVFGYFQGVFGIASLLREQRPEGGNNISV       -448

GL1 - EEIVEGYQNNNFPFEGLAVDVDMQDNLRVFTTKGEFWTANRVGTGGDPNN       -492
      :::::::  ::::   ::::::::::  :::::::  :::::::::::::.:::::  ::
GL2 - QEIVEGYQSNNFPLEGLAVDVDMQQDLRVFTTKIEFWTANKVGTGGDSNN       -498

GL1 - RSVFEWAHDKGLVCQTNITCFLRNDNEGQDYEVNQTLRERQLYTKNDSLT       -542
      .::::::::::::::::::.:::::::::::::.::::::.: ::::::::::::
GL2 - KSVFEWAHDKGLVCQTNVTCFLRNDNGGADYEVNQTLREKGLYTKNDSLT       -548

GL1 - GTDFGMTDDGPSDAYIGHLDYGGGVECDALFPDWGRPDVAEWWGNNYKKL       -592
      :   ::  :   ::::::::::::::::  ::::::::::::::::   :::   :: ::
GL2 - NTNFGTTNDGPSDAYIGHLDYGGGGNCDALFPDWGRPGVAEWWGDNYSKL       -598
```

Fig. 9A

```
GL1    - FSIGLDFVWQDMTVPAMMPHKIGDDINVKPDGNWPNADDPSNGQYNWKTY  -642
         ::::::::::::::::::::::..  .    :::    :::::   :::::.:
GL2    - FKIGLDFVWQDMTVPAMMPHKVGDAVDTRSPYGWPNENDPSNGRYNWKSY  -648

GL1    - HPQVLVTDMRYENHGREPMVTQRNIHAYTLCESTRKEGIVENADTLTKFR  -692
         ::::::::::::::::::::::: :::::.:::::::::::: :::::::::
GL2    - HPQVLVTDMRYENHGREPMFTQRNMHAYTLCESTRKEGIVANADTLTKFR  -698

GL1    - RSYIISRGGYIGNQHFGGMWVGDNSTTSNYIQMMIANNINMNMSCLPLVG  -742
         :::::::::::::::::::::::::::..  :.:::::. .:::::::::::
GL2    - RSYIISRGGYIGNQHFGGMWVGDNSSSQRYLQMMIANIVNMNMSCLPLVG  -748

GL1    - SDIGGFTSYDNENQRTPCTGDLMVRYVQAGCLLPWFRNHYDRWIESKDHG  -792
         ::::::::::       :   : ::::::..::::::::::::   :  .: :     :
GL2    - SDIGGFTSYDG---RNVCPGDLMVRFVQAGCLLPWFRNHYGRLVEGKQEG  -795

GL1    - KDYQELYMYPNEMDTLRKFVEFRYRWQEVLYTAMYQNAAFGKPIIKAASM  -842
         :   :::::::   ::   :::::.::::::::::::::::::::::::::::
GL2    - KYYQELYMYKDEMATLRKFIEFRYRWQEVLYTAMYQNAAFGKPIIKAASM  -845

GL1    - YNNDSNVRRAQNDHFLLGGHDGYRILCAPVVWENSTERELYLPVLTQWYK  -892
         :  ::  :::   ::  ::::::::::::::::::::::.: :.::::::::  :::
GL2    - YDNDRNVRGAQDDHFLLGGHDGYRILCAPVVWENTTSRDLYLPVLTKWYK  -895

GL1    - FGPDFDTKPLEGAMNGGDRIYNYPVPQSESPIFVREGAILPTRYTLNGEN  -942
         ::::.:::   :.    :.   ::    :   : ::    ::::.:::::::::::::  : :
GL2    - FGPDYDTKRLDSALDGGQMIKNYSVPQSDSPIFVREGAILPTRYTLDGSN  -945

GL1    - KSLNTYTDEDPLVFEVFPLGNNRADGMCYLDDGGVTTNAEDNGKFSVVKV  -992
         ::.:::::   ::::::::::::::::::::::::::::: :::  ::::::. :
GL2    - KSMNTYTDKDPLVFEVFPLGNNRADGMCYLDDGGITTDAEDHGKFSVINV  -995

GL1    - AAEQDGGTETITFTNDCYEYVFGGPFYVRVRGAQSPSNIHVSSGAGSQDM  -1042
         :   :  ::  :.  :   :::   :::::::::.    .   :   :::::::  ::
GL2    - EALRKGVTTTIKFAYDTYQYVFDGPFYVRIRNLTTASKINVSSGAGEEDM  -1045

GL1    - KVSSATSRAALFNDGENGDFWVDQETDSLWLKLPNVVLPDAVITIT  -1088
         .::  :::::::::  ::   :...  :...   :::::::::::..:  :::::::
GL2    - TPTSANSRAALFSDGGVGEYWADNDTSSLWMKLPNLVLQDAVITIT  -1091
```

Fig. 9B

Microphotograph of a fungal hypha (f) growing between algal cell walls (w). Note grains of floridean starch (s) and thylakoids (arrows) in the algal cell. Bar = 2 μm.

```
              10         20         30         40         50         60
               |          |          |          |          |          |
   1  AGACAGGTGC GTTTTTGTTT ATTCTATTCT GTGCGGCAGA TATGCACTCA CAAGAAACAA
  61  ATTGTACAAA TATTTCTAAT TACAGTTGTA GGTGCAGTTG AAAATCCGGT CGCACAAAGA
 121  TCATTGATGC ACAAAGATGA TAACGCCTGA TTAGTACTCA AGGTTTAATT GGGTATGTGT
 181  GCGACCTCTC TTTGGCTAGC ATTACCTGAT TGGTTACAAC TGCAAATACT GCGGCAGCAA
 241  TGAGGAATGA AGTCAGCATC GATAGCTCGG CCTCATAAAA ATTGATTTCA ATTTTATATT
 301  CCCAGTTTTA ATCTCGAATC CTATATAATG GCCATCGTTC CCTCCTCGCC TCTTCATTCT
 361  CCTCCATCAC TCCAGCTCAG TCATCCCTCA ACTTGGCCTC CTCTGATATC TTCCGAACAA
 421  AACATCTTGT CCAATCTTTT TTTGAGCTAG ATCTCATTAT ACCTCCGTCA TGGCAGGATT
 481  TTCTGATCCT CTCAACTTTT GCAAAGCAGA AGACTACTAC AGTGTTGCGC TAGACTGGAA
 541  GGGCCCTCAA AAAATCATTG GAGTAGACAC TACTCCTCCA AAGAGCACCA AGTTCCCCAA
 601  AAACTGGCAT GGAGTGAACT TGAGATTCGA TGATGGGACT TTAGGTGTGG TTCAGTTCAT
 661  TAGGCCGTGC GTTTGGAGGG TTAGATACGA CCCTGGTTTC AAGACCTCTG ACGAGTATGG
 721  TGATGAGAAT ACGTGAGTTA CCCCATATGT CATTATTGGT AGCGAAAAAC ATATGCTAAT
 781  CAACTAACGA GGCATATAGG AGGACAATTG TGCAAGATTA TATGAGTACT CTGAGTAATA
 841  AATTGGATAC TTATAGAGGT CTTACGTGGG AAACCAAGTG TGAGGATTCG GGAGATTTCT
 901  TTACCTTCTC AGTAAGTGCC AGTACTGCTA TAGCTCCGCT ATATATATAA CACCACTAAC
 961  TAACTGCCCT AAATAGTCCA AGGTCACCGC CGTTGAAAAA TCCGAGCGGA CCCGCAACAA
1021  GGTCGGCGAT GGCCTCAGAA TTCACCTATG GAAAAGCCCT TTCCGCATCC AAGTAGTGCG
1081  CACCTTGACC CCTTTGAAGG ATCCTTACCC CATTCCAAAT GTAGCCGCAG CCGAAGCCCG
1141  TGTGTCCGAC AAGGTCGTTT GGCAAACGTC TCCCAAGACA TTCAGAAAGA ACCTGCATCC
1201  GCAACACAAG ATGCTAAAGG ATACAGTTCT TGACATTGTC AAACCTGGAC ATGGCGAGTA
1261  TGTGGGGTGG GGAGAGATGG GAGGTATCCA GTTTATGAAG GAGCCAACAT TCATGAACTA
1321  TTTTAGTAAG CCCCGAAGAG GTTCCTTATA AATTCTTGGT GGTCATTTTT ACTAACCCAG
1381  TGTAGACTTC GACAATATGC AATACCAGCA AGTCTATGCC CAAGGTGCTC TCGATTCTCG
1441  CGAGCCACTG TAAGTACCGT CCTGTGGCAC GACTTAACCC AATAACTAAT CTTTCAACAA
1501  GGTACCACTC GGATCCCTTC TATCTTGATG TGAACTCCAA CCCGGAGCAC AAGAATATCA
1561  CGGCAACCTT TATCGATAAC TACTCTCAAA TTGCCATCGA CTTTGGAAAG ACCAACTCAG
```

Fig. 14A

```
1621 GCTACATCAA GCTGGGAACC AGGTATGGTG GTATCGATTG TTACGGTATC AGTGCGGATA
1681 CGGTCCCGGA AATTGTACGA CTTTATACAG GTCTTGTTGG ACGTTCAAAG TTGAAGCCCA
1741 GATATATTCT CGGGGCCCAT CAAGCCTGTA AGTCCTTCCC CTCATGAGTG ATTTATCAGA
1801 CTTGCATAAT AAACTAACCT CGTTTTCAAA GGTTATGGAT ACCAACAGGA AAGTGACTTG
1861 TATTCTGTGG TCCAGCAGTA CCGTGACTGT AAATTTCCAC TTGACGGGAT TCACGTCGAT
1921 GTCGATGTTC AGGTAAATGG CCATGGTATC ATTGAAGCTT TGAGAAATGT TCTAACTGTG
1981 TTTATAACAT TCCTAGGACG GCTTCAGAAC TTTCACCACC AACCCACACA CTTTCCCTAA
2041 CCCCAAAGAG ATGTTTACTA ACTTGAGGAA TAATGGAATC AAGTGCTCCA CCAATATCAC
2101 TCCTGTTATC AGCATTAACA ACAGAGAGGG TGGATACAGT ACCCTCCTTG AGGGAGTTGA
2161 CAAAAAATAC TTTATCATGG ACGACAGATA TACCGAGGGA ACAAGTGGGA ATGCGAAGGA
2221 TGTTCGGTAC ATGTACTACG GTGGTGGTAA TAAGGTTGAG GTCGATCCTA ATGATGTTAA
2281 TGGTCGGCCA GACTTTAAAG ACAACTAGTA AGTTGTTTAT TTGACTACGA TAGGTAACCC
2341 GTAAGCGGCA TTAACATATT TGTAGTGACT TCCCCGCGAA CTTCAACAGC AAACAATACC
2401 CCTATCATGG TGGTGTGAGC TACGGTTATG GGAACGGTAG TGTAAGTGAC GATATCTCAC
2461 CAACATAATG AAATTTATAA GGACTAACTA GACACAAAAA TTTGTAGGCA GGTTTTTACC
2521 CGGACCTCAA CAGAAAGGAG GTTCGTATCT GGTGGGGAAT GCAGTACAAG TATCTCTTCG
2581 ATATGGGACT GGAATTTGTG TGGCAAGACA TGACTACCCC AGCAATCCAC ACATCATATG
2641 GAGACATGAA AGGGTTGCCC ACCCGTCTAC TCGTCACCTC AGACTCCGTC ACCAATGCCT
2701 CTGAGAAAAA GCTCGCAATT GAAACTTGGG CTCTCTACTC CTACAATCTC ACAAAGCAA
2761 CTTGGCATGG TCTTAGTCGT CTCGAATCTC GTAAGAACAA ACGAAACTTC ATCCTCGGGC
2821 GTGGAAGTTA TGCCGGAGCC TATCGTTTTG CTGGTCTCTG GACTGGGGAT AATGCAAGTA
2881 ACTGGGAATT CTGGAAGATA TCGGTCTCTC AAGTTCTTTC TCTGGGCCTC AATGGTGTGT
2941 GCATCGCGGG GTCTGATACG GGTGGTTTTG AACCCTACCG TGATGCAAAT GGGGTCGAGG
3001 AGAAATACTG TAGCCCAGAG CTACTCATCA GGTGGTATAC TGGTTCATTC CTCTTGCCGT
3061 GGCTCAGGAA CCATTATGTC AAAAAGGACA GGAAATGGTT CCAGGTAATC TATCCTTTCT
3121 TATCTTTGAA GCATTGAAGA TACTAAGATA TAATCTAGGA ACCATACTCG TACCCCAAGC
3181 ATCTTGAAAC CCATCCAGAA CTCGCAGACC AAGCATGGCT CTATAAATCC GTTTTGGAGA
```

Fig. 14B

3241 TCTGTAGGTA CTATGTGGAG CTTAGATACT CCCTCATCCA ACTACTTTAC GACTGCATGT
3301 TTCAAAACGT AGTCGACGGT ATGCCAATCA CCAGATCTAT GGTATGTATT CTACCCTAGG
3361 CTTCCAGAGC AACATATGCT AACCAATTGA ACCTGGGTTT CTAGCTCTTG ACCGATACTG
3421 AGGATACCAC CTTCTTCAAC GAGAGCCAAA AGTTCCTCGA CAACCAATAT ATGGCTGGTG
3481 ACGACATTCT TGTTGCACCC ATCCTCCACA GTCGCAAAGA AATTCCAGGC GAAAACAGAG
3541 ATGTCTATCT CCCTCTTTAC CACACCTGGT ACCCCTCAAA TTTGAGACCA TGGGACGATC
3601 AAGGAGTCGC TTTGGGGAAT CCTGTCGAAG GTGGTAGTGT CATCAATTAT ACTGCTAGGA
3661 TTGTTGCACC CGAGGATTAT AATCTCTTCC ACAGCGTGGT ACCAGTCTAC GTTAGAGAGG
3721 GTAAGCAGTA AAATAATCTC TTCCCAGTTT CAAATACATT TAGCTAGTAG CTAACGCTAT
3781 GAACCTACAG GTGCCATCAT CCCGCAAATC GAAGTACGCC AATGGACTGG CCAGGGGGGA
3841 GCCAACCGCA TCAAGTTCAA CATCTACCCT GGAAAGGATA AGGTAAAATT CAATGATCAC
3901 CCTGCATCTA TTCCATCGCT GGTTTTCTTT ACCCTTACTG ACTTCATTCC TCAAAATACA
3961 GGAGTACTGT ACCTATCTTG ATGATGGTGT TAGCCGTGAT AGTGCGCCGG AAGACCTCCC
4021 ACAGTACAAA GAGACCCACG AACAGTCGAA GGTTGAAGGC GCGGAAATCG CAAAGCAGAT
4081 TGGAAAGAAG ACGGGTTACA ACATCTCAGG AACCGACCCA GAAGCAAAGG GTTATCACCG
4141 CAAAGTTGCT GTCACACAAG TAATACCGCC CTTGACTTGT ATCACTTCCT GACATCATGC
4201 TAATATTTCT CTGTTTACCT CAAAGACGTC AAAAGACAAG ACGCGTACTG TCACTATTGA
4261 GCCAAAACAC AATGGATACG ACCCTTCCAA AGAGGTGGGT GATTATTATA CCATCATTCT
4321 TTGGTACGCA CCAGGTTTCG ATGGCAGCAT CGTCGATGTG AGCAAGACGA CTGTGAATGT
4381 TGAGGGTGGG GTGGAGCACC AAGTTTATAA GAACTCCGAT TTACATACGG TTGTTATCGA
4441 CGTGAAGGAG GTGATCGGTA CCACAAAGAG CGTCAAGATC ACATGTACTG CCGCTTAAGG
4501 TCTTTTCTTG GGGGCGGGAG GCGAGACCTT CGAAATGTAT ACGGGAGTGG TAACTCCGGG
4561 AAAATGGTGA TATGGGGGAT CAAGTTGGAG GGGAATCTGT TTATTTCTTT ATTTCTTTAT
4621 TTACTGGATT GGAAAATAGG GAGCACAGTT CTGACTGGAT TGGTTTGATT GTTGGCCTCT
4681 ACGGGTTCTC TTTACTTTGT CTGGAAATCC AATTTATTGT TATGCG

Fig. 14C

```
                   10         20         30         40         50         60
                    |          |          |          |          |          |
   1 ATGCAGGCAA CGACAGGCGT TTTTTGTTTT ATCCGCAGAG GTGCAGCAGC AGGAAACAAA
  61 CCATACAAAC ATTCCTTGAC GCGGTTTTAG GTGCAGTTAA GGCCCGGGCG CACCAAGAAC
 121 ATTGATGTAC TTGGTCTAAA AAAGATCATA ATACCCGATT AGTGTTCATG GTTTGATTGG
 181 GTCTAAGTAC AAGTTTTACA GAGTTCAGCT TAGTTCATTG TTCGAAACTA CCAATATCAC
 241 ACCTATGCCT GCTGGCATTG ATAGCTCGGC TTGTGAAAGC TGATTACAAT CTTACATTTC
 301 TGATTTAATA TCGGACTGAT CTATATATAA GGGTCATCAT TTCCTCTCCG CCTTTTGGTT
 361 CTCTTTCATC ACCCCAGCCC AATCATCACC GTTGGCCTTT ACTTCTCTCT TCCGTTGATA
 421 TTTTCTCGAC AAAACATCTT GTCCACTGTT AGGCTAGCTC CAGAATTAT  CCCTCCAACA
 481 TGGCAGGATT ATCCGACCCT CTCAATTTCT GCAAAGCAGA GGACTACTAC GCTGCTGCCA
 541 AAGGCTGGAG TGGCCCTCAG AAGATCATTC GCTATGACCA GACCCCTCCT CAGGGTACAA
 601 AAGATCCGAA AAGCTGGCAT GCGGTAAACC TTCCTTTCGA TGACGGGACT ATGTGTGTAG
 661 TGCAATTCGT CAGACCCTGT GTTTGGAGGG TTAGATATGA CCCCAGTGTC AAGACTTCTG
 721 ATGAGTACGG CGATGAGAAT ACGTGGGTCG CCCAGTCAAT TAACTATGCC GCTAGTGATT
 781 ATGGAAAGCT TCTGCTAACC GATCAATGAG GCATGTAGGA GGACTATTGT ACAAGACTAC
 841 ATGACTACTC TGGTTGGAAA CTTGGACATT TTCAGAGGTC TTACGTGGGT TTCTACGTTG
 901 GAGGATTCGG GCGAGTACTA CACCTTCAAG GCAAGCCTCA GTGTTATATC TCGAATATAT
 961 TATATATCAC AACAAACTAA CTAGTCATAC AGTCCGAAGT CACTGCCGTG GACGAAACCG
1021 AACGGACTCG AAACAAGGTC GGCGACGGCC TCAAGATTTA CCTATGGAAA AATCCCTTTC
1081 GCATCCAGGT AGTGCGTCTC TTGACCCCCC TGGTGGACCC TTTCCCCATT CCCAACGTAG
1141 CCAATGCCAC AGCCCGTGTG GCCGACAAGG TTGTTTGGCA GACGTCCCCG AAGACGTTCA
1201 GGAAAAACTT GCATCCGCAG CATAAGATGT TGAAGGATAC AGTTCTTGAT ATTATCAAGC
1261 CGGGGCACGG AGAGTATGTG GGTTGGGGAG AGATGGGAGG CATCGAGTTT ATGAAGGAGC
1321 CAACATTCAT GAATTATTTC AGTAAGCTCT TGAAAGATTT CCTATCTCTT GACGGTCGTT
1381 TTTGCTAAGG AAACTGTAGA CTTTGACAAT ATGCAATATC AGCAGGTCTA TGCACAAGGC
1441 GCTCTTGATA GTCGTGAGCC GTTGTAAGTA ACGTCCTGTG ACATGTCATG ATTACAGTAA
1501 CTGATCGTTC AATAAGGTAT CACTCTGATC CCTTCTATCT CGACGTGAAC TCCAACCCAG
```

Fig. 15A

1561 AGCACAAGAA CATTACGGCA ACCTTTATCG ATAACTACTC TCAGATTGCC ATCGACTTTG
1621 GGAAGACCAA CTCAGGCTAC ATCAAGCTGG GTACCAGGTA TGGCGGTATC GATTGTTACG
1681 GTATCAGCGC GGATACGGTC CCGGAGATTG TGCGACTTTA TACTGGACTT GTTGGGCGTT
1741 CGAAGTTGAA GCCCAGGTAT ATTCTCGGAG CCCACCAAGC TTGTAAGCCC GCCCCTTTA
1801 CGATGCATTT ATTAGGGGTC CACAGACTAA ACTTGTTCCA AAGGTTATGG ATACCAGCAG
1861 GAAAGTGACT TGCATGCTGT TGTTCAGCAG TACCGTGACA CCAAGTTTCC GCTTGATGGG
1921 TTGCATGTCG ATGTCGACTT TCAGGTAAAT GGCCCAGGTA TCGTTGAAGC TTTGGAGAAT
1981 GCTAATTGTG CTCGTAAAAC TTTAAGGACA ATTTCAGAAC GTTTACCACT AACCCGATTA
2041 CGTTCCCTAA TCCCAAAGAA ATGTTTACCA ATCTAAGGAA CAATGGAATC AAGTGTTCCA
2101 CCAACATCAC CCCTGTTATC AGTATCAGAG ATCGCCCGAA TGGGTACAGT ACCCTCAATG
2161 AGGGATATGA TAAAAAGTAC TTCATCATGG ATGACAGATA TACCGAGGGG ACAAGTGGGG
2221 ACCCGCAAAA TGTTCGATAC TCTTTTTACG GCGGTGGGAA CCCGGTTGAG GTTAACCCTA
2281 ATGATGTTTG GGCTCGGCCA GACTTTGGAG ACAATTAGTA AGTTACTCAA TAGGCTACTT
2341 GAGATATTCT GTAGGTGGCA TTAACACGAC TATAGTGACT TCCCTACGAA CTTCAACTGC
2401 AAAGACTACC CCTATCATGG TGGTGTGAGT TACGGATATG GAATGGCAC TGTAAGTGAT
2461 AATAAGTCAT AAATACAACG TAATTCATGG AGACTAATCA GTGGTAAATG AATTTTAGCC
2521 AGGTTACTAC CCTGACCTTA ACAGAGAGGA GGTTCGTATC TGGTGGGAT TGCAGTACGA
2581 GTATCTCTTC AATATGGGAC TAGAGTTTGT ATGGCAAGAT ATGACAACCC CAGCGATCCA
2641 TTCATCATAT GGAGACATGA AAGGGTTGCC CACCCGTCTG CTCGTCACCG CCGACTCAGT
2701 TACCAATGCC TCTGAGAAAA AGCTCGCAAT TGAAAGTTGG GCTCTTTACT CCTACAACCT
2761 CCATAAAGCA ACCTTCCACG GTCTTGGTCG TCTTGAGTCT CGTAAGAACA AACGTAACTT
2821 CATCCTCGGA CGTGGTAGTT ACGCCGGTGC CTATCGTTTT GCTGGTCTCT GGACTGGAGA
2881 TAACGCAAGT ACGTGGGAAT CTGGAAGAT TTCGGTCTCC CAAGTTCTTT CTCTAGGTCT
2941 CAATGGTGTG TGTATAGCGG GGTCTGATAC GGGTGGTTTT GAGCCCGCAC GTACTGAGAT
3001 TGGGGAGGAG AAATATTGCA GTCCGGAGCT ACTCATCAGG TGGTATACTG GATCATTCCT
3061 TTTGCCATGG CTTAGAAACC ACTACGTCAA GAAGGACAGG AAATGGTTCC AGGTAATATA

Fig. 15B

```
3121 CTCTTTCTGG TCTCTGAGTA TCGAAGACGC TAAGACAATA TAGGAACCAT ACGCGTACCC
3181 CAAGCATCTT GAAACCCATC CAGAGCTCGC AGATCAAGCA TGGCTTTACA AATCTGTTCT
3241 AGAAATTTGC AGATACTGGG TAGAGCTAAG ATATTCCCTC ATCCAGCTCC TTTACGACTG
3301 CATGTTCCAA AACGTGGTCG ATGGTATGCC ACTTGCCAGA TCTATGGTAT GCATTTTATC
3361 CGTCTCCTTT CACGATAATG CACCAGTCTA ACCGAATTTT CTTTTAGCTC TTGACCGATA
3421 CTGAGGATAC GACCTTCTTC AATGAGAGCC AAAAGTTCCT CGATAACCAA TATATGGCTG
3481 GTGACGACAT CCTTGTAGCA CCCATCCTCC ACAGCCGTAA CGAGGTTCCG GGAGAGAACA
3541 GAGATGTCTA TCTCCCTCTA TTCCACACCT GGTACCCCTC AAACTTGAGA CCGTGGGACG
3601 ATCAGGGAGT CGCTTTAGGG AATCCTGTCG AAGGTGGCAG CGTTATCAAC TACACTGCCA
3661 GGATTGTTGC CCCAGAGGAT TATAATCTCT TCCACAACGT GGTGCCGGTC TACATCAGAG
3721 AGGGTAAGCG ATGGAATAAT TTCTTGCAAG TTCCAGATAC AAGTGGTTAC TGACACCTTA
3781 AACCAGGTGC CATCATTCCG CAAATTCAGG TACGCCAGTG GATTGGCGAA GGAGGGCCTA
3841 ATCCCATCAA GTTCAATATC TACCCTGGAA AGGACAAGGT ATATTCTCCA TGACTATCGC
3901 GCATTTATTC TTTCTCTACT CGCACTAACT TCATCTGAAT ATAGGAGTAT GTGACGTACC
3961 TTGATGATGG TGTTAGCCGC GATAGTGCAC CAGATGACCT CCCGCAGTAC CGCGAGGCCT
4021 ATGAGCAAGC GAAGGTCGAA GGCAAAGACG TCCAGAAGCA ACTTGCGGTC ATTCAAGGGA
4081 ATAAGACTAA TGACTTCTCC GCCTCCGGGA TTGATAAGGA GGCAAAGGGT TATCACCGCA
4141 AAGTTTCTAT CAAACAGGTA CATGATTTCA TCTTCCTTTT TTCGCAGTCA CTATTATATC
4201 ATCCTAACAT TGCTTCTCTT ATTTAAAAGG AGTCAAAAGA CAAGACCCGT ACTGTCACCA
4261 TTGAGCCAAA ACACAACGGA TACGACCCCT CTAAGGAAGT TGGTAATTAT TATACCATCA
4321 TTCTTTGGTA CGCACCGGGC TTTGACGGCA GCATCGTCGA TGTGAGCCAG GCGACCGTGA
4381 ACATCGAGGG CGGGGTGGAA TGCGAAATTT TCAAGAACAC CGGCTTGCAT ACGGTTGTAG
4441 TCAACGTGAA AGAGGTGATC GGTACCACAA AGTCCGTCAA GATCACTTGC ACTACCGCTT
4501 AGAGCTCTTT TATGAGGGGT ATATGGGAGT GGCAGCTCAG AAATTTGGGA AGCTTCTGGG
4561 TATTCCTTTT GTTTATTTAC TTATTTATTG AATCGACCAA TACGGGTGGG ATTCTCTCTG
4621 GTTTTGTGA GGCTATGTTT TACTTGGTCT GAAAATCAAA TTCGTTCTCA
```

```
MC  - MAGFSDPLNFCKAEDYYSVALDWKGPQKIIGVDTTPPKSTKFPKNWHGVN  -50
      ::: ::::::::::::::. :   :  ::::::   : :::   :: ::   :: ::
MV  - MAGLSDPLNFCKAEDYYAAAKGWSGPQKIIRYDQTPPQGTKDPKSWHAVN  -50

MC  - LRFDDGTLGVVQFIRPCVWRVRYDPGFKTSDEYGDENTRTIVQDYMSTLS  -100
      :  ::::::. ::::.:::::::::::    ::::::::::::::::..::
MV  - LPFDDGTMCVVQFVRPCVWRVRYDPSVKTSDEYGDENTRTIVQDYMTTLV  -100

MC  - NKLDTYRGLTWETKCEDSGDFFTFSSKVTAVEKSERTRNKVGDGLRIHLW  -150
      ::  .:::::  .        ::::...::  :   ::::.  .:::::::::.: ::
MV  - GNLDIFRGLTWVSTLEDSGEYYTFKSEVTAVDETERTRNKVGDGLKIYLW  -150

MC  - KSPFRIQVVRTLTPLKDPYPIPNVAAAEARVSDKVVWQTSPKTFRKNLHP  -200
      :  ::::::::  ::::   ::.:::::::    :    :::.:::::::::
MV  - KNPFRIQVVRLLTPLVDPFPIPNVANATARVADKVVWQTSPKTFRKNLHP  -200

MC  - QHKMLKDTVLDIVKPGHGEYVGWGEMGGIQFMKEPTFMNYFNFDNMQYQQ  -250
      ::::::::::::::.::::::::::::::::: :::::::::::::::::::
MV  - QHKMLKDTVLDIIKPGHGEYVGWGEMGGIEFMKEPTFMNYFNFDNMQYQQ  -250

MC  - VYAQGALDSREPLYHSDPFYLDVNSNPEHKNITATFIDNYSQIAIDFGKT  -300
      :::::::::::::::::::::::::::::::::::::::::::::::::
MV  - VYAQGALDSREPLYHSDPFYLDVNSNPEHKNITATFIDNYSQIAIDFGKT  -300

MC  - NSGYIKLGTRYGGIDCYGISADTVPEIVRLYTGLVGRSKLKPRYILGAHQ  -350
      :::::::::::::::::::::::::::::::::::::::::::::::::
MV  - NSGYIKLGTRYGGIDCYGISADTVPEIVRLYTGLVGRSKLKPRYILGAHQ  -350

MC  - ACYGYQQESDLYSVVQQYRDCKFPLDGIHVDVDVQDGFRTFTTNPHTFPN  -400
      ::::::::::  .:::::: :::::.::: :::::: ::::::: ::::
MV  - ACYGYQQESDLHAVVQQYRDTKFPLDGLHVDVDFQDNFRTFTTNPITFPN  -400

MC  - PKEMFTNLRNNGIKCSTNITPVISINNREGGYSTLLEGVDKKYFIMDDRY  -450
      :::::::::::::::::::::::::: :     ::::: ::  :::::::::
MV  - PKEMFTNLRNNGIKCSTNITPVISIRDRPNGYSTLNEGYDKKYFIMDDRY  -450

MC  - TEGTSGNAKDVRYMYYGGGNKVEVDPNDVNGRPDFKDNYDFPANFNSKQY  -500
      ::::::    :::  .:::: :::  ::::    ::::   :::::::::.:::  :  :
MV  - TEGTSGDPQNVRYSFYGGGNPVEVNPNDVWARPDFGDNYDFPTNFNCKDY  -500

MC  - PYHGGVSYGYGNGSAGFYPDLNRKEVRIWWGMQYKYLFDMGLEFVWQDMT  -550
      ::::::::::::::. :..::::::::::::.:   :::  :::::::::::::
MV  - PYHGGVSYGYGNGTPGYYPDLNREEVRIWWGLQYEYLFNMGLEFVWQDMT  -550

MC  - TPAIHTSYGDMKGLPTRLLVTSDSVTNASEKKLAIETWALYSYNLHKATW  -600
      ::::: .:::::::::::::::::. ::::::::::::::::.:::::::::::::.
MV  - TPAIHSSYGDMKGLPTRLLVTADSVTNASEKKLAIESWALYSYNLHKATF  -600
```

Fig. 16B

```
MC  - HGLSRLESRKNKRNFILGRGSYAGAYRFAGLWTGDNASNWEFWKISVSQV   -650
      :::  :::::::::::::::::::::::::::::::::: ::::::::::
MV  - HGLGRLESRKNKRNFILGRGSYAGAYRFAGLWTGDNASTWEFWKISVSQV   -650

MC  - LSLGLNGVCIAGSDTGGFEPYRDANGVEEKYCSPELLIRWYTGSFLLPWL   -700
      ::::::::::::::::::: : .    ::::::::::::::::::::::
MV  - LSLGLNGVCIAGSDTGGFEPAR-TEIGEEKYCSPELLIRWYTGSFLLPWL   -699

MC  - RNHYVKKDRKWFQEPYSYPKHLETHPELADQAWLYKSVLEICRYYVELRY   -750
      :::::::::::::::::.:::::::::::::::::::::::: :::::
MV  - RNHYVKKDRKWFQEPYAYPKHLETHPELADQAWLYKSVLEICRYWVELRY   -749

MC  - SLIQLLYDCMFQNVVDGMPITRSMLLTDTEDTTFFNESQKFLDNQYMAGD   -800
      :::::::::::::::::::. .::::::::::::::::::::::::::::
MV  - SLIQLLYDCMFQNVVDGMPLARSMLLTDTEDTTFFNESQKFLDNQYMAGD   -799

MC  - DILVAPILHSRKEIPGENRDVYLPLYHTWYPSNLRPWDDQGVALGNPVEG   -850
      :::::::::: :.:::::::::::::.:::::::::::::::::::::::
MV  - DILVAPILHSRNEVPGENRDVYLPLFHTWYPSNLRPWDDQGVALGNPVEG   -849

MC  - GSVINYTARIVAPEDYNLFHSVVPVYVREGAIIPQIEVRQWTGQGGANRI   -900
      :::::::::::::::::::: :::::.:::::::: :::::: : :: :
MV  - GSVINYTARIVAPEDYNLFHNVVPVYIREGAIIPQIQVRQWIGEGGPNPI   -899

MC  - KFNIYPGKDKEYCTYLDDGVSRDSAPEDLPQYKETHEQSKVEGAEIAKQI   -950
      ::::::::::: .:::::::::::::..:::::. .::..:::: . ::.
MV  - KFNIYPGKDKEYVTYLDDGVSRDSAPDDLPQYREAYEQAKVEGKDVQKQL   -949

MC  - G-----KKTGYNISGTDPEAKGYHRKVAVTQTSKDKTRTVTIEPKHNGYD   -995
      :    . :: : :::::.. : ::::::::::::::::::::::
MV  - AVIQGNKTNDFSASGIDKEAKGYHRKVSIKQESKDKTRTVTIEPKHNGYD   -999

MC  - PSKEVGDYYTIILWYAPGFDGSIVDVSKTTVNVEGGVEHQVYKNSDLHTV   -1045
      ::::::. ::::::::::::::: .:::: :. ::::: ..:. .::::
MV  - PSKEVGNYYTIILWYAPGFDGSIVDVSQATVNIEGGVECEIFKNTGLHTV   -1049

MC  - VIDVKEVIGTTKSVKITCTAA   -1066
      :. :::::::::::::::::.:
MV  - VVNVKEVIGTTKSVKITCTTA   -1070
```

| | | | | |
|---|---|---|---|---|
| MAGFSDPLNF | CKAEDYYSVA | LDWKGPQKII | GVDTTPPKST | KFPKNWHGVN |
| LRFDDGTLGV | VQFIRPCVWR | VRYDPGFKTS | DEYGDENTRT | IVQDYMSTLS |
| NKLDTYRGLT | WETKCEDSGD | FFTFSSKVTA | VEKSERTRNK | VGDGLRIHLW |
| KSPFRIQVVR | TLTPLKDPYP | IPNVAAAEAR | VSDKVVWQTS | PKTFRKNLHP |
| QHKMLKDTVL | DIVKPGHGEY | VGWGEMGGIQ | FMKEPTFMNY | FNFDNMQYQQ |
| VYAQGALDSR | EPLYHSDPFY | LDVNSNPEHK | NITATFIDNY | SQIAIDFGKT |
| NSGYIKLGTR | YGGIDCYGIS | ADTVPEIVRL | YTGLVGRSKL | KPRYILGAHQ |
| ACYGYQQESD | LYSVVQQYRD | CKFPLDGIHV | DVDVQDGFRT | FTTNPHTFPN |
| PKEMFTNLRN | NGIKCSTNIT | PVISINNREG | GYSTLLEGVD | KKYFIMDDRY |
| TEGTSGNAKD | VRYMYYGGGN | KVEVDPNDVN | GRPDFKDNYD | FPANFNSKQY |
| PYHGGVSYGY | GNGSAGFYPD | LNRKEVRIWW | GMQYKYLFDM | GLEFVWQDMT |
| TPAIHTSYGD | MKGLPTRLLV | TSDSVTNASE | KKLAIETWAL | YSYNLHKATW |
| HGLSRLESRK | NKRNFILGRG | SYAGAYRFAG | LWTGDNASNW | EFWKISVSQV |
| LSLGLNGVCI | AGSDTGGFEP | YRDANGVEEK | YCSPELLIRW | YTGSFLLPWL |
| RNHYVKKDRK | WFQEPYSYPK | HLETHPELAD | QAWLYKSVLE | ICRYYVELRY |
| SLIQLLYDCM | FQNVVDGMPI | TRSMLLTDTE | DTTFFNESQK | FLDNQYMAGD |
| DILVAPILHS | RKEIPGENRD | VYLPLYHTWY | PSNLRPWDDQ | GVALGNPVEG |
| GSVINYTARI | VAPEDYNLFH | SVVPVYVREG | AIIPQIEVRQ | WTGQGGANRI |
| KFNIYPGKDK | EYCTYLDDGV | SRDSAPEDLP | QYKETHEQSK | VEGAEIAKQI |
| GKKTGYNISG | TDPEAKGYHR | KVAVTQTSKD | KTRTVTIEPK | HNGYDPSKEV |
| GDYYTIILWY | APGFDGSIVD | VSKTTVNVEG | GVEHQVYKNS | DLHTVVIDVK |
| EVIGTTKSVK | ITCTAA | | | |

Fig. 17

| | | | | |
|---|---|---|---|---|
| MAGLSDPLNF | RKAEDYYAAA | KGWSGPQKII | RYDQTPPQGT | KDPKSWHAVN |
| LPFDDGTMCV | VQFVRPCVWR | VRYDPSVKTS | DEYGDENTRT | IVQDYMTTLV |
| GNLDIFRGLT | WVSTLEDSGE | YYTFKSEVTA | VDETERTRNK | VGDGLKIYLW |
| KNPFRIQVVR | LLTPLVDPFP | IPNVANATAR | VADKVVWQTS | PKTFRKNLHP |
| QHKMLKDTVL | DIIKPGHGEY | VGWGEMGGIE | FMKEPTFMNY | FNFDNMQYQQ |
| VYAQGALDSR | EPLYHSDPFY | LDVNSNPEHK | NITATFIDNY | SQIAIDFGKT |
| NSGYIKLGTR | YGGIDCYGIS | ADTVPEIVRL | YTGLVGRSKL | KPRYILGAHQ |
| ACYGYQQESD | LHAVVQQYRD | TKFPLDGLHV | DVDFQDNFRT | FTTNPITFPN |
| PKEMFTNLRN | NGIKCSTNIT | PVISIRDRPN | GYSTLNEGYD | KKYFIMDDRY |
| TEGTSGDPQN | VRYSFYGGGN | PVEVNPNDVW | ARPDFGDNYD | FPTNFNCKDY |
| PYHGGVSYGY | GNGTPGYYPD | LNREEVRIWW | GLQYEYLFNM | GLEFVWQDMT |
| TPAIHSSYGD | MKGLPTRLLV | TADSVTNASE | KKLAIESWAL | YSYNLHKATF |
| HGLGRLESRK | NKRNFILGRG | SYAGAYRFAG | LWTGDNASTW | EFWKISVSQV |
| LSLGLNGVCI | AGSDTGGFEP | ARTEIGEEKY | CSPELLIRWY | TGSFLLPWLR |
| NHYVKKDRKW | FQEPYAYPKH | LETHPELADQ | AWLYKSVLEI | CRYWVELRYS |
| LIQLLYDCMF | QNVVDGMPLA | RSMLLTDTED | TTFFNESQKF | LDNQYMAGDD |
| ILVAPILHSR | NEVPGENRDV | YLPLFHTWYP | SNLRPWDDQG | VALGNPVEGG |
| SVINYTARIV | APEDYNLFHN | VVPVYIREGA | IIPQIQVRQW | IGEGGPNPIK |
| FNIYPGKDKE | YVTYLDDGVS | RDSAPDDLPQ | YREAYEQAKV | EGKDVQKQLA |
| VIQGNKTNDF | SASGIDKEAK | GYHRKVSIKQ | ESKDKTRTVT | IEPKHNGYDP |
| SKEVGNYYTI | ILWYAPGFDG | SIVDVSQATV | NIEGGVECEI | FKNTGLHTVV |
| VNVKEVIGTT | KSVKITCTTA | | | |

Fig. 18

USE OF α-1,4-GLUCAN LYASE FOR PREPARATION OF 1,5-D-HYDROFRUCTOSE

RELATED APPLICATIONS

This application is a Continuation Application of application ser. No. 08/633719 now abandoned filed Jul. 8, 1996, which is the U.S. national phase under 35 U.S.C. §371 of International Application No. PCT/EP94/03397, filed Oct. 15, 1994, which claims the benefit of priority under 35 U.S.C. §119 to Application No. 9321304.9, filed Oct. 15, 1993 in Great Britain, Application No. 9321305.6, filed Oct. 15, 1993 in Great Britain, Application No. 9321301.5, filed Oct. 15, 1993 in Great Britain, Application No. 9321302.5, filed Oct. 15, 1993 in Great Britain, and Application No. 9321303.1, filed Oct. 15, 1993, in Great Britain.

The present invention also relates to the use of an enzyme, in particular α-1,4-glucan lyase ("GL"), to prepare 1,5-D-anhydrofructose ("AF") from substrates based on α-1,4-glucan.

The present invention also relates to the use of a sugar, in particular 1,5-D-anhydrofructose ("AF"), as an anti-oxidant, in particular as an anti-oxidant for food stuffs and beverages.

The present invention relates to the use of 1,5-D-anhydrofructose ("AF") as a sweetener, in particular as a sweetener for foodstuffs and beverages, preferably human foodstuffs and beverages.

FR-A-2617502 and Baute et al in Phytochemistry [1988] vol. 27 No. 11 pp3401–3403 report on the production of AF in *Morchella vulgaris* by an apparent enzymatic reaction. The yield of production of AF is quite low. Despite a reference to a possible enzymatic reaction, neither of these two documents presents any amino acid sequence data for any enzyme let alone any nucleotide sequence information. These documents say that AF can be a precursor for the preparation of the antibiotic pyrone microthecin.

Yu et al in Biochimica et Biophysica Acta [1993] vol 1156 pp313–320 report on the preparation of GL from red seaweed and its use to degrade α-1,4-glucan to produce AF. The yield of production of AF is quite low. Despite a reference to the enzyme GL this document does not present any amino acid sequence data for that enzyme let alone any nucleotide sequence information coding for the same. This document also suggests that the source of GL is just algal.

A typical α-1,4-glucan based substrate is starch. Today, starches have found wide uses in industry mainly because they are cheap raw materials.

Starch degrading enzymes can be grouped into various categories. The starch hydrolases produce glucose or glucose-oligomers. A second group of starch degrading enzymes are phosphorylases that produce glucose-1-phosphate from starch in the presence of inorganic phosphate.

AF has also been chemically synthesised—see the work of Lichtenthaler in Tetrahedron Letters Vol 21 pp 1429–1432. However, this chemical synthesis involves a large number of steps and does not yield large quantities of AF.

The chemical synthetic route for producing AF is therefore very expensive.

There is therefore a need for a process that can prepare AF in a cheap and easy manner and also in a way that enables large quantities of AF to be made.

Furthermore, anti-oxidants are typically used to prevent oxygen having any deleterious effect on a substance such as a foodstuff. Two commonly used anti-oxidants are GRINDOX 142 and GRINDOX 1029. These anti-oxidants contain many components and are quite expensive to make.

There is therefore a need to have a simpler and cheaper form of anti-oxidant.

Furthermore, sweeteners are often used in the preparation of foodstuffs and beverages. However, many sweeteners are expensive and complex to prepare.

There is therefore a need to have a simpler and cheaper form of sweetener.

According to the present invention there is provided a method of preparing the sugar 1,5-D-anhydrofructose comprising treating an α-1,4-glucan with the enzyme α-1,4-glucan lyase characterised in that enzyme is used in substantially pure form.

Preferably if the glucan contains links other than and in addition to the α-1,4-links the α-1,4-glucan lyase is used in conjunction with a suitable reagent that can break the other links—such as a hydrolase—preferably glucanohydrolase.

Preferably the glucan is starch or a starch fraction prepared chemically or enzymatically. If prepared enzymatically the reaction can be performed before the addition of the α-1,4-glucan lyase or the reactions can be performed simultaneously. The suitable reagent can be an auxiliary enzyme. Preferred auxiliary enzymes are alpha- or beta-amylases. Preferably a debranching enzyme is used. More preferably the auxiliary enzyme is at least one of pullanase or isoamylase.

Preferably the α-1,4-glucan lyase either is bound to a support or, more preferably, is in a dissolved form.

Preferably the enzyme is isolated from either a fungus, preferably *Morchella costata* or *Morchella vulgaris,* or from a fungally infected algae, preferably *Gracilariopsis lemaneiformis,* or from algae lone, preferably *Gracilariopsis lemaneiformis.*

Preferably the enzyme is isolated and/or further purified from the fungus or from the fungally infected algae or algae alone using a gel that is not degraded by the enzyme.

Preferably the gel is based on dextrin or derivatives thereof.

Preferably the gel is a cyclodextrin—more preferably beta-cyclodextrin. Preferably the enzyme comprises the amino acid sequence SEQ. I.D. No. 1. or the amino acid sequence SEQ. I.D. No. 2 or the amino acid sequence SEQ. ID. No. 5 or the amino acid SEQ. I.D. No. 6, or any variant thereof.

In an alternative preferable embodiment, the enzyme comprises any one of the amino acid sequences shown in SEQ. I.D. No.s 9–11, or any variant thereof.

The term "any variant thereof" means any substitution of, variation of, modification of, replacement of, deletion of or addition of an amino acid from or to the sequence providing the resultant enzyme has lyase activity.

Preferably the enzyme is used in combination with amylopectin or dextrin.

Preferably, the enzyme is obtained from the expression of a nucleotide sequence coding for the enzyme.

Preferably the nucleotide sequence is a DNA sequence.

Preferably the DNA sequence comprises a sequence that is the same as, or is complementary to, or has substantial homology with, or contains any suitable codon substitutions for any of those of, SEQ. ID. No. 3 or SEQ. ID. No. 4 or SEQ. ID. No. 7 or SEQ. ID. No. 8.

In an alternative preferable embodiment, the DNA sequence comprises any one of the sequences that are the same as, or are complementary to, or have substantial homology with, or contain any suitable codon substitutions as shown as SEQ. ID. No.s 12–14.

The expression "substantial homology" covers homology with respect to structure and/or nucleotide components and/or biological activity.

The expression "contains any suitable codon substitutions" covers any codon replacement or substitution with another codon coding for the same amino acid or any addition or removal thereof providing the resultant enzyme has lyase activity.

In other words, the present invention also covers a modified DNA sequence in which at least one nucleotide has been deleted, substituted or modified or in which at least one additional nucleotide has been inserted so as to encode a polypeptide having the activity of a glucan lyase, preferably having an increased lyase activity.

Preferably the starch is used in high concentration—such as up to about 25% solution.

Preferably the substrate is treated with the enzyme in the presence of a buffer.

More preferably the substrate is treated with the enzyme in the presence of substantially pure water.

Preferably the substrate is treated with the enzyme in the absence of a co-factor.

According to the present invention there is also provided a method of preparing the sugar 1,5-D-anhydrofructose comprising treating an α-1,4-glucan with the enzyme α-1,4-glucan lyase characterised in that enzyme comprises the amino acid sequence SEQ. ID. No. 1. or the amino acid sequence SEQ. ID. No. 2 or the amino acid sequence SEQ. ID. No. 5. or the amino acid sequence SEQ. ID. No. 6, or any one of the amino acid sequences SEQ. I.D. No.s 9–11, or any variant thereof.

According to the present invention there is also provided the sugar 1,5-D-anhydrofructose when prepared by the method of the present invention.

AF prepared by the present method was confirmed and characterised by $^{13}$C NMR.

One of key advantages of the present method is that the sugar 1,5-D-anhydrofructose can be prepared in much larger quantities than before and by a method that is relatively easier and cheaper than the known processes. For example the sugar can now be prepared in amounts of for example greater than 100 g—such as 500 g—compared to the prior art methods when only much smaller amounts were and could be produced—such as micro gram amounts.

Typical reactions that can be catalyzed by GL can be summarised as follows:

1). Amylopectin→AF+limit dextrin
2). Amylose→AF+limit dextrin
3). Dextrin→AF+glucose In reaction 1), the ratio of the two products depend on the structure of amylopectin or the distribution of α-1,6glucosidic linkages in the amylopectin molecules.

In reaction 2) and 3), the ratio of the products depends on the degree of polymerisation (DP) number of the substrate. In reaction 3 the ratio between AF and glucose depends upon the DP. For example if the dextrin contains 10 glucose units the ratio AF:glucose would be 9:1.

Another advantage of the present invention is that glucans that contain links other than α1,4-links can be substantially degraded—whereas before only partial degradation was achieved. The substantial degradation of the 1,5-D-anhydrofructose precursor is one of the factors leading to the increased yields of 1,5-D-anhydrofructose.

Other advantages are AF is a naturally occurring substance and therefore it has a potential for human purposes. For example, it can be converted to the antibiotic microthecin by AF dehydrase. Antibiotics are known for their uses in food bio-preservation, which is an important area in food technology. However, to date, the preparation of AF and also microthecin has had a number of disadvantages. For example, only small quantities could be produced. Also, the process was costly.

The present invention overcomes these problems by providing a larger production of and much cheaper production of AF and so also other products such as microthecin. In this regard, it is possible to prepare gram to kilogram amounts of AF.

A further advantage is that the lyase is stable for at least one year at 4° C. and can be lyophilized without loss of activity.

Another advantage is that the lyase produces AF directly from starches and does not need the presence of any co-factors.

Another advantage is that the enzyme can be used in pure water. This result is very surprising.

Based on the simple properties of the present lyase, one can expect that the production cost of AF will be comparable to that of glucose. This is especially advantageous that the present lyase does not necessarily require the presence of any co-factors which are generally very expensive.

In general α-1,4-glucans can be used as substrate for the enzyme.

As a preferred substrate, starch is used.

In a preferred process, soluble or gelatinized starch or starch hydrolysate are used. The starch hydrolysates can be prepared either chemically or enzymatically.

If an enzyme is used for the partial starch degradation the enzyme can either be added before the addition of the lyase or any other additional starch degrading reagent (such as the enzyme glucanohydrolase) which may be added simultaneously.

The lyase will convert the glucan to AF. The enzyme will attach the substrate from the non reducing end and leave only the reducing sugar unconverted. The residual glucose can be removed by known methods some of which have been described here.

Using the reaction described here pure AF can be produced and also in large amounts.

In one embodiment, the α-1,4-glucan lyase is purified from the fungally infected algae—such as *Gracilariopsis lemaneiformis*—by affinity chromatography on β-cyclodextrin Sepharose, ion exchange chromatography on Mono Q HR 5/5 and gel filtration on Superose 12 columns. The purified enzyme produces 1,5-anhydro-D-fructose from α-1,4-glucans.

The fungal lyase isolated from fungal infected *Gracilariopsis lemaneiformis* is characterized as having a pH optimum at 3.5–7.5 when amylopectin is used, a temperature optimum at 50° C. and a pI of 3.9.

In another embodiment, the α-1,4-glucan lyase is purified from the fungus *Morchella costata* by affinity chromatography on β-cyclodextrin Sepharose, ion exchange chromatography on Mono Q HR 55 and gel filtration on Superose 12 columns. The purified enzyme produces 1,5-anhydro-D-fructose from α-1,4-glucans.

The fungal lyase shows a pI around 5.4 as determined by isoelectric focusing on gels with pH gradient of 3 to 9. The molecular weight determined by SDS-PAGE on 8–25% gradient gels was 110 kDa. The enzyme exhibited a pH optimum in the range pH 5–7. The temperature optimum was found to be between 30–45° C.

In another embodiment, the α-1,4-glucan lyase is purified from the fungus *Morchella vulgaris* by affinity chromatography on β-cyclodextrin Sepharose, ion exchange chromatography on Mono Q HR 5/5 and gel filtration on Superose 12 columns. The purified enzyme produces 1,5-anhydro-D-fructose from α-1,4-glucans.

In another embodiment, the α-1,4-glucan lyase is purified from algae—such as *Gracilariopsis lemaneiformis*—by affinity chromatography on β-cyclodextrin Sepharose, ion exchange chromatography on Mono Q HR 5/5 and gel filtration on Superose 12 columns. The purified enzyme produces 1,5-anhydro-D-fructose from α-1,4-glucans.

Typical pH and temperature optima for the lyase catalyzed reaction for some of the GL enzymes according to the present invention are as follows:

| GL sources | Optimal pH | Optimal pH range | Optimal temperature |
|---|---|---|---|
| M. costata | 6.5 | 5.5–7.5 | 37 C.; 40 C.[a] |
| M. vulgaris | 6.4 | 5.9–7.6 | 43 C.; 48 C.[a] |
| Fungal infected *Gracilariopsis lemaneiformis* | 3.8 | 3.7–4.1 | 40 C.; 45 C.[a] |

[a]Parameters determined using glycogen as substrate; other parameters determined using amylopectin as substrate.

The enzymes of the present invention convert amylose and amylopectin to 1,5-anhydrofructose.

Among the maltosaccharides tested, we found that the lyase showed low activity towards maltose, and lower activity to maltotriose and maltoheptaose with the highest activity to maltotetraose and maltopentaose. The enzyme showed no substrate inhibition up to a concentration 10 mg $ml^{-1}$ among these maltosaccharides.

The enzymes from each of the preferred sources has been sequenced and the amino acid sequences are presented later. Also presented later are the DNA sequences coding for the enzymes.

The present invention therefore describes a new starch degrading enzyme—namely a new α-1,4-glucan lyase. This is an enzyme that has been purified and characterized for the first time.

As mentioned above, the present invention also relates to some specific uses of AF.

In particular, the present invention relates to the use of 1,5-D-anhydrofructose ("AF"), as an anti-oxidant, in particular as an anti-oxidant for food stuffs and beverages.

Therefore according to the present invention there is provided the use of 1,5-D-anhydrofructose (AF) as an antioxidant.

Preferably AF is or is used in an edible substance.

Preferably AP is used in or as a foodstuff or beverage.

Preferably, AF is used in combination with another anti-oxidant.

Preferably the AF is prepared by the method according to the present invention.

The main advantages of using AF as an anti-oxidant are that it is a natural product, it is non-metabolisable, it is easy to manufacture, it is water-soluble, and it is generally non-toxic.

In a preferred embodiment the present invention therefore relates to the enzymatic preparation of pure AF which can be used as an attractive water soluble antioxidant for food and non-food purposes. In the application examples are given for the use of AF as an antioxidant in food formulations.

In the accompanying examples it is seen that AF is comparable with known high quality commercial available food antioxidants. Non-food examples include use in polymer chemistry as oxygen scavengers during the synthesis of polymers. Also, AF could be used for the synthesis of bio-degradable plastic.

Experiments have shown that AF can be an efficient reducing agent (antioxidant), as it can easily reduce 3,5-dinitrosalicylic acid to 3-amino-5-nitrosalicylic acid.

AF is a naturally occurring substance and therefore it has a tremendous potential for use as an acceptable antioxidant. AF can also be converted into the antibiotic microthecin by AF dehydrase. Antibiotics are known for their uses in food biopreservation, an important area in food biotechnology.

In another aspect, the present invention also relates to the use of 1,5-D-anhydrofructose as a sweetener, in particular as a sweetener for foodstuffs and beverages, preferably human foodstuffs and beverages.

Thus according to this aspect of the present invention there is provided the use of 1,5-D-anhydrofructose as a sweetener.

Preferably the AF is used as or in a human foodstuff or beverage.

The AF may be used in any desired amount such as a 5% solution or 100 mg/kg to 500 mg/kg.

The advantages of using AF as a sweetener are that it is a natural product, it is generally non-toxic, it is water soluble, it is non-metabolisable and it is easy to manufacture.

The present invention therefore also relates to a novel application of AF as a sweetener.

Preferably the AF is prepared by the method according to the present invention.

Further aspects of the present invention include:

a method of preparing the enzyme α-1,4-glucan lyase (GL) comprising isolating the enzyme from a fungally infected algae, fungus or algae alone;

an enzyme comprising the amino acid sequence SEQ. ID. No. 1. or SEQ. ID. No. 2 or SEQ. ID. No. 5. or SEQ. ID. No. 6, or any variant thereof;

an enzyme comprising the amino acid sequence SEQ. ID. No. 9. or SEQ. ID. No. 10 or SEQ. ID. No. 11, or any variant thereof;

a nucleotide sequence coding for the enzyme α-1,4-glucan lyase, preferably wherein the sequence is not in its natural environment (i.e. it does not form part of the natural genome of a cellular organism capable of expressing the enzyme, preferably wherein the nucleotide sequence is a DNA sequence;

a nucleotide sequence wherein the DNA sequence comprises at least a sequence that is the same as, or is complementary to, or has substantial homology with, or contains any suitable codon substitutions for any of those of, SEQ. ID. No. 3 or SEQ. ID. No. 4 or SEQ. ID. No. 7 or SEQ. ID. No. 8, preferably wherein the sequence is in isolated form;

a nucleotide sequence wherein the DNA sequence comprises at least a sequence that is the same as, or is complementary to, or has substantial homology with, or contains any suitable codon substitutions for any of those of, SEQ. ID. No. 12 or SEQ. ID. No. 13 or SEQ. ID. No. 14, preferably wherein the sequence is in isolated form; and the use of beta-cyclodextrin to purify an enzyme, preferably GL.

Other preferred embodiments of the present invention include any one of the following: A transformed host organism having the capability of producing AF as a consequence of the introduction of a DNA sequence as herein described; such a transformed host organism which is a microorganism—preferably wherein the host organism is selected from the group consisting of bacteria, moulds, fungi and yeast; preferably the host organism is selected from the group consisting of Saccharomyces, Kluyveromyces, Aspergillus, Trichoderma Hansenula, Pichia, Bacillus Streptomyces, Eschericia such as *Aspergillus oryzae, Saccharomyces cerevisiae, bacillus sublilis, Bacillus amyloliquefascien, Eschericia coli.*; A method for preparing the sugar 1,5-D-anhydrofructose comprising the use of a transformed host organism expressing a nucleotide sequence encoding the enzyme α-1,4-glucan lyase, preferably wherein the nucleotide sequence is a DNA sequence, preferably wherein the DNA sequence is one of the sequences hereinbefore described; A vector incorporating a nucleotide sequence as hereinbefore described, preferably wherein the vector is a replication vector, preferably wherein the vector is an expression vector containing the nucleotide sequence downstream from a promoter sequence, preferably the vector includes a marker (such as a resistance marker); Cellular organisms, or cell line, transformed with such a vector; A method of producing the product α-1,4-glucan lyase or any nucleotide sequence or part thereof coding for same, which comprises culturing such an organism (or cells from a cell line) transfected with such a vector and recovering the product.

In particular, in the expression systems, the enzyme should preferably be secreted to ease its purification. To do so the DNA encoding the mature enzyme is fused to a signal sequence, a promoter and a terminator from the chosen host.

For expression in *Aspergillus niger* the gpdA (from the Glyceraldehyde-3-phosphate dehydrogenase gene of *Aspergillus nidulans*) promoter and signal sequence is fused to the 5' end of the DNA encoding the mature lyase. The terminator sequence from the *A. niger* trpC gene is placed 3' to the gene (Punt, P. J. et al 1991—(1991): 3. Biotech. 17, 19–34). This construction is inserted into a vector containing a replication origin and selection origin for *E. coli* and a selection marker for *A. niger*. Examples of selection markers for *A. niger* are the amdS gene, the argB gene, the pyrG gene, the hygB gene, the BmlR gene which all have been used for selection of transformants. This plasmid can be transformed into *A. niger* and the mature lyase can be recovered from the culture medium of the transformants. Eventually the construction could be transformed into a protease deficient strain to reduce the proteolytic degradation of the lyase in the culture medium (Archer D. B. et al 992—Biotechnol. Lett. 14, 357–362).

Instead of *Aspergillus niger* as host, other industrial important microorganisms for which good expression systems are known could be used such as:*Aspergillus oryzae,* Aspergillus sp., Trichoderma sp., *Saccharomyces cerevisiae,* Kluyveromyces sp., Hansenula sp., Pichia sp., *Bacillus subtilis, B. amyloliquefaciens,* Bacillus sp., Streptomyces sp. or *E. coli.*

The following samples were deposited in accordance with the Budapest Treaty at the recognised depositary The National Collections of Industrial and Marine Bacteria Limited (NCIMB) at 23 St. Machar Drive, Aberdeen, Scotland, United Kingdom, AB21 RY on Jun 20, 1994:

E. *Coli* containing plasmid pGL1 (NCIMB 40652)—[ref. DH5alpha-pGL1]; and

E. *Coli* containing plasmid pGL2 (NCIMB 40653)—[ref. DH5alpha-pGL2].

The following sample was accepted as a deposit in accordance with the Budapest Treaty at the recognised depositary The Culture Collection of Algae and Protozoa (CCAP) at Dunstaffnage Marine Laboratory PO Box 3, Oban, Argyll, Scotland, United Kingdom, PA34 4AD on Oct. 11, 1994:

Fungally infected *Gracilariopsis lemaneiformis* (CCAP 1373/1)—[ref. GLQ-1 (Qingdao)].

Thus highly preferred embodiments of the present invention include a GL enzyme obtainable from the expression of the GL coding sequences present in plasmids that are the subject of either deposit NCIMB 40652 or deposit NCIMB 40653; and a GL enzyme obtainable from the fungally infected algae that is the subject of deposit CCAP 1373/1.

The following samples were deposited in accordance with the Budapest Treaty at the recognised depositary The National Collections of Industrial and Marine Bacteria Limited (NCIMB) at 23 St. Machar Drive, Aberdeen, Scotland, United Kingdom, AB2 1 RY on Oct. 3, 1994:

E. *Coli* containing plasmid pMC (NCIMB 40687)—[ref. DH5alpha-pMC];

E. *Coli* containing plasmid pMV1 (NCIMB 40688)—[ref. DH5alpha-pMV1]; and.

E. *Coli* containing plasmid pMV2 (NCIMB 40689)—[ref. DH15alpha-pMV2].

Plasmid pMC is a pBluescript II KS containing a 4.1 kb fragment isolated from a genomic library constructed from *Morchella costata.* The fragment contains a gene coding for α-1,4-glucan lyase.

Plasmid pMV1 is a pBluescript II KS containing a 2.45 kb fragment isolated from a genomic library constructed from *Morchella vulgaris.* The fragment contains the 5' end of a gene coding for α-1,4-glucan lyase.

Plasmid MV2 is a pPUC19 containing a 3.1 kb fragment isolated from a genomic library constructed from *Morchella vulgaris.* The fragment contains the 3' end of a gene coding for α-1,4-glucan lyase.

In the following discussions, MC represents *Morchella costata* and MV represents *Morchella vulgaris.*

As mentioned, the GL coding sequence from *Morchella vulgaris* was contained in two plasmids. With reference to FIG. 15 pMV1 contains the nucleotides from position 454 to position 2902; and pMV2 contains the nucleotides downstream from (and including) position 2897. With reference to FIGS. 12 and 13, to ligate the coding sequences one can digest pMV2 with restriction enzymes EcoRI and BamHI and then insert the relevant fragment into pMV1 digested with restriction enzymes EcoRI and Thus highly preferred embodiments of the present invention include a GL enzyme obtainable from the expression of the GL coding sequences present in plasmids that are the subject of either deposit NCIMB 40687 or deposit NCIMB 40688 and deposit NCIMB 40689.

The following sample was also accepted as a deposit in accordance with the Budapest Treaty at the recognised depositary The Culture Collection of Algae and Protozoa (CCAP) at Dunstaffnage Marine Laboratory PO Box 3, Oban, Argyll, Scotland, United Kingdom, PA34 4AD on Oct. 11, 1994:

Fungally infected *Gracilariopsis lemaneiformis* (CCAP 1373/2)—[ref. GLSC-1 (California)].

Thus a highly preferred embodiment of the present invention includes a GL enzyme obtainable from the algae that is the subject of deposit CCAP 1373/2.

The present invention will now be described only by way of example.

In the following Examples reference is made to the accompanying figures in which:

FIG. 1 shows stained fungally infected algae;
FIG. 2 shows stained fungally infected algae;
FIG. 3 shows sections of fungal hypha;
FIG. 4 shows sections of fungally infected algae;
FIG. 5 shows a section of fungally infected algae;
FIG. 6 shows a plasmid map of pGL1;
FIG. 7 shows a plasmid map of pGL2;
FIG. 8 shows the amino acid sequence represented as SEQ. I.D. No.3 showing positions of the peptide fragments that were sequenced;
FIGS. 9A and 9B show the alignment of SEQ. I.D. No. 1 with SEQ. I.D. No.2;
FIG. 11 shows a plasmid map of pMC;
FIG. 12 shows a plasmid map of pMV1;
FIG. 13 shows a plasmid map of pMV2;
FIGS. 14A, 14B and 14C show the GL coding sequence and part of the 5' and 3' non-translated regions for genomic DNA obtained from *Morchella costata;*
FIGS. 15A, 15B and 15C show the GL coding sequence and part of the 5' and 3' non-translated regions for genomic DNA obtained from *Morchella vulgaris;*
FIGS. 16A and 16B show a comparison of the GL coding sequences and non-translated regions from *Morchella costata* and *Morchella vulgaris;*
FIG. 17 shows the amino acid sequence represented as SEQ. I.D. No. 5 showing positions of the peptide fragments that were sequenced;
FIG. 18 shows the amino acid sequence represented as SEQ. I.D. No. 6 showing positions of the peptide fragments that were sequenced;
FIG. 19 shows a graph of oxygen consumption with and without the presence of AF; and
FIG. 20 shows a TLC plate.

In more detail, FIG. 1 shows Calcoflour White stainings revealing fungi in upper part and lower part of *Gracilariopsis lemaneiformis* (108×and 294×).

FIG. 9 shows the alignment of SEQ. I.D. No. 1 (GL1) with SEQ. I.D. No.2 (GL2). The total number of residues for GL1 is 1088; and the total number of residues for GL2 is 1091. In making the comparison, a structure-genetic matrix was used (Open gap cost: 10; Unit gap cost: 2). In FIG. 9 the character to show that two aligned residues are identical is ':'; and the character to show that two aligned residues are similar is '.'. Amino acids said to be 'similar' are: A,S,T; D,E; N,Q; R,K; I,L,M,V; F,Y,W. Overall there is an identity of 845 amino acids (i.e. 77.67%); a similarity of 60 amino acids (5.51%). The number of gaps inserted in GL1 are 3 and the number of gaps inserted in GL2 are 2.

Figure 10:
Figure 11:
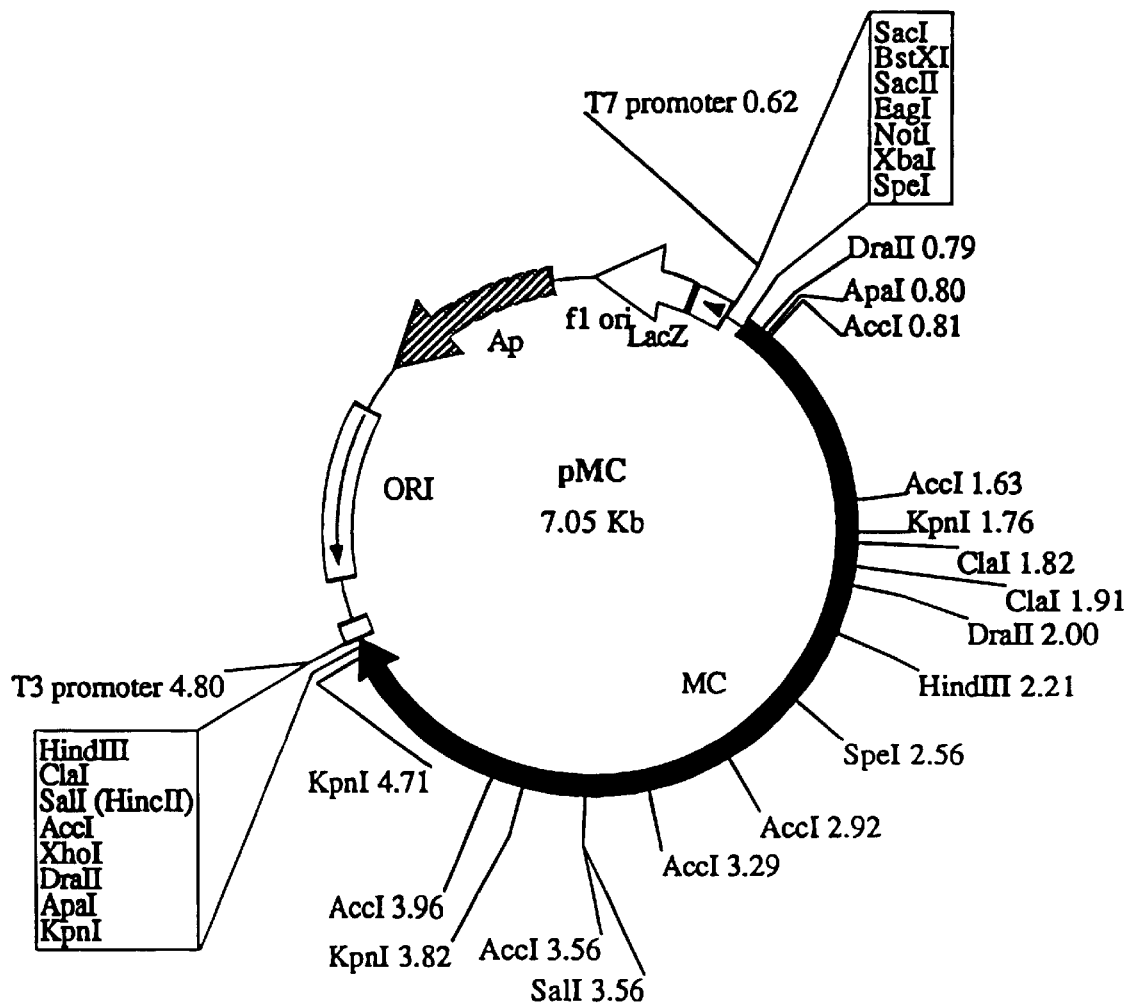
Figure 12:
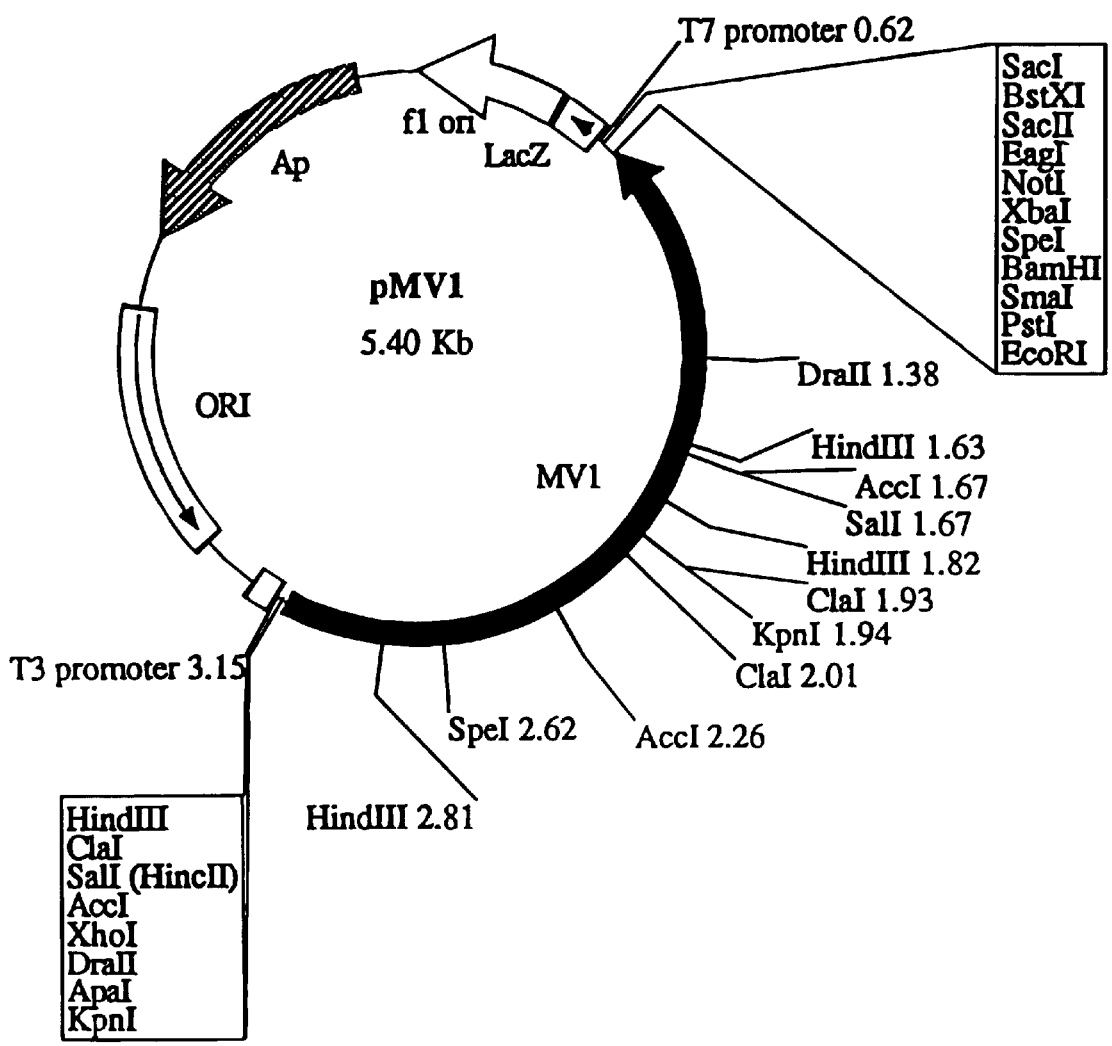
Figure 13:
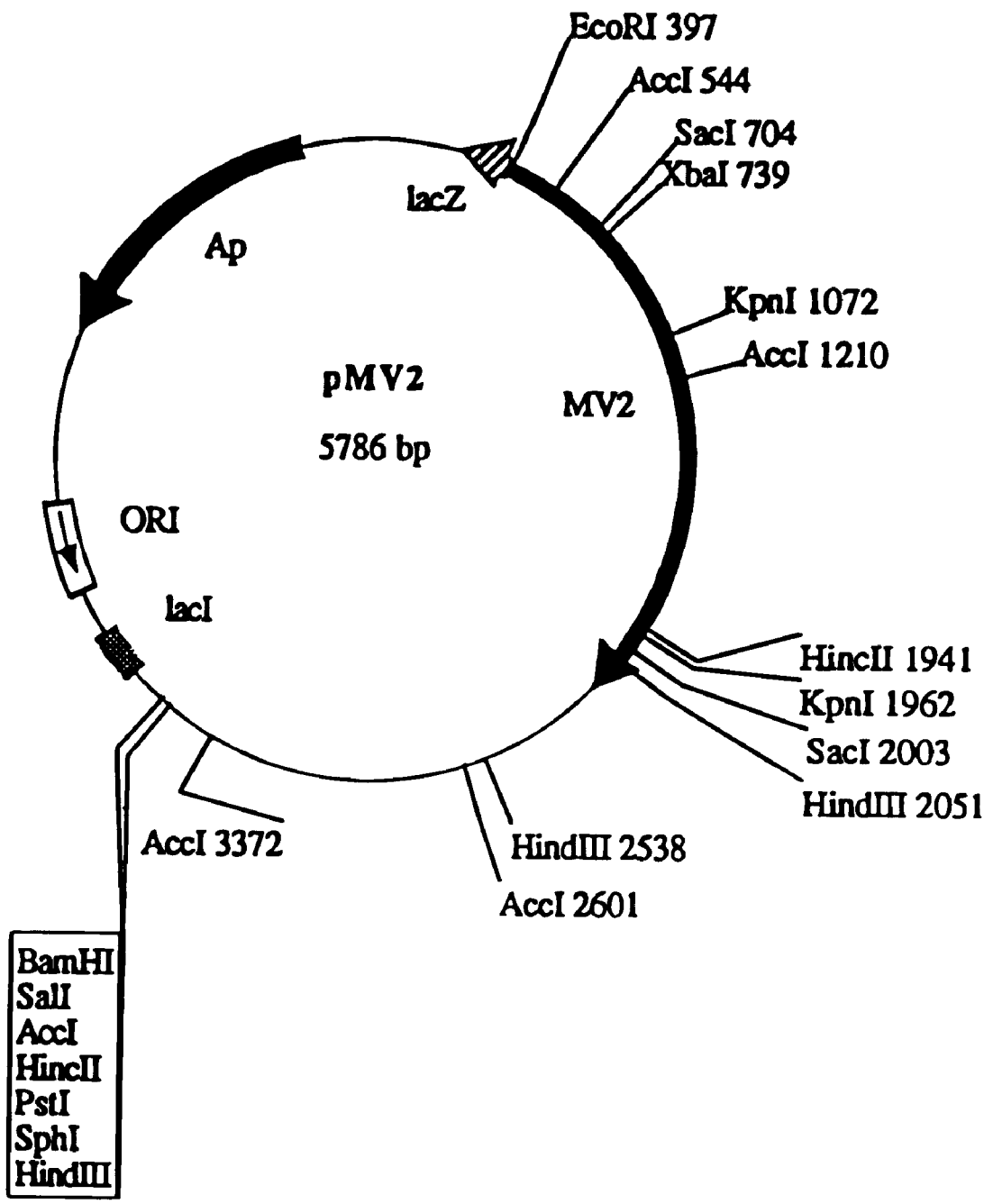

FIG. 10 is a microphotograph of a fungal hypha (f) growing between the algal walls (w). Note grains of floridean starch (s) and thylakoids (arrows) in the algal cell.

In FIG. 14, the total number of bases is 4726—and the DNA sequence composition is: 1336 A; 1070 C; 1051 G; 1269 T. The ATG start codon is shown in bold. The introns are underlined. The stop codon is shown in italics.

In FIG. 15, the total number of bases is 4670—and the DNA sequence composition is: 1253 A; 1072 C; 1080 G; 1265 T. The ATG start codon is shown in bold. The introns are underlined. The stop codon is shown in italics.

In FIG. 16, the two aligned sequences are those obtained from MC (total number of residues: 1066) and MV (total number of residues: 1070). The comparison matrix used was a structure-genetic matrix (Open gap cost: 10; Unit gap cost : 2). In this Figure, the character to show that two aligned residues are identical is ':'. The character to show that two aligned residues are similar is '.'. The amino acids said to be similar are: A,S,T; D,E; N,Q; R,K; I,L,M,V; F,Y,W. Overall there is: Identity: 920 (86.30%); Similarity: 51 (4.78%). The number of gaps inserted in MC is 1 and the number of gaps inserted in MV is 1.

In the attached sequence listings: SEQ. I.D. No. 5 is the amino-acid sequence for GL obtained from *Morchella costata;* SEQ. I.D. No. 6 is the amino-acid sequence for GL obtained from *Morchella vulgaris;* SEQ. I.D. No. 7 is the nucleotide coding sequence for GL obtained from *Morchella costata;* and SEQ. I.D. No. 8 is the nucleotide coding sequence for GL obtained from *Morchella vulgaris.*

In SEQ. I.D. No. 5 the total number of residues is 1066. The GL enzyme has an amino acid composition of:

| 46 Ala | 13 Cys | 25 His | 18 Met | 73 Thr |
|--------|--------|--------|--------|--------|
| 50 Arg | 37 Gln | 54 Ile | 43 Phe | 23 Trp |
| 56 Asn | 55 Glu | 70 Leu | 56 Pro | 71 Tyr |
| 75 Asp | 87 Gly | 71 Lys | 63 Ser | 78 Val |

In SEQ.I.D. No. 6 the total number of residues is 1070. The GL enzyme has an amino acid composition of:

| 51 Ala | 13 Cys | 22 His | 17 Met | 71 Thr |
|--------|--------|--------|--------|--------|
| 50 Arg | 40 Gln | 57 Ile | 45 Phe | 24 Trp |
| 62 Asn | 58 Glu | 74 Leu | 62 Pro | 69 Tyr |
| 74 Asp | 87 Gly | 61 Lys | 55 Ser | 78 Val |

Experiments

1 The Soluble Enzyme System 1.1. Effect of pH on the Stability and Activity of the Lyase Isolated from Fugal Infected *Gracilariopsis lemaneiformis*.

Two buffer systems, namely HOAc and NaOAc and sodium citrate—citric acid in a concentration of 5 mM—were tested at 37° C. The pH range tested was from pH 3 to pH 5.2. The lyase showed maximum activity in a pH range between 3.6 to 4.2. At pH 3, the stability and activity of the enzyme decreased by about 90%. At pH 5.2, the activity decreased by about 64%. However, the enzyme was considerably more stable at this pH than at pH 3, as the AF yield obtained at pH 5.2 was 75% of the AF yield obtained at pH 3.8. Slightly higher AF yield was obtained in the HOAc and NaOAc buffer than in citrate buffer. This is not due to any differential effect of the two buffers (final conc. is 125 μM in the AF assay mixture) in the AF assay method.

1.2. Effect of Temperature on the Activity and Stability of the Lyase

This experiment was conducted at optimal pH range. At 25° C. the production of AF was linear up to at least 9 days. This indicates that no loss of activity and stability of the lyase occurred within 9 days. With increasing temperature, the stability of the enzyme decreased.

The half life of the enzyme activity at the following temperature was:
30° C. 5 days
37° C. 2.5 days
40° C. less than 1 day
500C. less than 1 day 1.3. Effect of Substrate Concentration on the Stability of the Lyase and AF Yield It was observed that amylopectin and dextrins have a stabilizing effect on the lyase while the smallest substrate maltose does not. This was verified for both the soluble enzyme system and the immobilized enzyme system.

AF yield increases with the increase in amylopectin concentration up to 25%. In the case of dextrin, the AF yield decreases when the concentration exceeds 30% (30%, 40% and 50% were tested).

1.4 Activation and Inactivation of Lyase

No metal ions are found necessary for the activity and the enzyme catalysed reaction can surprisingly proceed in pure water. The fact that the addition of EDTA in the reaction mixture up to 20 mM had little effect on the activity clearly demonstrates that metal ions are not essential for the activity of the lyase enzyme according to the present invention.

This means that in the AF purification step, the ion exchange chromatography step that takes away salts from the reaction system can be omitted, if water is used as reaction medium. However, inclusion of NaCl in the reaction mixture in a concentration of 0.85% (0.145 M) can increase the AF yield up to 1-fold.

1.5. Substrate Specificity

Upon cooling solubilized starch will tend to form rigid gels when the starch concentration becomes to high. Therefore it is an advantage to utilize partly degraded starch as substrate for the 1,4-glucan lyase.

The specificity of α-1,4-glucan lyase isolated from M. costata for different oligosaccharides was tested. The oligosaccharides were maltose (G2), maltotriose (G3), maltotetraose (G4), maltopentaose (G5), maltohexaose (G6) and maltoheptaose (G7). The oligosaccharides were dissolved in $H_2O$ at a concentration of 8 mg/ml. The enzyme assay contained 150 μl substrate G2/G3/G4/G5/G6/G7, 120 μl 0.1M MBS pH 6.3 and 30 μl purified enzyme. The reaction mixture was incubated for 60 min at 30° C. Afterwards the reaction was stopped by boiling for 3 min and 900 μl absolute ethanol was added for precipitation. After centrifugation at 20.000×g for 5 min at 4° C. the supernatant was transferred to a new eppendorf tube and lyophilized.

The freeze-dried samples were dissolved in 1000 μl $H_2O$ and were filtrated through a 0.22 μm Millipore filter before 25 μl of the sample was loaded on the Dionex HPLC.

1.7 HPLC

Analytical Procedures

Analyses were performed on a Dionex 4500i chromatography system consisting of a GPM-2 pump and a PED detector which was used in pulse-amperometric detection mode.

The anion exchange columns were a CarboPac PA-100 (4×250 mm) and a CarboPac PA-100 guard column (3×25 mm) from Dionex.

The eluent were 200 mM sodium hydroxide (A), 500 mM sodium acetate (B) and 18 M ohm de-ionized water (C). The pump was programmed in 2 different ways, method no. 1 and method no. 2:

| | Method no. 1: | | | | |
|---|---|---|---|---|---|
| Time, min | 0.0 | 3.0 | 3.1 | 26.9 | 29.0 |
| % A | 10 | 10 | 50 | 50 | 10 |
| % B | 0 | 0 | 0 | 32 | 0 |
| % C | 90 | 90 | 50 | 18 | 90 |

| | Method no. 2: | |
|---|---|---|
| Time, min. | 0.0 | 30 |
| % A | 10 | 10 |
| % B | 0 | 0 |
| % C | 90 | 90 |

Standards

Glucose, maltose, maltotriose, maltotetraose, maltopentaose, maltohexaose and maltoheptaose (all from Sigma) and 1,5-anhydrofructose were used as standards. All compounds were dissolved in 18 M ohm de-ionized water which was filtered through a 0.22 μm Millipore filter before use.

1.7 Results

The analyses show that the purified enzyme which was isolated from M. costata indeed was able to use maltooligosaccharides as substrate 1 for 1,5-anhydrofructose formation.

When maltose was used as substrate, almost no 1,5-anhydrofructose was formed but when the other maltooligosaccharides (G3–G7) were used, high amounts of this compound were produced.

It is clear that higher amounts of 1,5-anhydrofructose were obtained when a longer maltooligosaccharide was used.

This observation corresponds perfectly well with the theory of the lyase forming 1,5-anhydrofructose from the non-reducing end of the substrate, leaving only the terminal glucose molecule unchanged.

1.8 Formation of AF

α-1,4-glucan lyase from M.costata hydrolyses starch to the end-product 1,5-anhydrofructose. The end-product was shown by HPLC, method 2. The enzyme assay contained 500 μl amylopectin (20 mg/ml, dissolved in $H_2O$), 400 μl 0.1M MES pH 6.3 and 100 μl purified enzyme. The reaction mixture was incubated at 30° C. and the reaction was stopped by boiling after 30 or 120 min incubation. High-molecular oligosaccharides were precipitated by addition of 3 vol abs. ethanol and the sample was centrifuged and freeze-dried as described above. The samples were dissolved in 125 μl H$_2$O and 25 μl were applied on the HPLC column.

The HPLC elution profile clearly shows that α-1,4-glucan lyase from *M.costata* produces 1,5-anhydrofructose by hydrolysis of starch. Equal amounts of 1,5-anhydrofructose were found after 30 and 120 min. incubation which indicate that the enzyme activity is not inhibited by the endproduct 1,5-anhydrofructose.

$^{13}$C NMR spectra (water) of AF prepared in this way shows that it adopts one major form giving rise to the following signals: δ93.5 (quart, C-2), 81.5 (CH, C-5), 77.7 (CH, C-3), 72.6 (CH$_2$, C-1), 69,8 (CH, C-4), 62.0 (CH$_2$, C-6). Assignments are based on H—H C—H and C—H 2D correlation spectra.

1.6. The Cooperative Effect of Lyase with Pullulanase and Isoamylase

As it can be seen from Table 1, the inclusion of pullulanase in the reaction mixture will obviously increase the AF yield by about 15–23%, depending on whether soluble starch or amylopectin is used as substrate.

TABLE

The cooperation of pullulanase and lyase in the production of AF.

| Substrate | Lyase | Pullulanase | AF Yield (%) | Glc Yield (%) |
|---|---|---|---|---|
| Solubl. Starch | + | − | 51 | 0 |
|  | − | + | 0 | 0.37 |
|  | + | + | 66.0 | 3.9 |
| Amylopectin | + | − | 48.0 | 0 |
|  | − | + | 0 | 0.33 |
|  | + | + | 71.3 | 3.7 |

+, enzyme added, − enzyme omitted.

The reaction mixture contained 0.3 ml 2% potato amylopectin (Sigma) in water or 0. 3 ml 2% soluble starch (Merck), 2 μl lyase and 0.36 units pullulanase (BM) as indicated.

The reaction was carried out at 30° C. for 1 day. At the end of the reaction, samples were taken for AF and Glc analysis.

In the case of isoamylase, the advantage is that the optimal pH of the lyase overlaps with that of Pseudomonas isoamylase (pH 3.0–4.5). The problem, however, is that isoamylase will produce an excess amount of long chain amylose that precipitates from the solution, and therefore is no longer suitable as a substrate for the lyase. It can be expected that the cooperation of the lyase with isoamylase will be efficient, if the chain of amylose is not too long.

2. The Immobilized Enzyme System

Immobilization of the lyase was achieved by using succinimide-activated Sepharose (Affigel 15 gel, Bio-Rad) and glutaradehye-activated Silica gel (BM). The recovery of lyase activity after immobilization on Affigel 15 gel was between 40% to 50%. There may be some lyase that is still active after immobilization, but is inaccessible to the substrate because of the steric hindrance, especially in the case of macromolecules like starches. Immobilized enzymes used in the industry usually have an activity recovery of around 50%.

The most interesting thing of the Affigel 15 gel immobilized lyase is that its stability has been greatly improved at pH 5.5. When the column was operated at this pH, the stability was at least 16 days long. The pH shift in the stability is very important considering the optimal pH of pullulanase which is around pH 5.5. This is the prerequisite for the lyase and pullulanase to cooperate efficiently in the same reactor with the same physico-chemical environment. The soluble lyase has an optimal pH between 3.6 and 4.2, and at this pH range pullulanase shows little or no activity.

With the silica gel immobilized lyase, the activity recovery is very high, around 80–100%. However, the silica gel immobilized enzyme was not stable when the column was operated neither at pH 3.8 nor pH 5.5. It is possible that some lyase was adsorbed on the surface of the silica gel beads and was slowly released from the silica gel after each washing of the column. It may therefore be the adsorbed lyase that contributes to the high recovery rate and the decrease in column activity.

3. Purification of AF 3.1. The Lyase-Amylopectin/Soluble Starch System

In this system, the reaction system contained AF, limit dextrin, the lyase, and buffer salts at the end of the reaction. AF was separated from the macromolecules limit dextrin and the lyase) by ethanol (final conc. 50%) precipitation. Unprecipitated low-molecular-weight amylopectin was separated by ultrafiltration using Amicon YM3 membranes (cut-off 3,000). Ethanol was removed by evaporation at 40° C. in a rotary evaporator. Buffer salts were removed from AF by mixed ion exchangers. Purified solid AF was obtained by freeze-drying.

3.2. The Lyase-Pullulanase/Amylopectin/Soluble Starch System

In this system the final products are AF and glucose. If at least a substantially pure sample of AF is to be prepared, the by-product glucose must be removed. This can be achieved by enzymatic methods. First the glucose is converted into gluconic acid and hydrogen peroxide by glucose oxidase.

Catalase is needed to dispel H$_2$O$_2$ formed. H$_2$O$_2$ will oxidize AF into two new compounds which are at present of unknown structure. The other impurities in the AF preparation are the oxidation products of AF. It was observed that AF can slowly be oxidized by air-level of oxygen, especially at high temperature, high AF concentration and long time of exposure.

Gluconic acid was removed together with the buffer salts by ion exchange chromatography.

In this system, the low-molecular-weight amylopectin molecules may alternatively be hydrolysed by amyloglucosidase instead of using ultrafiltration.

3.3. The Purity Checking of AF

The purity of the AF preparations were confirmed by TLC, Dionex and NMR.

3.4 Analysis of the Antioxidative Activity of Anhydro Fructose

Electrochemical Oxygen Consumption

Method

The activity of AF was investigated in a methyl linoleate emulsion as described by Jorgensen and Skibsted (Z. Lebensm. Unters. Forsch. (1993) 196: 423–429) with minor modifications: To 5.00 ml of a 1.33 mM methyl linoleate emulsion in 5.0 mM aqueous phosphate buffer with pH=5.8 and 0.2 w/w % Tween 20 as emulsifier was added AF in the following concentrations: 0, 15, 146 and 680μM. The oxidation in the system was initiated by addition of 50 μl 0.26 M metmyoglobin (MMb) final concentration 0.26 mM. Immediately after initiating the reaction the sample was injected to a thermostated (25.0±0.1° C.) 70 μl closed cell, effectively excluding diffusion of oxygen into the system. The oxygen consumption was measured by a Clark electrode, which was connected to a PC data collection program. The relative oxygen concentration (%) was registered every 30s.

Results

Figure 19:
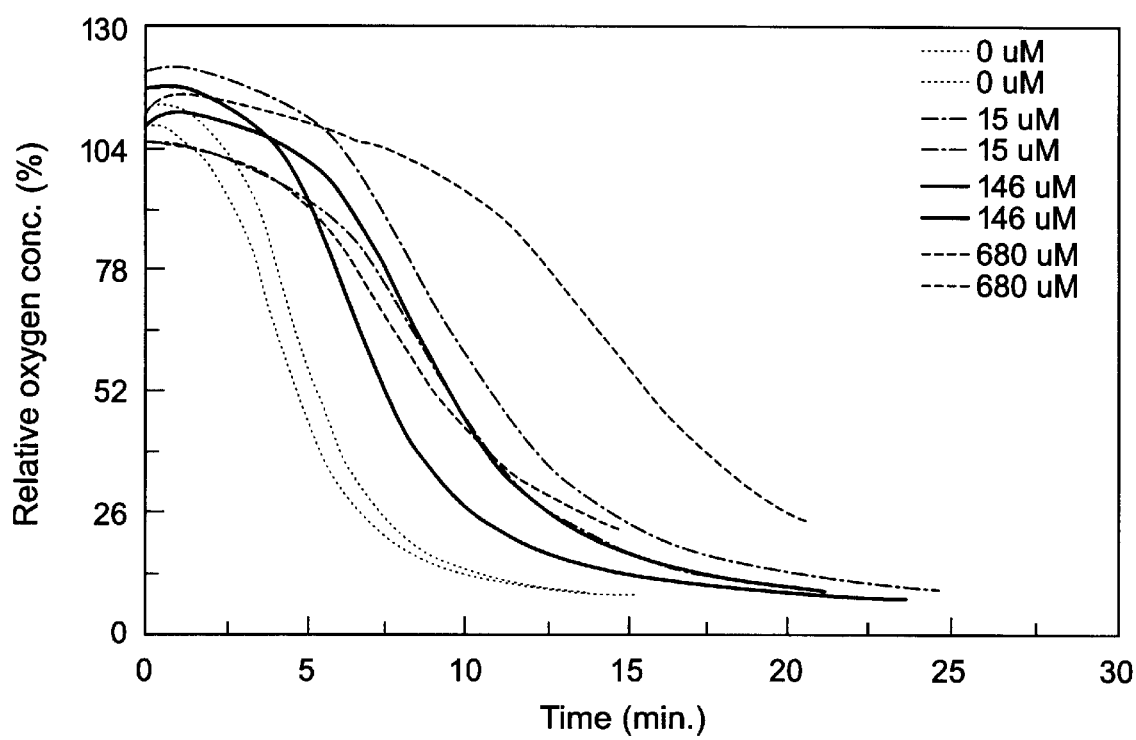

Curves corresponding to oxygen consumption for the different samples are illustrated in FIG. 19. For samples without addition of AF a relative decrease in oxygen concentration is seen immediately after injection of the sample. For samples containing AF a lag-phase is observed before the curve breaks off and the oxygen concentration is reduced. After the lag-phase only a minor reduction in the oxygen consumption rate is observed compared to samples without AF added. A tendency for samples having the highest amount of AF to have the longest lag-phase is observed. As well the rate for oxygen consumption is lower for these samples, which is seen by a smaller slope of the curves compared to the slope for the references (0 $\mu$M).

ESR Analysis

Method

Hydroxyl radicals were generated by a Fenton reaction with $H_2O_2$ (0.17 mM) and $FeSO_4$ (4.8 $\mu$M). The generated radicals were trapped by 5,5-dimethyl-1-pyrroline N-oxide (DMPO, 9.7 mM). AF was added in concentrations of 1.3 mM and 6.3 mM. A water soluble extract of rosemary (*Rosmarinus officinalis* L.) was analyzed in a concentration of 0.25 mg/ml (in grams equivalent to 1.26 mM AF). Measurements were carried out at room temperature (20±1° C.) after 120 s and repeated for the same reaction mixture after 300 s with the following spectrometer settings: Center field 3475.60 G; sweep width 55 G; microwave power 20 mW; modulation frequency 100 kHz; modulation amplitude 1.01 G; receiver gain 1.00·$10^5$; conversion time 81.92 ms time constant 163.84 ms and sweep time 83.89 s.

Results

The generated hydroxyl radicals were trapped by DMPO. The spin adduct gives rise to a characteristic 1:2:2:1 ESR spectrum. The peak height of the spectrum is proportional to the quantitative amount of generated spin adduct. Addition of both DMPO and AF will set up a competition between the spin trap and AF. A reduction of peak height will indicate a good scavenging activity of AF.

TABLE

Peak height of ESR-spectra. $H_2O_2$ = 0.17 mM and $Fe^{2+}$ = 4.8 $\mu$M.

| Anhydro fructose [mM] | Rosemary extract [mg/ml] | Peak height [120 s] | Peak height [300 s] |
|---|---|---|---|
| 0 | 0 | 2475 | 2780 |
| 1.3 | 0 | 2634 | 2545 |
| 6.3 | 0 | 1781 | 1900 |

At a concentration of 1.3 mM AF no scavenging activity of hydroxyl radicals is seen, at 6.3 mM Af the peak height is reduced, indicating that a part of the generated hydroxyl radicals is scavenged by AF.

4. Use of AF as an Anti-oxidant

EXAMPLE 4.1

Use of AF as an Anti-oxidant in a 50% Mayonnaise

50% mayonnaise is used for salads, open sandwiches, etc. in both the catering and the retail trades. The low oil content of 50% mayonnaise makes it suitable for low-calorie applications.

A typical mayonnaise composition is as follows:

| | |
|---|---|
| Soya oil | 50.0% |
| Tarragon vinegar (10%) | 4.0% |
| Egg yolk | 3.5% |
| Sugar | 3.0% |
| Salt | 1.0% |
| Potassium sorbate | 0.1% |
| Water | 35.2% |
| MAYODAN 602 | 3.0% |
| Lemon flavouring 10251 | 0.2% |

MAYODAN 602 ensures a fine, stable oil dispersion and the required viscosity, thereby providing 50% mayonnaise with a long shelf life.

Flavouring 10251 is a natural lemon flavouring which provides mayonnaise with the fresh taste of lemon.

Typically the mayonnaise is prepared by the following method:

1) Dry mix the MAYODAN 602, sugar and salt. Disperse in oil in a ratio of 1 part powder to 2 parts oil.
2) Add flavouring and potassium sorbate to the water and pour into the Koruma mixer. Add 1).
3) Add the egg yolk.
4) Add the oil continuously in a vacuum.
5) After ⅔ of the oil has been added (slowly), blend the tarragon vinegar with the remaining ⅓ of the oil, and add.

The following data show that when AF is added to the mayonnaise as an anti-oxidant the results are comparable to the known food anti-oxididants GRINDOX 142 and GRINDOX 1029.

| GRINDOX 142: | |
|---|---|
| Ascorbyl palmitate | 10% |
| Propyl gallate | 20% |
| Citric acid | 10% |
| Food grade emulsifier | 60% |
| Form at 25° C. | paste |
| Colour | grey to pale brown |
| Density | 1.1 g/ml |
| GRINDOX 1029: | |
| Ascorbyl palmitate | 20% |
| Natural tocopherols | 20% |
| Food grade emulsifier | 60% |
| Form at 25° C. | paste |
| Colour | light brown |
| Density at 25° C. | 1.0 g/ml |

(All percentages are by weight).

In the test procedure the anti-oxidants were added to the mayonnaise to provide an anti-oxidant concentration in the order of about 500 ppm. The mayonnaise was then placed in a bomb calorimeter at temperature 80° C. containing pure $O_2$. An induction period to the onset of substantial oxidation of the product is then measured.

The results were as follows.

| Samples: | IP (hours) |
|---|---|
| 1. Blank | 28.0 |
| 2. +500 ppm GRINDOX 142 | 35.0 |

-continued

| Samples: | IP (hours) |
|---|---|
| 3. +500 ppm GRINDOX 1029 | 33.3 |
| 4. +550 ppm GRINDOX 1029 | 34.3 |
| 5. +500 ppm 1,5 anhydro-D-fructose | 32.0 |

(IP hours = Induction Period)

These results show that AF is an excellent food antioxidant and is comparable with the known foodstuffs antioxidants GRINDOX 142 or GRINDOX 1029.

EXAMPLE 4.2

Use of AF as an Anti-oxidant in a Salad Dressing

Yogurt Salad Dressing with 50% Oil

Yogurt salad dressing with 50% oil is used for salads, potatoes, raw vegetable salad, meat, fish and boiled vegetables.

| Composition | |
|---|---|
| Soya oil | 50.0% |
| Yogurt (plain) | 39.0% |
| Vinegar (10%) | 3.5% |
| Sugar | 3.0% |
| Egg yolk | 2.0% |
| Salt | 1.0% |
| Potassium sorbate | 0.1% |
| MAYODAN 525 | 1.4% |
| Acid masking flavouring 2072 | 0.02% |

MAYODAN 525 provides unique emulsion stability, prevents syneresis, ensures uniform oil dispersion and viscosity, improves tolerance to production processes and ensures a long shelf life.

Flavouring 2072 is a nature-identical, acid masking flavouring reducing the acidulated taste of dressing without affecting its pH value.

Process

1. Dry mix MAYODAN 525, sugar and salt. Disperse in oil in a ratio of 1 part powder to 2 parts oil.
2. Fill flavouring, potassium sorbate and yogurt into the Koruma mixer. Add 1).
3. Add the egg yolk.
4. Add the oil continuously in a vacuum.
5. After ⅔ of the oil has been added (slowly), blend the vinegar with the remaining ⅓ of the oil, and add.
Add spices if required.

| Test results: | | |
|---|---|---|
| Sample: | IP hours | PF |
| 1. Blank | 37.2 | 1.00 |
| 2. 500 ppm anhydrofructose | 39.5 | 1.06 |
| 3. 800 ppm GRINDOX 1032 | 43.3 | 1.07 |

(IP - Induction Period);
(PF - Protection Period)

Protection Factor (PF)

For each temperature defined as PF=IP of the oil with added antioxidant/IP of the same oil without added antioxidant Life Extension (LE) %

LE=(PF−1.0)×100

6. Preparations of α-1.4-glucan Lyase

Introduction

With regard to a further embodiments of the present invention the enzyme α-1,4-glucan lyase for use in preparing the AF may be isolated from a fungally infected algae, preferably fungally infected *Gracilariopsis lemaneiformis* more preferably fungally infected *Gracilariopsis lemaneiformis* from Qingdao (China).

Alternatively the enzyme may be obtained from a fungus. For example, the fungus can be any one of Discina perlata, *Discina parma, Gyromitra gigas, Gyromitra influa, Mitrophora hybrida, Morchella conica, Morchella costata, Morchella elata, Morchella hortensis, Morchella rotunda, Morchella vulgaris, Peziza badia, Sarcosphaera eximia, Disciotis venosa, Gyromitra esculenta, Helvella crispa, Helvella lacunosa, Leptopodia elastica, Verpa digitaliformis,* and other forms of Morchella. Preferably the fungus is *Morchella costata* or *Morchella vulgaris*.

With regard to a further embodiment of the present invention the enzyme α-1,4-glucan lyase for use in preparing the AF may be isolated from algae alone, preferably *Gracilariopsis lemaneiformis* more preferably Gracilariopsis lemaneiformis from Santa Cruz (Calif.).

The initial enzyme purification can be performed by the method as described by Yu et al (ibid). However, preferably, the initial enzyme purification includes an optimized procedure in which a solid support is used that does not decompose under the purification step. This gel support further has the advantage that it is compatible with standard laboratory protein purification equipment. The details of this optimized purification strategy are given later on. The purification is terminated by known standard techniques for protein purification.

The purity of the enzyme can be readily established using complementary electrophoretic techniques.

A. Source=Fungally Infected Algae

The following sequence information was used to generate primers for the PCR reactions mentioned below and to check the amino acid sequence generated by the respective nucleotide sequences.

Amino Acid Sequence Assembled from Peptides from Fungus Infected *Gracilariopsis lemaneiformis*

Tyr Arg Trp Gln Glu Val Leu Tyr Thr Ala Met Tyr Gln Asn Ala

Ala Phe Gly Lys Pro Ile Ile Lys Ala Ala Ser Met Tyr Asn Asn

Asp Ser Asn Val Arg Arg Ala Gln Asn Asp His Phe Leu Leu Gly

Gly His Asp Gly Tyr Arg Ile Leu Cys Ala Pro Val Val Trp Glu

Asn Ser Thr Glu Arg Glu Leu Tyr Leu Pro Val Leu Thr Gln Trp

Tyr Lys Phe Gly Pro Asp Phe Asp Thr Lys Pro Leu Glu Gly Ala

The Amino Acid Sequence (27–34) Used to Generate Primer A and B (Met Tyr Asn Asn Asp Ser Asn Val)
Primer A
ATG TA(TC) AA(CT) AA(CT) GA(CT) TC(GATC) AA(CT) GT 128 mix
Primer B
ATG TA(TC) AA(CT) AA(CT) GA(CT) AG(CT) AA(CT) GT 64 mix The Amino Acid Sequence (45–50) Used to Generate Primer C (Gly Gly His Asp Gly Tyr)
Primer C
TA (GATC)CC (GA)TC (GA)TG (GATC)CC (GATC)CC 256 mix
[The Sequence Corresponds to the Complementary Strand.]

The Amino Acid Sequence (74–79) Used to Generate Primer E (Gln Trp Tyr Lys Phe Gly)
Primer E
GG(GATC) CC(GA) AA(CT) TF(GA) TAC CA(CT) TG 64 mix

[The Sequence Corresponds to the Complementary Strand.]

The Amino Acid Sequence (1–6) Used to Generate Primer F1 and F2 (Tyr Arg Trp Gln Glu Val)
Primer F1
TA(TC) CG(GATC) TGG CA(GA) GA(GA) GT 32 mix
Primer F2
TA(TC) AG(GA) TGG CA(GA) GA(GA) GT 16 mix The Sequence Obtained from the First PCR Amplification (Clone 1)
ATGTACAACA ACGACTCGAA CGTTCGCAGG GCG-CAGAACG ATCATTCCT TCTTGGCGGC CACGACG-GTT A
Met Tyr Asn Asn Asp Ser Asn Val Arg Arg Ala Gln Asn Asp His Phe Leu Leu Gly Gly His Asp Gly The Sequence Obtained from the Second PCR Amplification (Clone 1)

ATGTACAACA ACGACTCGAA CGTTCGCAGG GCGCAGAACG ATCATTTCCT

TCTTGGTGGA CATGATGGAT ATCGCATTCT GTGCGCGCCT GTTGTGTGGG

AGAATTCGAC CGAACGNGAA TTGTACTTGC CCGTGCTGAC CCAATGGTAC

AAATTCGGCC C

Met Tyr Asn Asn Asp Ser Asn Val Arg Arg Ala Gln Asn Asp His Phe Leu Leu Gly

Gly His Asp Gly Tyr Arg Ile Leu Cys Ala Pro Val Val Trp Glu Asn Ser Thr Glu

Arg Glu Leu Tyr Leu Pro Val Leu Thr Gln Trp Tyr Lys Phe Gly Pro

The Sequence Obtained from the Third PCR Amplification (Clone2)

TACAGGTGGC AGGAGGTGTT GTACACTGCT ATGTACCAGA

ATGCGGCTTT CGGGAAACCG ATTATCAAGG CAGCTTCCAT

GTACGACAAC GACAGAAACG TTCGCGGCGC ACAGGATGAC

CACTTCCTTC TCGGCGGACA CGATGGATAT CGTATTTTGT

GTGCACCTGT TGTGTGGGAG AATACAACCA GTCGCGATCT

GTACTTGCCT GTGCTGACCA GTGGTACAAA TTCGGCCC

Tyr Arg Trp Gln Glu Val Leu Tyr Thr Ala Met Tyr Gln Asn Ala Ala Phe Gly Lys

Pro Ile Ile Lys Ala Ala Ser Met Tyr Asp Asn Asp Arg Asn Val Arg Gly Ala Gln Asp

Asp His Phe Leu Leu Gly Gly His Asp Gly Tyr Arg Ile Leu Cys Ala Pro Val Val

-continued

Trp Glu Asn Thr Thr Ser Arg Asp Leu Tyr Leu Pro Val Leu Thr Lys Trp Tyr Lys

Phe Gly

A.1. Cytological Investigations of *Gracilariopsis lemaneiformis*

A.1.1.1 Detection of Fungal Infection in *Gracilariopsis lemaneiformis*

Sections of *Gracilariopsis lemaneiformis* collected in China were either hand cut or cut from paraffin embedded material. Sectioned material was carefully investigated by light microscopy. Fungal hyphae were clearly detected in *Gracilariopsis lemaneiformis*.

The thalli of the *Gracilariopsis lemaneiformis* are composed of cells appearing in a highly ordered and almost symmetric manner. The tubular thallus of G. lemaneiformis is composed of large, colorless central cells surrounded by elongated, slender, ellyptical cells and small, round, red pigmented peripherial cells. All algal cell types are characterized by thick cell walls. Most of the fungal hyphae are found at the interphase between the central layer of large cells and the peripheral layer. These cells can clearly be distinguished from the algae cells as they are long and cylindrical. The growth of the hyphae is observed as irregularities between the highly ordered algae cells. The most frequent orientation of the hypha is along the main axis of the algal thallus. Side branches toward the central and periphery are detected in some cases. The hypha can not be confused with the endo/epiphytic 2nd generation of the algae.

Calcofluor White is known to stain chitin and cellulose containing tissue. The reaction with chitin requires four covalently linked terminal n-acetyl glucosamine residues. It is generally accepted that cellulose is almost restricted to higher plants although it might occur in trace amounts in some algae. It is further known that chitin is absent in Gracilaria.

Calcofluor White was found to stain domains corresponding to fungi hyfa cell walls in sectioned *Gracilariopsis lemaneiformis* material.

Figure 1:
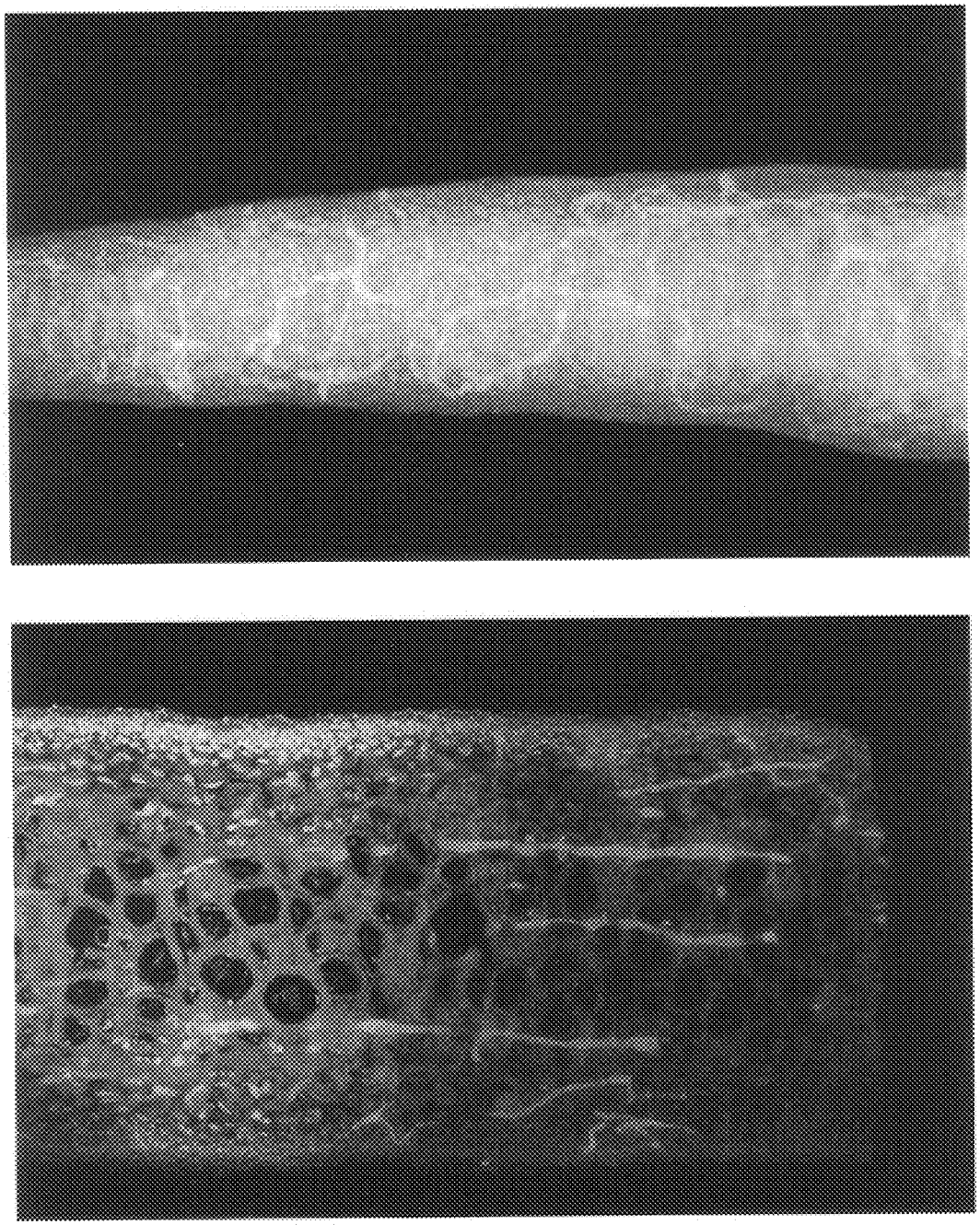

The hypha appear clear white against a faint blue background of Gracilaria tissue when observed under u.v. light—see FIG. 1. Chitin is the major cell wall component in most fungi but absent in Gracilaria. Based upon these observations we conclude that the investigated algae is infected by a fungi. 40% of the lower parts of the investigated *Gracilariopsis lemaneiformis* sections were found to be infected with fungal hyphae. In the algae tips 25% of the investigated Gracilariopsis lemaneiformis sections were found to be infected.

Figure 2:
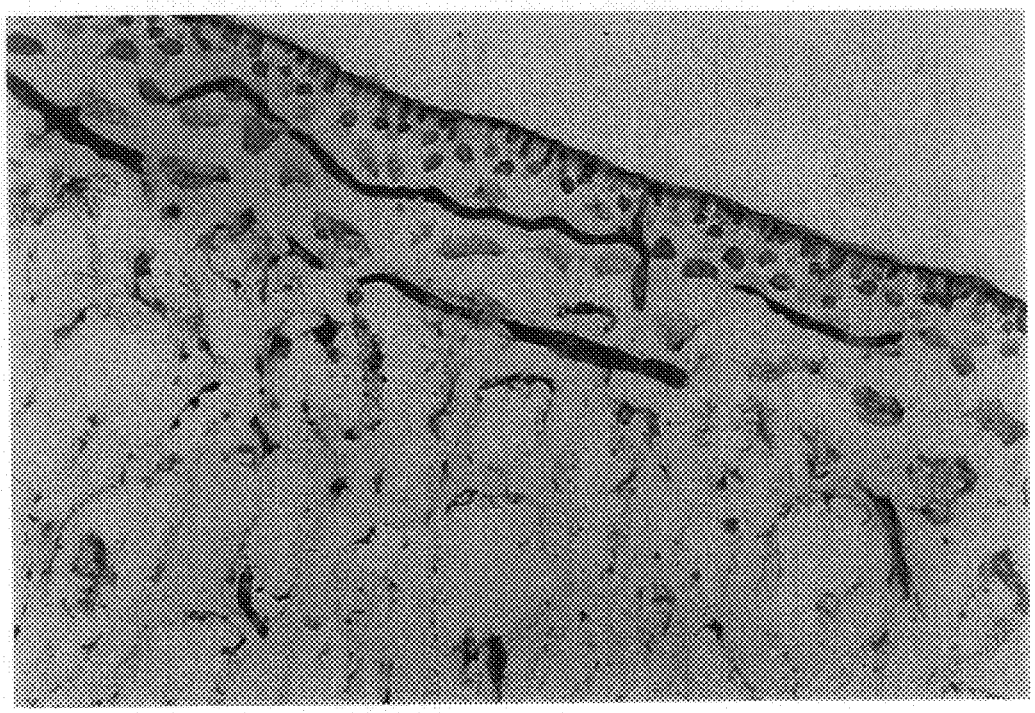
FIG. 2 shows PAS/Anilinblue Black staining of *Gracilariopsis lemaneiformis* with fungi. The fungi have a significant higher content of carbohydrates.
Figure 3:
FIG. 3 shows a micrograph showing longitudinal and grazing sections of two thin-walled fungal hypha (f) growing between thick walls (w) of algal cells. Note thylacoid membranes in the algal chloroplast (arrows).

Staining of sectioned *Gracilariopsis lemaneiformis* with Periodic acid Schiff (PAS) and Aniline blue black revealed a significantly higher content of carbohydrates within the fungal cells as compared with the algae cells—see FIG. 2. Safranin 0 and Malachit Green showed the same colour reaction of fungi cells as found in higher plants infected with fungi.

An Acridin Orange reaction with sectioned *Gracilariopsis lemaneiformis* showed clearly the irregularly growth of the fungus.

A. 1.1.2 Electron Microscopy

Slides with 15 μm thick sections, where the fungus was detected with Calcofluor White were fixed in 2% $OsO_4$, washed in water and dehydrated in dimethoxypropane and absolute alcohol. A drop of a 1:1 mixture of acetone and Spurr resin was placed over each section on the glass slide, and after one hour replaced by a drop of pure resin. A gelatin embedding capsule filled with resin was placed face down over the section and left over night at 4° C. After the polymerization at 55° C. for 8 hrs, the thick sections adhering to the resin blocks could can be separated from the slide by immersion in liquid nitrogen.

Blocks were trimmed and 100 nm thick sections were cut using a diamond knife on a microtome. The sections were stained in aqueous uranyl acetate and in lead citrate. The sections were examined in an electron microscope at 80 kV.

The investigation confirmed the ligth microscopical observations and provided further evidence that the lyase producing, chinese strain of G. lamneiformis is infected by a fungal parasite or symbiont.

Fungal hyphae are build of tubular cells 50 to 100 μm long and only few microns in diameter. The cells are serially arranged with septate walls between the adjacent cells. Ocasional branches are also seen. The hyphae grow between the thick cell walls of algal thallus without penetrating the wall or damaging the cell. Such a symbiotic association, called mycophycobiosis, is known to occur between some filamentous marine fungi and large marine algae (Donk and Bruning, 1992—Ecology of aquatic fungi in and on algae. In Reisser, W.(ed.): Algae and Symbioses: Plants, Animals, Fungi, Viruses, Interactions Explored. Biopress Ltd., Bristol.)

Examining the microphotograph in FIG. 10, several differences between algal and fungal cells can be noticed. In contrast to several μm thick walls of the alga, the fungal walls are only 100–200 nm thick. Plant typical organells as chloroplasts with thyllacoid membranes as well as floridean starch grains can be seen in algal cells, but not in the fungus.

Intercellular connections of red algae are characterized by specific structures termed pit plugs, or pit connections The structures are prominent, electron dense cores and they are important features in algal taxonomy (Pueschel, C. M.: An expanded survey of the ultrastructure of Red algal pit plugs. J. Phycol. 25, 625, (1989)). In our material, such connections were frequently observed in the algal thallus, but never between the cells of the fungus.

A. 1.2 In situ Hybridization Experiments

In situ hybridization technique is based upon the principle of hybridization of an antisense ribonucotide sequence to the mRNA. The technique is used to visualize areas in microscopic sections where said mRNA is present. In this particular case the technique is used to localize the enzyme α-1,4-glucan lyase in sections of *Gracilariopsis lemaneiformis*.

A. 1.2. 1 Preparation of $^{35}S$ Labelled Probes for In situ Hybridization

A 238 bp PCR fragment from a third PCR amplification—called clone 2 (see above)—was cloned into the pGEM-3Zf (+) Vector (Promega). The transcription of the antisense RNA was driven by the SP6 promotor, and the sense RNA by the T7 promotor. The Ribonuclease protection assay kit (Ambion) was used with the following modifications. The transcripts were run on a 6% sequencing gel to remove the unincorporated nucleotide and eluted with the elution buffer supplied with the T7RNA polymerase in vitro Transcription Kit (Ambion). The antisense transcript contained 23 noncoding nucleotides while the sense contained 39. For hybridization $10^7$ cpm/ml of the $^{35}S$ labelled probe was used.

In situ hybridisation was performed essentially as described by Langedale et.al.(1988). The hybridization temperature was found to be optimal at 45° C. After washing at 45° C. the sections were covered with KodaK K-5 photographic emulsion and left for 3 days at 5° C. in dark (Ref: Langedale, J. A., Rothermel, B. A. and Nelson, T. (1988). Genes and development 2: 106–115. Cold Spring Harbour Laboratory).

Figure 4:
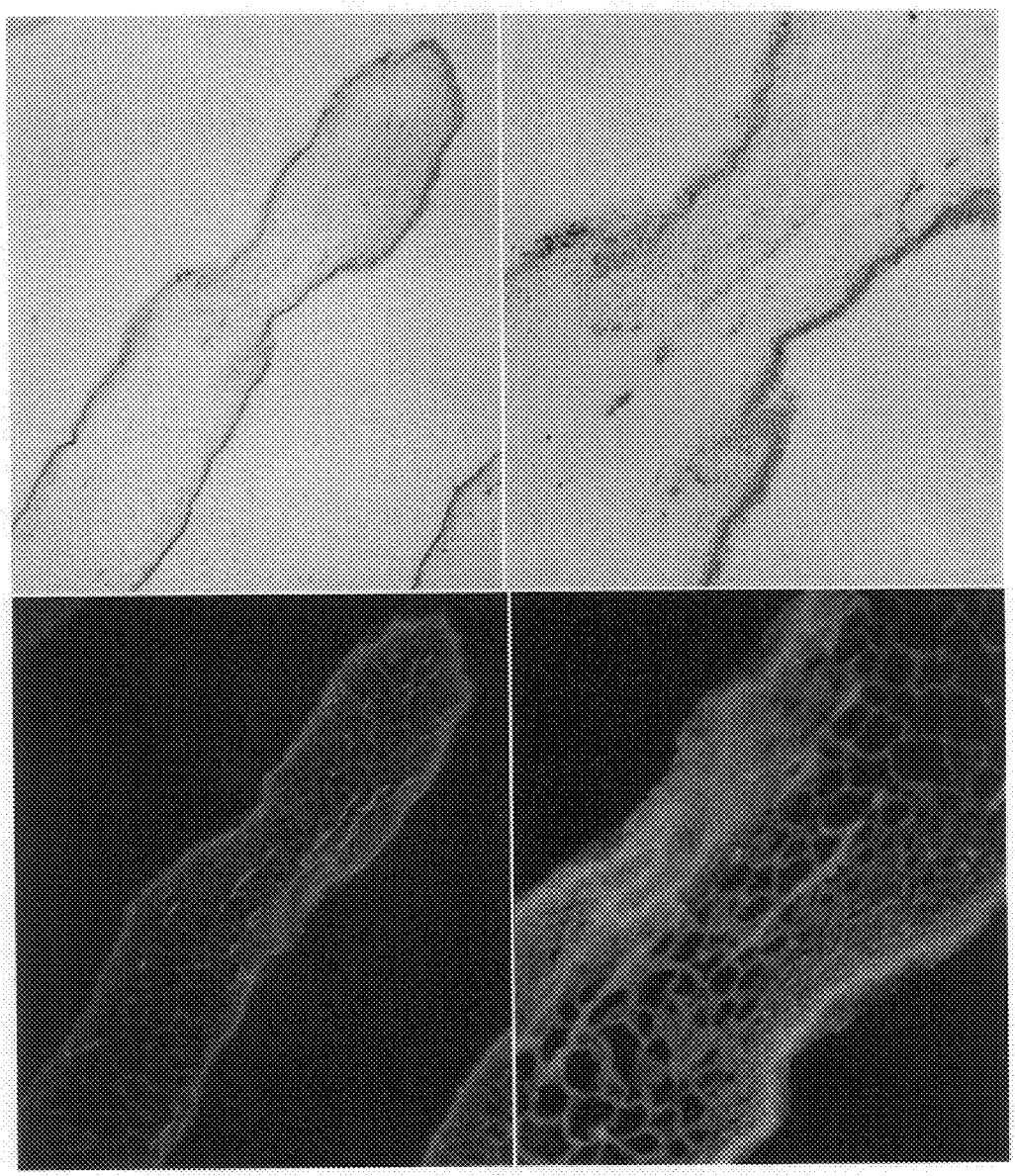
FIG. 4 shows the antisense detections with clone 2 probe (upper row) appear to be restricted to the fungi illustrated by Calcoflour White staining of the succeeding section (lower row) (46x and 108x).
Figure 5:
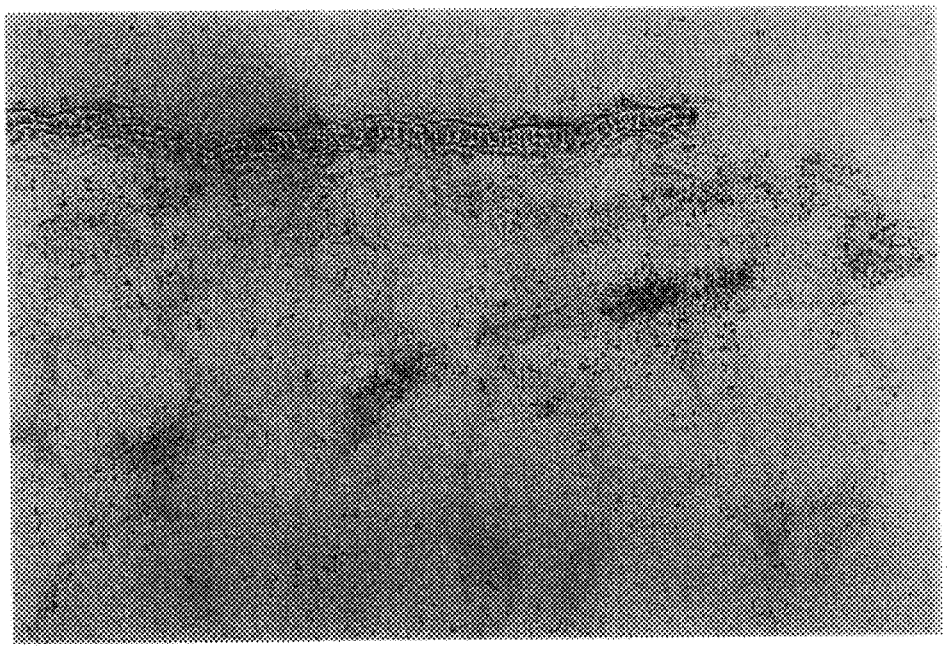
FIG. 5 shows intense antisense detections with clone 2 probe are found over the fungi in *Gracilariopsis lemaneiformis* (294x).
Figure 6:
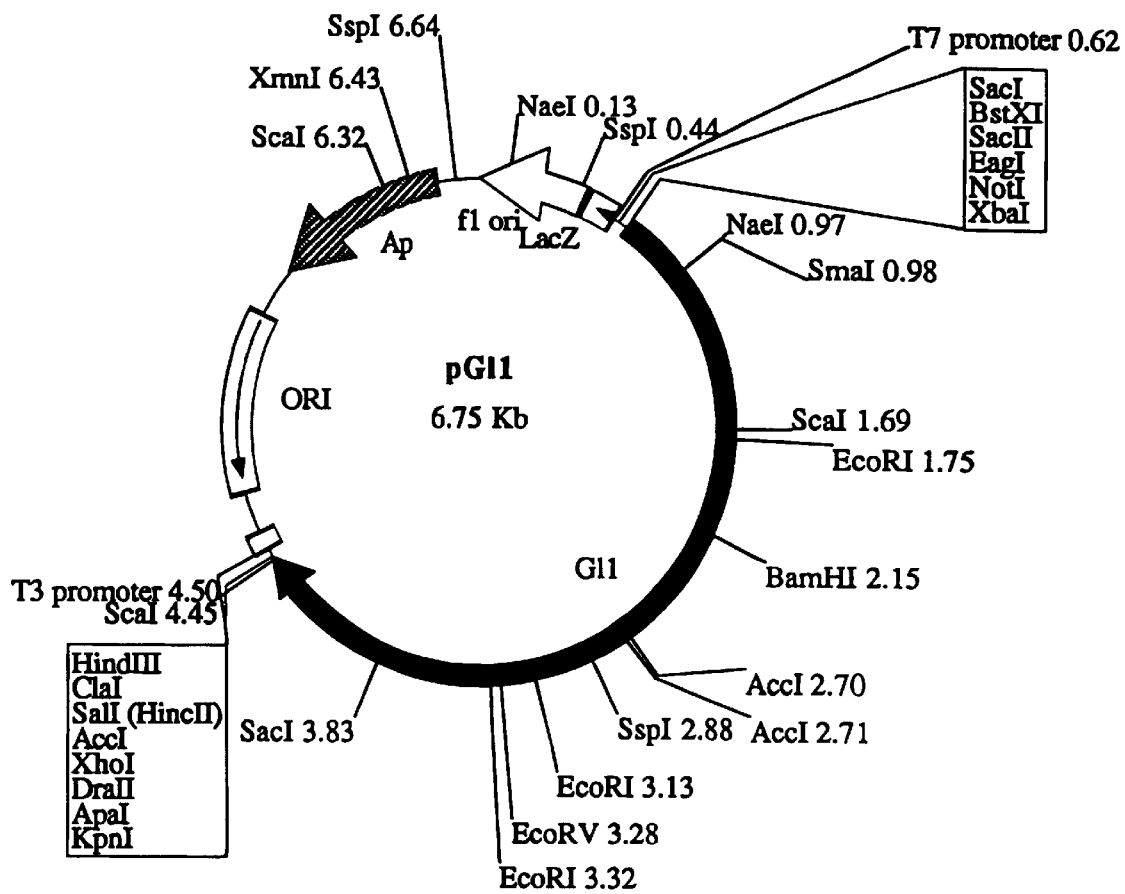
FIG. 6 shows a map of plasmid pGL1—which is a pBluescript II KS containing a 3.8 kb fragment isolated from a genomic library constructed from fungal infected *Gracilariopsis lemaneiformis*. The fragment contains a gene coding for alpha-1,4-glucan lyase.
Figure 7:
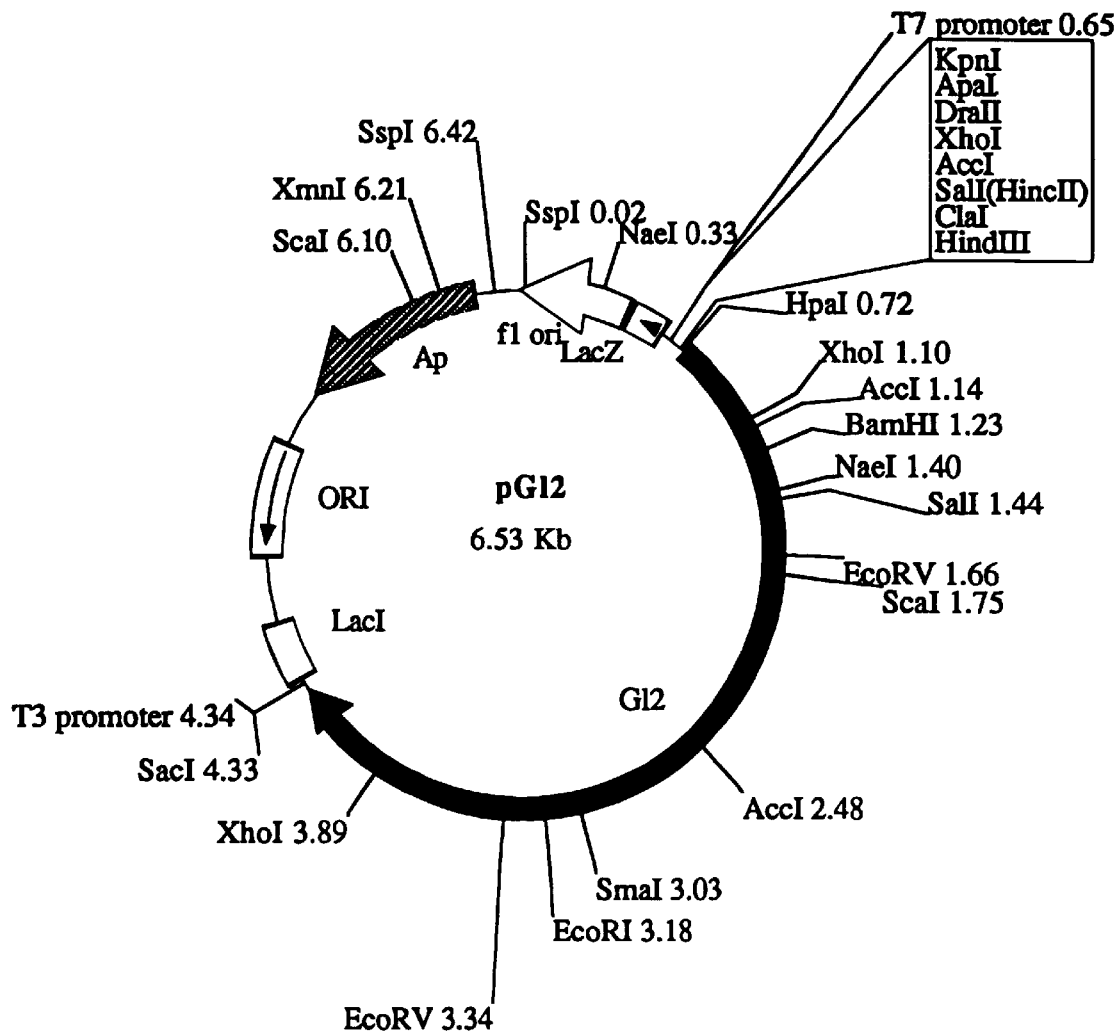
FIG. 7 shows a map of plasmid pGL2—which is a pBluescript II SK containing a 3.6 kb fragment isolated from a genomic library constructed from fungal infected *Gracilariopsis lemaneiformis*. The fragment contains a gene coding for alpha-1,4-glucan lyase.

The in situ hybridization experiments with riboprobes against the mRNA of α-1,4-glucan lyase, show strong hybridizations over and around the hypha of the fungus detected in *Gracilariopsis lemaneiformis*—see FIGS. 4 and 5. This is considered a strong indication that the α-1,4-glucan lyase is produced. A weak random background reactions were detected in the algae tissue of both *Gracilariopsis lemaneiformis*. This reaction was observed both with the sense and the antisense probes. Intense staining over the fungi hypha was only obtained with antisense probes.

These results were obtained with standard hybridisation conditions at 45° C. in hybridization and washing steps. At 50° C. no staining over the fungi was observed, whereas the background staining remained the same. Raising the temperature to 55° C. reduced the background staining with both sense and antisense probes significantly and equally.

Based upon the cytological investigations using complementary staining procedures it is concluded that *Gracilariopsis lemaneiformis* is fungus infected. The infections are most pronounced in the lower parts of the algal tissue.

In sectioned *Gracilariopsis lemaneiformis* material in situ hybridization results clearly indicate that hybridization is restricted to areas where fungal infections are found—see FIG. 4. The results indicate that α-1,4-glucan lyase mRNA appears to be restricted to fungus infected areas in *Gracilariopsis lemaneiformis*. Based upon these observations we conclude that α-1,4-glucan lyase activity is detected in fungally infected *Gracilariopsis lemaneiformis*.

A.2. Enzyme Purification and Characterization

Purification of α-1,4-glucan lyase from fungal infected *Gracilariopsis lemaneiformis* material was performed as follows.

A.2. 1 Materials and Methods

The algae were harvested by filtration and washed with 0.9% NaCl. The cells were broken by homogenization followed by sonication on ice for 6×3 min in 50 mM citrate-NaOH pH 6.2 (Buffer A). Cell debris were removed by centrifugation at 25,000×g for 40 min. The supernatant obtained at this procedure was regarded as cell-free extract and was used for activity staining and Western blotting after separation on 8–25% gradient gels.

A.2.2 Separation by β-cyclodextrin Sepharose Gel

The cell-free extract was applied directly to a β-cyclodextrin Sepharose gel 4B column (2.6×18 cm) pre equilibrated with Buffer A. The column was washed with 3 volumes of Buffer A and 2 volumes of Buffer A containing 1 M NaCl. α-1,4-glucan lyase was eluted with 2% dextrins in Buffer A. Active fractions were pooled and the buffer changed to 20 mM Bis-tris propane-HCl (pH 7.0, Buffer B).

Active fractions were applied onto a Mono Q HR 5/5 column pre-equilibrated with Buffer B. The fungal lyase was eluted with Buffer B in a linear gradient of 0.3 M NaCl.

The lyase preparation obtained after β-cyclodextrin Sepharose chromatography was alternatively concentrated to 150 μl and applied on a Superose 12 column operated under FPLC conditions.

A.2.3 Assay for α-1,4-glucan Lyase Activity and Conditions for Determination of Substrate Specificity, pH and Temperature Optimum The reaction mixture for the assay of the α-1,4-glucan lyase activity contained 10 mg ml$^{-1}$ amylopectin and 25 mM Mes-NaOH (pH 6.0). The reaction was carried out at 30° C. for 30 min and stopped by the addition of 3,5-dinitrosalicylic acid reagent. Optical density at 550 nm was measured after standing at room temperature for 10 min.

A.3. Amino Acid Sequencing of the α-1.4-glucan Lyase from Fungus Infected *Gracilariopsis lemaneiformis*

A.3.1 Amino Acid Sequencing of the Lyases

The lyases were digested with either endoproteinase Arg-C from *Clostridium histolyticum* or endoproteinase Lys-C from *Lysobacter enzymogenes*, both sequencing grade purchased from Boehringer Mannheim, Germany. For digestion with endoproteinase Arg-C, freeze dried lyase (0.1 mg) was dissolved in 50μl 10 M urea, mM methylamine, 0.1 M Tris-HCl, pH 7.6. After overlay with $N_2$ and addition of 10 μl of 50 mM DTT and 5 mM EDTA the protein was denatured and reduced for min at 50° C. under $N_2$. Subsequently, 1 μg of endoproteinase Arg-C in 10μl of 50 mM Tris-HCl, pH 8.0 was added, $N_2$ was overlayed and the digestion was carried out for 6h at 37° C. For subsequent cysteine derivatization, 12.5 μl 100 mM iodoacetamide was added and the solution was incubated for 15 min at RT in the dark under $N_2$.

For digestion with endoproteinase Lys-C, freeze dried lyase (0.1 mg) was dissolved in 50 μl of 8 M urea, 0.4 M $NH_4HCO_3$, pH 8.4. After overlay with $N_2$ and addition of 5 μl of 45 mM DTT, the protein was denatured and reduced for 15 min at 50° C. under $N_2$. After cooling to RT, 5 μl of 100 mM iodoacetamide was added for the cysteines to be derivatized for 15 min at RT in the dark under $N_2$.

Subsequently, 90 μl of water and 5 μg of endoproteinase Lys-C in 50 μl of 50 mM tricine and 10 mM EDTA, pH 8.0, was added and the digestion was carried out for 24 h at 37° C. under $N_2$.

The resulting peptides were separated by reversed phase HPLC on a VYDAC C18 column (0.46×15 cm; 10 μm; The Separations Group; California) using solvent A: 0.1% TEA in water and solvent B: 0.1% TFA in acetonitrile. Selected peptides were rechromatographed on a Develosil C18 column (0.46×10 cm; 3 μm; Dr. Ole Schou, Novo Nordisk, Denmark) using the same solvent system prior to sequencing on an Applied Biosystems 476A sequencer using pulsed-liquid fast cycles.

The amino acid sequence information from the enzyme derived from fungus infected *Gracilariopsis lemaneiformis* is shown below, in particular SEQ. ID. No. 1. and SEQ. ID. No. 2.

SEQ. I.D. No. 1 has

Number of residues: 1088.

Amino acid composition (including the signal sequence)

| 61 Ala | 15 Cys | 19 His | 34 Met | 78 Thr |
|---|---|---|---|---|
| 51 Arg | 42 Gln | 43 Ile | 53 Phe | 24 Trp |
| 88 Asn | 53 Glu | 63 Leu | 51 Pro | 58 Tyr |
| 79 Asp | 100 Gly | 37 Lys | 62 Ser | 77 Val |

SEQ. I.D. No. 2 has
Number of residues: 1091.
Amino acid composition (including the signal sequence)

| 58 Ala | 16 Cys | 14 His | 34 Met | 68 Thr |
|---|---|---|---|---|
| 57 Arg | 40 Gln | 44 Ile | 56 Phe | 23 Trp |
| 84 Asn | 47 Glu | 69 Leu | 51 Pro | 61 Tyr |
| 81 Asp | 102 Gly | 50 Lys | 60 Ser | 76 Val |

A.3.2 N-terminal Analysis

Studies showed that the N-terminal sequence of native glucan lyase 1 was blocked. Deblocking was achieved by treating glucan lyase 1 blotted onto a PVDF membrane with anhydrous TFA for 30 min at 40° C. essentially as described by LeGendre et al. (1993) [Purification of proteins and peptides by SDS-PAGE; In: Matsudaira, P. (ed.) A practical guide to protein and peptide purification for microsequencing, 2nd edition; Academic Press Inc., San Diego; pp. 74–101.]. The sequence obtained was TALSDKQTA, which matches the sequence (sequence position from 51 to 59 of SEQ. I.D. No.1) derived from the clone for glucan lyase 1 and indicates N-acetylthreonine as N-terminal residue of glucan lyase 1. Sequence position 1 to 50 of SEQ. I.D. No. 1 represents a signal sequence.

A.4. DNA Sequencing of Genes Coding for the α-1.4-glucan Lyase from Fungus Infected *Gracilariopsis lemaneiformis*

A.4.1 Methods for Molecular Biology

DNA was isolated as described by Saunders (1993) with the following modification: The polysaccharides were removed from the DNA by ELUTIP-d (Schleicher & Schuell) purification instead of gel purification. (Ref:Saunders, G. W. (1993). Gel purification of red algal genomic DNA: An inexpensive and rapid method for the isolation of PCR-friendly DNA. Journal of phycology 29(2): 251–254 and Schleicher & Schuell: ELUTIP-d. Rapid Method for Purification and Concentration of DNA.)

A.4.2 PCR

The preparation of the relevant DNA molecule was done by use of the Gene Amp DNA Amplification Kit (Perkin Elmer Cetus, USA) and in accordance with the manufactures instructions except that the Taq polymerase was added later (see PCR cycles) and the temperature cycling was changed to the following:

| no of cycles | C | time (min.) |
|---|---|---|
| PCR cycles: | | |
| 1 | 98 | 5 |
| | 60 | 5 |
| addition of Taq polymerase and oil | | |
| 35 | 94 | 1 |
| | 47 | 2 |
| | 72 | 3 |
| 1 | 72 | 20 |

A.4.3 Cloning of PCR Fragments

PCR fragments were cloned into pT7Blue (from Novagen) following the instructions of the supplier.

A.4.4 DNA Sequencing

Double stranded DNA was sequenced essentially according to the dideoxy method of Sanger et al. (1979) using the Auto Read Sequencing Kit (Pharmacia) and the Pharmacia LKB A.L.F.DNA sequencer. (Ref.: Sanger, F., Nicklen, S. and Coulson, A. R.(1979). DNA sequencing with chain-determinating inhibitors. Proc. Natl. Acad. Sci. USA 74: 5463–5467.)

The sequences are shown as SEQ. I.D. No.s 1 and 2. In brief:
SEQ. I.D. No. 3 has
Total number of bases: 3267.
DNA sequence composition: 850 A; 761 C; 871 G; 785 T
SEQ. I.D. No. 4 has
Total number of bases: 3276.
DNA sequence composition: 889 A; 702 C; 856 G; 829 T A.4.5 Screening of the Library Screening of the Lambda Zap library obtained from Stratagene, was performed in accordance with the manufacturer's instructions except that the prehybridization and hybridization was performed in 2×SSC, 0.1% SDS, 10×Denhardt's and 100g/ml denatured salmon sperm DNA. To the hybridization solution a 32P-labeled denatured probe was added. Hybridization was performed over night at 55° C. The filters were washed twice in 2×SSC, 0.1% SDS and twice in 1×SSC, 0.1% SDS.

A.4.6 Probe

The cloned PCR fragments were isolated from the pT7 blue vector by digestion with appropriate restriction enzymes. The fragments were separated from the vector by agarose gel electrophoresis and the fragments were purified from the agarose by Agarase (Boehringer Mannheim). As the fragments were only 90–240 bp long the isolated fragments were exposed to a ligation reaction before labelling with 32P-dCTP using either Prime-It random primer kit (Stratagene) or Ready to Go DNA labelling kit (Pharmacia).

A.4.7 Results

A.4.7.1 Generation of PCR DNA Fragments Coding for α-1,4-glucan Lyase

The amino acid sequences of three overlapping tryptic peptides from α-1,4-glucan lyase were used to generate mixed oligonucleotides, which could be used as PCR primers (see the sequences given above).

In the first PCR amplification primers A/B (see above) were used as upstream primers and primer C (see above) was used as downstream primer. The size of the expected PCR product was 71 base pairs.

In the second PCR amplification primers A/B were used as upstream primers and E was used as downstream primer. The size of the expected PCR product was 161 base pairs.

In the third PCR amplification primers F1 (see above) and F2 (see above) were used as upstream primers and E was used as downstream primer. The size of the expected PCR product was 238 base pairs.

The PCR products were analysed on a 2% LMT agarose gel and fragments of the expected sizes were cut out from the gel and treated with Agarase (Boehringer Manheim) and cloned into the pT7blue Vector (Novagen) and sequenced.

The cloned fragments from the first and second PCR amplification coded for amino acids corresponding to the sequenced peptides (see above). The clone from the third amplification (see above) was only about 87% homologous to the sequenced peptides.

A.4.7.2 Screening of the Genomic Library with the Cloned PCR Fragments

Screening of the library with the above-mentioned clones gave two clones. One clone contained the nucleotide sequence of SEQ I.D. No. 4 (gene 2). The other clone contained some of the sequence of SEQ I.D. No.3 (from base pair 1065 downwards) (gene 1).

The 5' end of SEQ. I.D. No. 3 (i.e. from base pair 1064 upwards) was obtained by the RACE (rapid amplification of cDNA ends) procedure (Michael, A. F., Michael, K. D. & Martin, G. R.(1988). Proc.Natl.Acad.Sci.USA 85:8998–99002.) using the 5' race system from Gibco BRL. Total RNA was isolated according to Collinge et al. (Collinge, D. B., Milligan D. E:, Dow, J. M., Scofield, G. & Daniels, M. J.(1987). Plant Mol Biol 8: 405–414). The 5' race was done according to the protocol of the manufacturer, using 1 µg of total RNA. The PCR product from the second amplification was cloned into pT7blue vector from Novagen according to the protocol of the manufacturer. Three independent PCR clones were sequenced to compensate for PCR errors.

An additional PCR was performed to supplement the clone just described with XbaI and NdeI restriction sites immediately in front of the ATG start codon using the following oligonucleotide as an upstream primer:
GCTCTAGAGC<u>ATG</u>TTTTCAACCCTTGCG
and a primer containing the complement sequence of bp 1573–1593 in sequence GL1 (i.e. SEQ. I.D. No. 3) was used-as a downstream primer.

The complete sequence for gene 1 (i.e. SEQ. I.D. No. 3) was generated by cloning the 3' end of the gene as a BamHI-HindIII fragment from the genomic clone into the pBluescript II KS+ vector from Stratagene and additionally cloning the PCR generated 5' end of the gene as a XbaI-BamHI fragment in front of the 3' end.

Gene 2 was cloned as a HindIII blunt ended fragment into the EcoRV site of pbluescript II SK+ vector from Stratagene. A part of the 3' untranslated sequence was removed by a SacI digestion, followed by religation. HindIII and HpaI restriction sites were introduced immediately in front of the start ATG by digestion with HindIII and NarI and religation in the presence of the following annealed oligonucleotides

```
AGCTTGTTAACATGTATCCAACCCTCACCTTCGTGG

ACAATTGTACATAGGTTGGGAGTGGAAGCACCGC
```

No introns were found in the clones sequenced.

The clone 1 type (SEQ. ID. No.3) can be aligned with all ten peptide sequences (see FIG. 8) showing 100% identity. Alignment of the two protein sequences encoded by the genes isolated from the fungal infected algae *Gracilariopsis lemaneiformis* shows about 78% identity, indicating that both genes are coding for a α-1.4-glucan lyase.
Expression of the GL Gene in Micro-organisms
(E.G. Analyses of Pichia Lyase Transformants and Aspergillus Lyase Transformants)

The DNA sequence encoding the GL was introduced into microorganisms to produce an enzyme with high specific activity and in large quantities.

In this regard, gene 1 (i.e. SEQ. I.D. No. 3) was cloned as a NotI-HindIII blunt ended (using the DNA blunting kit from Amersham International) fragment into the Pichia expression vector pHIL-D2 (containing the AOX1 promoter) digested with EcoRI and blunt ended (using the DNA blunting kit from Amersham International) for expression in *Pichia pastoris* (according to the protocol stated in the Pichia Expression Kit supplied by Invitrogen).

In another embodiment, the gene I (i.e. SEQ. I.D. No. 3) was cloned as a NotI-HindIII blunt ended fragment (using the DNA blunting kit from Amersham International) into the Aspergillus expression vector pBARMTE1 (containing the methyl tryptophan resistance promoter from *Neuropera crassa*) digested with SmaI for expression in *Aspergillus niger* (Pall et al (1993) Fungal Genet Newsletter vol 40 pages 59–62). The protoplasts were prepared according to Daboussi et al (Curr Genet (1989) vol 15 pp 453–456) using lysing enzymes Sigma L-2773 and the lyticase Sigma L-8012. The transformation of the protoplasts was followed according to the protocol stated by Buxton et al (Gene (1985) vol 37 pp 207–214) except that for plating the transformed protoplasts the protocol laid out in Punt et al (Methods in Enzymology (1992) vol 216 pp 447–457) was followed but with the use of 0.6% osmotic stabilised top agarose.

The results showed that lyase activity was observed in the transformed *Pichia pastoris* and *Aspergillus niger*.

A.5.1 General Methods

Preparation of cell-free extracts.

The cells were harvested by centrifugation at 9000 rpm for 5 min and washed with 0.9% NaCl and resuspended in the breaking buffer (50 mM K-phosphate, pH 7.5 containing 1 mM of EDTA, and 5% glycerol). Cells were broken using glass beads and vortex treatment. The breaking buffer contained 1 mM PMSF (protease inhibitor). The lyase extract (supernatant) was obtained after centrifugation at 9000 rpm for 5 min followed by centrifugation at 20,000×g for 5min.

Assay of lyase activity by alkaline 3,5-dinitrosalicylic acid reagent (DNS)

One volume of lyase extract was mixed with an equal volume of 4% amylopectin solution. The reaction mixture was then incubated at a controlled temperature and samples were removed at specified intervals and analyzed for AF.

The lyase activity was also analyzed using a radioactive method.

The reaction mixture contained 10 µl $^{14}$C-starch solution (1 µCi; Sigma Chemicals Co.) and 10 µl of the lyase extract. The reaction mixture was left at 25° C. overnight and was then analyzed in the usual TLC system. The radioactive AF produced was detected using an Instant Imager (Pachard Instrument Co., Inc., Meriden, Conn.).

Electrophoresis and Western Blotting

SDS-PAGE was performed using 8–25% gradient gels and the PhastSystem (Pharmacia). Western blottings was also run on a Semidry transfer unit of the PhastSystem.

Primary antibodies raised against the lyase purified from the red seaweed collected at Qingdao (China) were used in a dilution of 1:100. Pig antirabbit IgG conjugated to alkaline phosphatase (Dako A/S, Glostrup, Denmark) were used as secondary antibodies and used in a dilution of 1:1000.

Part I, Analysis of the Pichia Transformants containing the Above Mentioned Construct Results 1. Lyase activity was determined 5 days after induction (according to the manual) and proved the activity to be intracellular for all samples in the B series.

| Samples of B series: | 11 | 12 | 13 | 15 | 26 | 27 | 28 | 29 | 30 |
|---|---|---|---|---|---|---|---|---|---|
| Specific activity: | 139 | 81 | 122 | 192 | 151 | 253 | 199 | 198 | 150 |

*Specific activity is defined as nmol AF released per min per mg protein in a reaction mixture containing 2% (w/v) of glycogen, 1% (w/v) glycerol in 10 mM potassium phosphate buffer (pH 7.5). The reaction temperature was 45° C.; the reaction time was 60 min.

A time course of sample B27 is as follows. The data are also presented in FIG. 1

| Time (min) | 0 | 10 | 20 | 30 | 40 | 50 | 60 |
|---|---|---|---|---|---|---|---|
| Spec. act. | 0 | 18 | 54 | 90 | 147 | 179 | 253 |

Assay conditions were as above except that the time was varied.

2. Western-blotting Analysis

The CFE of all samples showed bands with a molecular weight corresponding to the native lyase.

| MC-Lyase expressed intracellulary in *Pichia pastoris* | |
|---|---|
| Names of culture | Specific activity* |
| A18 | 10 |
| A20 | 32 |
| A21 | 8 |
| A22 | 8 |
| A24 | 6 |

Part II, The Aspergilus Transformants

Results

I. Lyase Activity was Determined after 5 days Incubation (Minimal Medium Containing 0.2% Casein Enzymatic Hydrolysate Analysis by the Alkaline 3,5-dinitrosalicylic Acid Reagent 1). Lyase Activity Analysis of the Culture Medium Among 35 cultures grown with 0.2% amylopectin included in the culture medium, AF was only detectable in two cultures. The culture medium of 5.4+ and 5.9+ contained 0.13 g AF/liter and 0.44 g/liter, respectively. The result indicated that active lyase had been secreted from the cells. Lyase activity was also measurable in the cell-free extract.

2). Lyase Activity Analysis in Cell-free Extracts

| Name of the culture | Specific activity* |
|---|---|
| 5.4+ | 51 |
| 5.9+ | 148 |
| 5.13 | 99 |
| 5.15 | 25 |
| 5.19 | 37 |

*The specific activity was defined as nmol of AF produced per min per mg protein at 25° C.
+ indicates that 0.2% amylopectin was added.

The results show that Gene 1 of GL was expressed intracellular in *A. niger*.

Experiments with transformed *E.coli* (using cloning vectors pQE30 from the Qia express vector kit from Qiagen) showed expression of enzyme that was recognised by antibody to the enzyme purified from fungally infected *Gracilariopsis lemaneiformis*.

B. Source=Fungus

B.1. Enzyme Purification and Characterization of the α-1, 4-glucan Lyase from the Fungus *Morchella costata*

B.1.1 Materials and Methods

The fungus *Morchella costata* was obtained from American Type Culture Collection (ATCC). The fungus was grown at 25° C. on a shaker using the culture medium recommended by ATCC. The mycelia were harvested by filtration and washed with 0.9% NaCl.

The fungal cells were broken by homogenization followed by sonication on ice for 6×3 min in 50 mM citrate-NaOH pH 6.2 (Buffer A). Cell debris were removed by centrifugation at 25,000×g for 40 min. The supernatant obtained at this procedure was regarded as cell-free extract and was used for activity staining and Western blotting after separation on 8–25% gradient gels.

B. 1.2 Separation by β-cyclodextrin Sepharose Gel

The cell-free extract was applied directly to a β-cyclodextrin Sepharose gel 4B column ( 2.6×18 cm) pre equilibrated with Buffer A. The column was washed with 3 volumes of Buffer A and 2 volumes of Buffer A containing 1 M NaCl. α-1,4-glucan lyase was eluted with 2% dextrins in Buffer A. Active fractions were pooled and the buffer changed to 20 mM Bis-tris propane-HCl (pH 7.0, Buffer B).

Active fractions were applied onto a Mono Q HR 5/5 column pre-equilibrated with Buffer B. The fungal lyase was eluted with Buffer B in a linear gradient of 0.3 M NaCl. The lyase preparation obtained after β-cyclodextrin Sepharose chromatography was alternatively concentrated to 150 µl and applied on a Superose 12 column operated under FPLC conditions.

B.1.3 Assay for α-1,4-glucan lyase activity and conditions for determination of substrate specificity, pH and temperature optimum The reaction mixture for the assay of the α-1,4-glucan lyase activity contained 10 mg ml$^{-1}$ amylopectin and 25 mM Mes-NaOH (pH 6.0).

The reaction was carried out at 30 ° C. for 30 min and stopped by the addition of 3,5-dinitrosalicylic acid reagent. Optical density at 550 nm was measured after standing at room temperature for 10 min. 10 mM EDTA was added to the assay mixture when cell-free extracts were used.

The substrate amylopectin in the assay mixture may be replaced with other substrates and the reaction temperature may vary as specified in the text.

In the pH optimum investigations, the reaction mixture contained amylopection or maltotetraose 10 mg ml$^{-1}$ in a 40 mM buffer. The buffers used were glycine-NaOH (pH 2.0–3.5), HoAc-NaoAc (pH 3.5–5.5), Mes-NaOH (pH 5.5–6.7), Mops-NaOH (6.0–8.0) and bicine-NaOH (7.6–9.0). The reactions were carried out at 30° C. for 30 min. The reaction conditions in the temperature optimum investigations was the same as above except that the buffer Mops-NaOH (pH 6.0) was used in all experiments. The reaction temperature was varied as indicated in the text.

SDS-PAGE, Native-PAGE and isoelectrofocusing were performed on PhastSystem (Pharmacia, Sweden) using 8–25% gradient gels and gels with a pH gradient of 3–9, respectively. Following electrophoresis, the gels were stained by silver staining according to the procedures recommended by the manufacturer (Pharmacia). The glycoproteins were stained by PAS adapted to the PhastSystem. For activity staining, the electrophoresis was performed under native conditions at 6° C.

Following the electrophoresis, the gel was incubated in the presence of 1% soluble starch at 30° C. overnight. Activity band of the fungal lyase was revealed by staining with $I_2$/KI solution.

B. 1.4 Results

B. 1.4.1 Purification, Molecular Mass and Isoelectric Point of the α-1,4-glucan Lyase The fungal lyase was found to adsorb on columns packed with β-cyclodextrin Sepharose, starches and Red Sepharose. Columns packed with β-cyclodextrin Sepharose 4B gel and starches were used for purification purposes.

The lyase preparation obtained by this step contained only minor contaminating proteins having a molecular mass higher than the fungal lyase. The impurity was either removed by ion exchange chromatography on Mono Q HR 5/5 or more efficiently by gel filtration on Superose 12.

The purified enzyme appeared colourless and showed no absorbance in the visible light region. The molecular mass was determined to 110 kDa as estimated on SDS-PAGE.

The purified fungal lyase showed a isoelectric point of pI 5.4 determined by isoelectric focusing on gels with a pH gradient of 3 to 9. In the native electrophoresis gels, the enzyme appeared as one single band. This band showed starch-degrading activity as detected by activity staining. Depending the age of the culture from which the enzyme is extracted, the enzyme on the native and isoelectric focusing gels showed either as a sharp band or a more diffused band with the same migration rate and pI.

B. 1.4.2 The pH and Temperature Optimum of the Fungal Lyase Catalayzed Reaction

The pH optimum pH range for the fungal lyase catalyzed reaction was found to be between pH 5 and pH 7.

B. 1.4.3 Substrate Specificity

The purified fungal lyase degraded maltosaccharides from maltose to maltoheptaose. However, the degradation rates varied. The highest activity achieved was with maltotetraose (activity as 100%), followed by maltohexaose (97%), maltoheptaose (76%), maltotriose (56%) and the lowest activity was observed with maltose (2%).

Amylopectin, amylose and glycogen were also degraded by the fungal lyase (% will be determined). The fungal lyase was an exo-lyase, not a endolyase as it degraded p-nitrophenyl α-D-maltoheptaose but failed to degrade reducing end blocked p-nitrophenyl α-D-maltoheptaose.

B. 1.5 *Morchella Vulgaris*

The protocols for the enzyme purification and charaterisation of alpha α-1,4-glucal lyase obtained from *Morchella Vulgaris* were the same as those above for *Morchella Costata* (with similar results).

B. 2. Amino Acid Sequencing of the α-1,4-glucan Lyase from Fungus

B. 2.1 Amino Acid Sequencing of the Lyases

The lyases were digested with either endoproteinase Arg-C from *Clostridium histolyticum* or endoproteinase Lys-C from *Lysobacter enzymogenes*, both sequencing grade purchased from Boehringer Mannheim, Germany. For digestion with endoproteinase Arg-C, freezedried lyase (0.1 mg) was dissolved in 50 μl 10 M urea, mM methylamine, 0.1 M Tris-HCl, pH 7.6. After overlay with $N_2$ and addition of 10 μl of 50 mM DTT and 5 mM EDTA the protein was denatured and reduced for min at 50° C. under $N_2$.

Subsequently, 1 μg of endoproteinase Arg-C in 10 μl of 50 mM Tris-HCl, pH 8.0 was added, $N_2$ was overlayed and the digestion was carried out for 6 h at 37° C.

For subsequent cysteine derivatization, 12.5 μl 100 mM iodoacetamide was added and the solution was incubated for 15 min at RT in the dark under $N_2$.

For digestion with endoproteinase Lys-C, freeze dried lyase (0.1 mg) was dissolved in 50 μl of 8 M urea, 0.4 M $NH_4HCO_3$, pH 8.4. After overlay with $N_2$ and addition of 5 μl of 45 mM DTT, the protein was denatured and reduced for 15 min at 50° C. under $N_2$. After cooling to RT, 5 μl of 100 mM iodoacetamide was added for the cysteines to be derivatized for 15 min at RT in the dark under $N_2$. Subsequently, 90 μl of water and 5 μg of endoproteinase Lys-C in 50 μl of 50 mM tricine and 10 mM EDTA, pH 8.0, was added and the digestion was carried out for 24 h at 37° C. under $N_2$.

The resulting peptides were separated by reversed phase HPLC on a VYDAC C18 column (0.46×15 cm; 10 μm; The Separations Group; California) using solvent A: 0.1% TFA in water and solvent B: 0.1% TFA in acetonitrile. Selected peptides were rechromatographed on a Develosil C18 column (0.46×10 cm; 3 μm; Dr. Ole Schou, Novo Nordisk, Denmark) using the same solvent system prior to sequencing on an Applied Biosystems 476A sequencer using pulsed-liquid fast cycles.

The amino acid sequence information from the enzyme derived from the fungus *Morchella costata* is shown FIG. 17.

The amino acid sequence information from the enzyme derived from the fungus *Morchella vulgaris* is shown FIG. 18.

B.3. DNA Sequencing of Genes Coding for the α-1,4glucan Lyase from Fungus

B.3.1 Methods for Molecular Biology

DNA was isolated as described by Dellaporte et al (1983—Plant Mol Biol Rep vol 1 pp19–21).

B.3.2 PCR

The preparation of the relevant DNA molecule was done by use of the Gene Amp DNA Amplification Kit (Perkin Elmer Cetus, USA) and in accordance with the manufactures instructions except that the Taq polymerase was added later (see PCR cycles) and the temperature cycling was changed to the following:

| no of cycles | C | time (min.) |
|---|---|---|
| PCR cycles: | | |
| 1 | 98 | 5 |
| | 60 | 5 |
| addition of Taq polymerase and oil | | |
| 35 | 94 | 1 |
| | 47 | 2 |
| | 72 | 3 |
| 1 | 72 | 20 |

B.3.3 Cloning of PCR Fragments

PCR fragments were cloned into pT7Blue (from Novagen) following the instructions of the supplier.

B.3.4 DNA Sequencing

Double stranded DNA was sequenced essentially according to the dideoxy method of Sanger et al. (1979) using the Auto Read Sequencing Kit (Pharmacia) and the Pharmacia LKB A.L.F.DNA sequencer. (Ref: Sanger, F., Nicklen, S. and Coulson, A. R.(1979). DNA sequencing with chain-determinating inhibitors. Proc. Natl. Acad. Sci. USA 74: 5463–5467.)

B.3.5 Screening of the Libraries

Screening of the Lambda Zap libraries obtained from Stratagene, was performed in accordance with the manufacturer's instructions except that the prehybridization and hybridization was performed in 2×SSC, 0.1% SDS, 10×Denhardt's and 100µg/ml denatured salmon sperm DNA.

To the hybridization solution a 32P-labeled denatured probe was added. Hybridization was performed over night at 55° C. The filters were washed twice in 2×SSC, 0.1% SDS and twice in 1×SSC, 0.1% SDS.

B.3.6 Probe

The cloned PCR fragments were isolated from the p77 blue vector by digestion with appropriate restriction enzymes. The fragments were separated from the vector by agarose gel electrophoresis and the fragments were purified from the agarose by Agarase (Boehringer Mannheim). As the fragments were only 90–240 bp long the isolated fragments were exposed to a ligation reaction before labelling with 32P-dCTP using either Prime-It random primer kit (Stratagene) or Ready to Go DNA labelling kit (Pharmacia).

B.3.7 Results

B.3.7.1 Generation of PCR DNA Fragments Coding for α-1,4-glucan Lyase

The amino acid sequences (shown below) of three overlapping tryptic peptides from α-1,4-glucan lyase were used to generate mixed oligonucleotides, which could be used as PCR primers for amplification of DNA isolated from both MC and MV.

were combined to form the sequence shown in FIG. 14 (see below). For MV the two clones could be combined to form the sequence shown in FIG. 15 in the manner described above.

An additional PCR was performed to supplement the MC clone with PstI, PvuII, AscI and NcoI restriction sites immediately in front of the ATG start codon using the following oligonucleotide as an upstream primer: AAACTGCAGCTGGCGCGCC<u>ATGG</u>CAGGATITCTGAT and a primer containing the complement sequence of bp 1297–1318 in FIG. 4 was used as a downstream primer.

The complete sequence for MC was generated by cloning the 5' end of the gene as a BglII-EcoRI fragment from one of the genomic clone (first clone) into the BamHI-EcoRI sites of pBluescript II KS+ vector from Stratagene. The 3' end of the gene was then cloned into the modified pBluescript II KS+ vector by ligating an NspV (blunt ended, using the DNA blunting kit from Amersham International)-EcoRI fragment from the other genomic clone (second clone) after the modified pBluescript II KS+ vector had been digested with EcoRI and EcoRV. Then the intermediate part of the gene was cloned in to the further modified pBluescript II KS+ vector as an EcoRI fragment from the first clone by ligating that fragment into the further modified pBluescript II KS+ vector digested with EcoRI.

B.4. Expression of the GL Gene in Micro-organisms

The DNA sequence encoding the GL can be introduced into microorganisms to produce the enzyme with high specific activity and in large quantities.

```
Lys Asn Leu His Pro Gln His Lys Met Leu Lys Asp Thr Val Leu Asp Ile Val Lys

Pro Gly His Gly Glu Tyr Val Gly Trp Gly Glu Met Gly Gly Ile Gln Phe Met Lys

Glu Pro Thr Phe Met Asn Tyr Phe Asn Phe Asp Asn Met Gln Tyr Gln Gln Val Tyr

Ala Gln Gly Ala Leu Asp Ser Arg Glu Pro Leu Tyr His Ser Asp Pro Phe Tyr
```

In the first PCR amplification primers A1/A2 (see below) were used as upstream primers and primers B1/B2 (see below) were used as downstream primer.

In this regard, the MC gene (FIG. 14) was cloned as a XbaI-XhoI blunt ended (using the DNA blunting kit from Amersham International) fragment into the Pichia expres-

```
Primer A1:  CA(GA)CA(CT)AA(GA)ATGCT(GATC)AA(GA)GA(CT)AC

Primer A2:  CA(GA)CA(CT)AA(GA)ATGTT(GA)AA(GA)GA(CT)AC

Primer B1:  TA(GA)AA(GATC)GG(GA)TC(GA)CT(GA)TG(GA)TA

Primer B2:  TA(GA)AA(GATC)GG(GA)TC(GATC)GA(GA)TG(GA)TA
```

The PCR products were analysed on a 2% LMT agarose gel and fragments of the expected sizes were cut out from the gel and treated with Agarase (Boehringer Manheim) and cloned into the pT7blue Vector (Novagen) and sequenced.

The cloned fragments from the PCR amplification coded for amino acids corresponding to the sequenced peptides (see above) and in each case in addition to two intron sequences. For MC the PCR amplified DNA sequence corresponds to the sequence shown as from position 1202 to position 1522 with reference to FIG. 14. For MV the PCR amplified DNA sequence corresponds to the sequence shown as from position 1218 to position 1535 with reference to FIG. 15.

B.3.7.2 Screening of the Genomic Libraries with the Cloned PCR Fragments

Screening of the libraries with the above-mentioned clone gave two clones for each source. For MC the two clones sion vector pHIL-D2 (containing the AOX1 promoter) digested with EcoRI and blunt ended (using the DNA blunting kit from Amersham International) for expression in *Pichia pastoris* (according to the protocol stated in the Pichia Expression Kit supplied by Invitrogen).

In another embodiment, the MC gene 1 (same as FIG. 14 except that it was modified by PCR to introduce restriction sites as described above) was cloned as a PvuII-XhoI blunt ended fragment (using the DNA blunting kit from Amersham International) into the Aspergillus expression vector pBARMTE1 (containing the methyl tryptophan resistance promoter from *Neuropera crassa*) digested with SmaI for expression in *Aspergillus niger* (Pall et al (1993) Fungal Genet Newslett. vol 40 pages 59–62). The protoplasts were prepared according to Daboussi et al (Curr Genet (1989) vol 15 pp 453–456) using lysing enzymes Sigma L-2773 and the lyticase Sigma L-8012. The transformation of the protoplasts was followed according to the protocol stated by Buxton et al (Gene (1985) vol 37 pp 207–214) except that for plating the transformed protoplasts the protocol laid out in Punt et al (Methods in Enzymology (1992) vol 216 pp 447–457) was followed but with the use of 0.6% osmotic stabilised top agarose.

The results showed that lyase activity was observed in the transformed *Pichia pastoris* and *Aspergillus niger*.

Analyses of Pichia Lyase Transportations and Aspergillus Lyase Transformants

General Methods

Preparation of Cell-free Extracts

The cells were harvested by centrifugation at 9000 rpm for 5 min and washed with 0.9% NaCl and resuspended in the breaking buffer (50 mM K-phosphate, pH 7.5 containing 1 mM of EDTA, and 5% glycerol). Cells were broken using glass beads and vortex treatment. The breaking buffer contained 1 mM PMSF (protease inhibitor). The lyase extract (supernatant) was obtained after centrifugation at 9000 rpm for 5 min followed by centrifugation at 20,000×g for 5 min.

Assay of Lyase Activity by Alkaline 3,5-dinitrosalicylic Acid Reagent (DNS)

One volume of lyase extract was mixed with an equal volume of 4% amylopectin solution. The reaction mixture was then incubated at a controlled temperature and samples were removed at specified intervals and analyzed for AF.

The lyase activity was also analyzed using a radioactive method.

The reaction mixture contained 10 µl $^{14}$C-starch solution (1 µCi; Sigma Chemicals Co.) and 10 µl of the lyase extract. The reaction mixture was left at 25° C. overnight and was then analyzed in the usual TLC system. The radioactive AF produced was detected using an Instant Imager (Pachard Instrument Co., Inc., Meriden, Conn.).

Electrophoresis and Western Blotting

SDS-PAGE was performed using 8–25% gradient gels and the PhastSystem (Pharmacia). Western blottings was also run on a Semidry transfer unit of the PhastSystem. Primary antibodies raised against the lyase purified from the red seaweed collected at Qingdao (China) were used in a dilution of 1:100. Pig antirabbit IgG conjugated to alkaline phosphatase (Dako A/S, Glostrup, Denmark) were used as secondary antibodies and used in a dilution of 1:1000.

Part I, Analysis of the Pichia Transformants Containing the above Mentioned Construct

| MC-Lyase expressed intracellularly in *Pichia pastoris* | |
|---|---|
| Names of culture | Specific activity* |
| A18 | 10 |
| A20 | 32 |
| A21 | 8 |
| A22 | 8 |
| A24 | 6 |

*The specific activity was defined as nmol of AF produced per min per mg protein at 25° C.

Part II, The Aspergilus Transformants

Results

I. Lyase Activity was Determined after 5 days Incubation (Minimal Medium Containing 0.2% Casein Enzymatic Hydrolysate Analysis by the Alkaline 3,5-dinitrosalicylic Acid Reagent

| Lyase activity analysis in cell-free extracts | |
|---|---|
| Name of the culture | Specific activity* |
| 8.13 | 11 |
| 8.16 | 538 |
| 8.19 | 37 |

*The specific activity was defined as nmol of AF produced per min per mg protein at 25° C.

The results show that the MC-lyase was expressed intracellular in *A. niger*.

II. Lyase Activity Test by Radioactive Method

The cell-free extracts of the following cultures contained $^{14}$C labelled AF

51+, 54+, 55+, 59+, 512, 513, 514, 515, 516, 518, 519.

Figure 20:
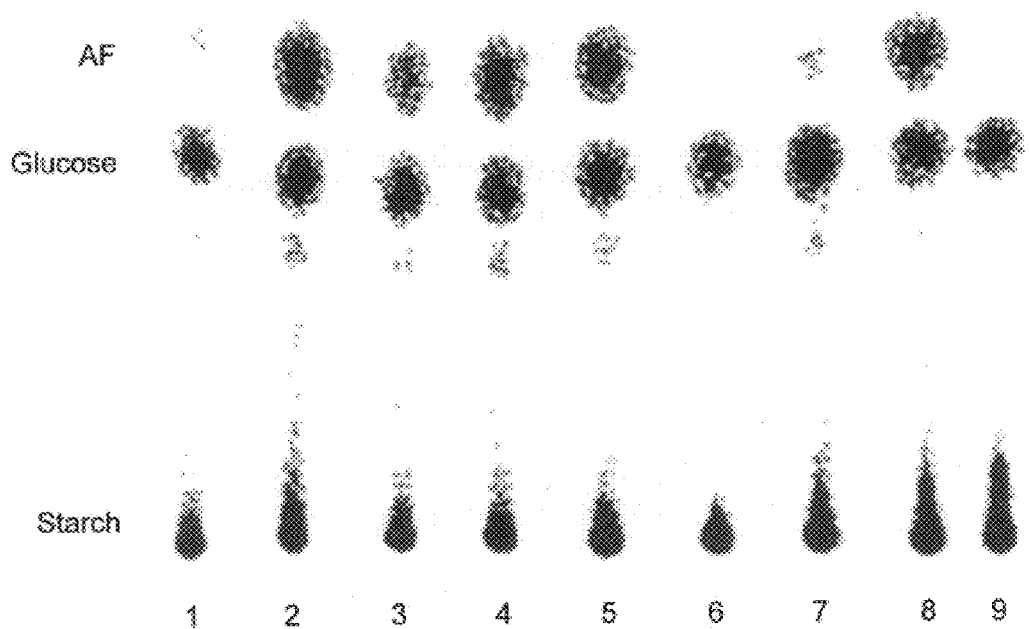

The TLC of the degradation products of the α-1,4-glucan lyase reaction using $^{14}$C-starch as substrate are shown in FIG. 20. The reaction mixture was applied on the TLC. The lane number corresponds to the name of the culture: 1, 512; 2, 513; 3, 514; 4, 515; 5, 516; 6, 517; 7, 518; 8, 519; 9, 520. The fast moving spots are AF.

C. Source=Algae Alone

The protocols for the enzyme purification and charaterisation of alpha 1,4-glucal lyase obtained from *Gracilariopsis lemaneiformis* (as obtained from Santa Cruz) were essentially the same as those described above for, for example, *Morchella Costata* (with similar results).

1. Characterization of α-1,4-glucan lyase from the parasite-free red seaweed *Gracilariopsis lemaneiformis* collected in California.

The amino acid composition of the lyase is given in the following table.

| Amino acid residues | mol % of each residue |
|---|---|
| Asx | 15.42 |
| Thr | 5.24 |
| Ser | 6.85 |
| Glx | 9.46 |
| Pro | 5.46 |
| Gly | 9.08 |
| Ala | 5.38 |
| 1/2 Cys | 1.57 |
| Val | 6.60 |
| Met | 2.90 |
| Ile | 3.66 |
| Leu | 6.00 |
| Tyr | 6.00 |
| Phe | 4.37 |
| His | 1.65 |
| Lys | 4.44 |
| Arg | 4.17 |
| Trp | 1.75 |
| Total: | 100.00 |

2. Sequence Analsis

Comparison of the peptide sequences from the Californian algae with the amino acid sequence from the fungally infected algae from China showed a high degree of homology (78 to 80% identity between the amino acid sequence generated from the PCR fragments and the corresponding sequences in the GL obtained from the algae from China) between the two protein sequences.

Three Oligonucleotides was generated from these two sequences from the Californian algae to generate a PCR fragment of app. 970 bp.

```
Primer 1:
ATGAC(GATC)AA(CT)TA(CT)AA(CT)TA(CT)GA(CT)AA

Primer 2:
(AG)TG(GATC)GGCATCAT(GATC)GC(GATC)GG(GATC)AC

Primer 3:
GTCAT(GA)TC(CT)TGCCA(GATC)AC(GA)AA(GA)TC
```

Primer 1 was used as the upstream primer and primer 2 was used as the downstream primer in the first PCR amplification. In the second PCR amplification primer 1 was used as the upstream primer and primer 3 was used as the downstream primer. A PCR fragment of the expected size was generated and cloned into the pT7blue vector from Novagen. Three independent plasmids containing a PCR fragment were sequenced and it was seen that these three cloned PCR fragments contained the codons for peptide sequences originating from three different proteins. This indicates that there are at least three different genes coding for α-1,4-glucan lyase in the Californian algae.

3. The substrate concentration at which half of the maximal velocity rate was reached is 3.76 mg/ml for amylopectin and 3.37 mg/ml for glycogen.

4. The degradation rates of the lyase on various substrates are given below.

| Substrate | AF released (nmol) |
|---|---|
| Maltose | 657 |
| Maltotriose | 654 |
| Meltotetraose | 670 |
| Maltopentaose | 674 |
| Maltohexaose | 826 |
| Maltoheptaose | 865 |
| Dextrin 20 | 775 |
| Dextrin 15 | 775 |
| Dextrin 10 | 844 |
| Amylopectin | 732 |
| Glycogen | 592 |

Reaction conditions: The reaction mixture contained 10 mM of HOAc-NaOAc (pH 3.8). The substrate concentration was 10 mg/ml. The final volume was 100 ul after the addition of lyase and water. The reaction time was 40 min at 45° C.

The lyase was not able to degrade pullulan, nigeran tetrasaccharide, trehalose, isomaltose, glucose, α-, β- and r-cyclodextrins. The lyase degraded panose and nigerose though at a slow rate.

5. The temperature optimum for the lyase was 48° C. when amylopectin was used as substrate and 50° C. when glycogen was used as substrate. At 50° C., the reactivity of glycogen was similar to that of amylopectin; below 50° C., amylopectin was a better substrate than glycogen.

6. The pH optimum range for the lyase was between pH 3.5 and pH 7.0; the optimal pH was 3.8. The buffers used in the pH tests were glycine-HCl (pH 2.2–3.6); NaOAc-HOAc (pH 3.5–5.5); Mes-NaOH (pH 5.5–6.7); Mops-NaOH (pH 6.0–8.0) and bicine-NaOH (pH 7.6–9.0). All buffers used were 40 mM.

7. At a final concentration of 2 mM, p-chloromercuribenzoic acid (PCMB) inhibited the lyase activity by 96%, indicating the —SH group(s) is essential for the enzymatic activity.

7. Further Studies 7.1 Effect of Alcohols in Increasing the Activity and Stability of the Lyase Purified from the Fungal Infected Algae 1-propanol, 2-propanol and 1-butanol were tested at the following concentrations (0%, 1%, 5% and 10%). The optimal concentration of l-propanol was 5% which increased the AF yield by 34% after 6 days of incubation; the optimal concentration for 2-propanol was 1% which increased the AF yield by 20% after 10 days incubation; the optimal concentration for 1-butanol was 5% which increased the AF yield by 52% after 3-day incubation.

Ethanol was tested at the following concentrations (0, 1, 3, 5, 7, 9, 11, 13, 15%). The optimal concentration for 7 days incubation was 5% which increased the AF yield by 12%. For 10 days incubation the optimal concentration was 3% which increased AF yield by 16%.

| The effect of 1-propanol: | | | | | |
|---|---|---|---|---|---|
| 1-propanol concentraction | | Reaction time (days) | | | |
| (v/v) | 0 | 1 | 3 | 6 | 10 |
| | | AF yield ($\mu$mol) | | | |
| 0% | 0 | 84 | 261 | 451 | 689 |
| 1% | 0 | 80 | 280 | 530 | 803 |
| 5% | 0 | 115 | 367 | 605 | 853 |
| 10% | 0 | 107 | 307 | 456 | 583 |

7.2 Effect of Different Reaction Media Upon the Production of AP by the Lyase Purified from the Fungal Infected Algae and the Fugnal Lyase from M. costata and M. vulgaris 2.1. The Lyase from the Fungal Infected Algae The results (see table below) indicate that the best reaction medium is 5 mM of HOAc-NaOAc (pH 3.9) (BACE for short) and containing mM concentrations of $Na_2$-EDTA. The production of AF using either pure water or 0.85% NaCl as reaction medium decreased the yield. Inclusion of 0.85% of NaCl in BACE also decreased the AF yield.

| Reaction Media | | Reaction Time (days) | | |
|---|---|---|---|---|
| | 0 | 1 | 3 | 8 |
| | | AF yield ($\mu$mol) | | |
| BACE | 0 | 229 | 498 | 575 |
| Water | 0 | 46 | 128 | 217 |
| NaCl (0.85%) | 0 | 123 | 239 | 249 |
| BACE + NaCl (0.85%) | 0 | 153 | 281 | 303 |

2.2. The Following Buffers: Mes-NaOH, Mops-NaOH, Hepes-NaOH, and Bicine-NaOH were the Optimal Reaction Media for the Lyase from M. costata and M. vulgaris. In the HOAc-NaOAc Buffer, the Lyase was Unstable and Therefore Use of this Buffer System caused a Decrease in AF Yield 7.3. The Effect of Endoamylases and Debranching Enzymes Upon the AF Production 3.1. The Effect of Endoamylase The starch used for AF production may first be liquified either by endoamylases, or by acid hydrolysis.

Endoamylase degraded starch is more suitable as substrate for the lyase as compared to native starch. Starch has a limited solubility at the temperature used for the lyase-catalyzed reaction. Treatment of starch with endoamylases led to increased glucose yield. It was found that a reducing matter of around 10–15% (on a dry mater basis) was most suitable as substrate for the lyase with respect to AF yield and further treatment with the endoamylase to a reducing matter of 19% was no longer suitable for the lyase.

3.2. The Effect of Pullulanase and Isoamylase

As seen from the results below, both the isoamylase and the pullulanase increased AF yield by up to 50% at pH 4.5 and 5.0. The reaction system consisted of the lyase from the fungal affected red algae with or without the addition of isoamylase or pullulanase (MegaZyme Ltd.). Amylopectin was used as substrate. The AF produced in the presence of only the lyase was expressed as 100%.

| The pH of the reaction medium | | | |
|---|---|---|---|
| Enzymes added | 3.5 | 4.5 | 5.0 |
| Lyase only | 100 | 100 | 100 |
| Lyase + isoamylase | 136 | 152 | 150 |
| Lyase + pullulanase | 132 | 158 | 155 |

4. The Relative Degrading Rates of the Fungal Lyase Towards Various Substrates 4.1. The Lyase from *M. costata*.

The activity observed with maltotetraose is expressed as 100%.

| Substrate concentration | 2 mg/ml | 4 mg/ml | 10 mg/ml |
|---|---|---|---|
| Maltose | 0.5 | 1.6 | 2.2 |
| Maltotriose | 40.6 | 58.6 | 56.0 |
| Maltotetraose | 100 | 100 | 100 |
| Maltopentaose | 107.1 | 100.1 | 99.7 |
| Maltohexaose | 86.6 | 98.2 | 95.9 |
| Maltoheptaose | 82.2 | 81.5 | 75.7 |
| Dextrin 10* | —** | — | 68.3 |
| Dextrin 15* | — | — | 61.1 |
| Dextrin 20* | — | — | 46.6 |
| Soluble Starch | — | — | 92.9 |
| Amylopectin | — | — | 106.5 |
| glycogen | — | — | 128.5 |

*the number indicates the contents of the reducing matter on a dry weight basis.
**not determined.

4.2. The Lyase from *M. vulgaris* Lyase

The activity observed for maltotetraose is treated as 100%. The final concentration of all substrates was 10 mg ml$^{-1}$.

| Substrates | Activity (%) |
|---|---|
| Maltose | 10.1 |
| Maltotriose | 49.8 |
| Maltotetraose | 100.0 |
| Maltopentaose | 79.3 |
| Maltohexaose | 92.4 |
| Maltoheptaose | 73.9 |
| Dextrin 10 | 62 |
| Dextrin 15 | 45 |
| Dextrin 20 | 37 |
| Soluble starch | 100.5 |
| Amylopectin | 139.9 |
| Glycogen | 183.3 |

The lyase from *M. costata* and *M. vulgaris* was unable to degrade the following sugars.

Trehalose, panose, nigerose, nigerotetraose, glucose, isomaltose, alpha-, beta and gama-cyclodextrins, pullulalans and non-reducing end blocked p-nitrophenyl α-D-maltoheptaoside as there was no AF detectable on a TLC plates after these substrates had been incubated for 48 h with the fungal lyase.

7.5. pH and Temperature Optimum for the Lyase Catalyzed Reaction.

| GL sources | Optimal pH | Optimal pH range | Optimal temperature |
|---|---|---|---|
| *M. costata* | 6.5 | 5.5–7.5 | 37 C.; 40 C.[a] |
| *M. vulgaris* | 6.4 | 5.9–7.6 | 43 C.; 48 C.[a] |
| Fungal infected *Gracilariopsis lemaneiformis* | 3.8 | 3.7–4.1 | 40 C.; 45 C.[a] |

[a]Parameters determined using glycogen as substrate; other parameters determined using amylopectin as substrate.

7.6. The Stabilizing Effect of Glycogen on the Lyase from the Fungal Infected *Gracilariopsis lemaneiformis*

The results indicate that at higher temperatures the reaction rates were higher when glycogen was used as substrate instead of amylopectin.

| | Reaction temperature | | |
|---|---|---|---|
| Substrates | 25 C. | 30 C. | 45 C. |
| Amylopectin | 0.818[a] | 1.133[a] | 1.17[a] |
| Glycogen | 0.592[a] | 0.904[a] | 1.861[a] |
| The ratio of relative reaction rates between Glycogen and Amylopectin (%) | | | |
| | 72.4 | 79.8 | 158.9 |

[a]the relative reaction rates.

7.7. The Molecular Masses and pI Values of the Lyases

The molecular masses of the lyases from the fungal infected *G. lemaneiformis*, both forms of lyase from apparent fungal free *G. lemaneiformis*, from *M. costata* and *M. vulgans* were estimated to 110,000±10,000 daltons used SDS-PAGE on a gradient gel (8–25%).

The pI of the lyase from the fungal infected *G. lemaneiformis* was around 3.9. For the lyase from *M. vuglaris*, the pI was around pH 4.6 and the pI for the lyase from *M. costata* was around 5.0. These values were obtained by isoelectric focusing on a gel with a pH gradient from 3 to 9.

The pI values deduced from the amino acid compositions are: The lyase from the fungal infected *G. lemaneiformis*: 4.58 and for the lyase from *M. costata*: 6.30.

7.8. Immunological Test of the Lyase by Western Blotting

The results showed that the antibodies to the algal lyase could recognize the fungal lyase both in cell-free extracts and in purified form, as revealed by Western blottings. The antibodies to the algal lyase purified form the algae collected from China also recognized the lyase from the algae collected from Sant Cruz, Calif.

| GL sources | Reactivity with the antibodies against the GL from the fungal infected *G. lemaneiformis* |
|---|---|
| Fungal infected *G. lemaneiformis* | Strong |
| *G. lemaneiformis* from Califonia both form of GL | Strong |
| *M. costata* | medium |
| *M. vulgaris* | medium |

7.9. Reversible and Irreversible Inhibitors of the Fungal Lyase

9.1. The Reversible Inhibitors, Glucose and Maltose

At a substrate concentration of 10 mg/ml, the activity for the *M. costata* lyase decreased by 19.3% in the presence of 0.1 M glucose when amylopectin was used as substrate; the activity was not affected when glycogen was used as substrate. In the presence of 0.1 M of maltose the activity decreased by 48.8% and 73.4%, respectively for glycogen and amylopectin.

| Substrates | Inhibitors | |
|---|---|---|
| Concentrations | Glucose | Maltose |
| Amylopectin 1% (2%) | 19.3% (7%) | 73.4% (67.2%) |
| Glycogen 1% (2%) | 0.000 (—) | 48.8% (49.7%) |

It seems that the inhibition by 0.1 M glucose is competitive as increasing the substrate from 1% to 2% decreased the inhibition from 19.3 to 7%, whereas the inhibition by 0.1 M maltose is non-competitive as the increase of substrate did not significantly affect the inhibition degree.

For the *M. vulgaris* lyase, 0.1 M glucose and maltose did also inhibit the reaction when either amylopectin or glycogen was used as substrate.

| Substrates | Glucose | Maltose |
|---|---|---|
| Amylopectin (1%) | 28% | 80% |
| Glycogen (1%) | 5% | 57% |

9.2. The Reversible Inhibitor Deoxyjirimycin

At a final substrate concentration of 2%, the activity was decreased to 10.4% for the algal lyase and the *M.costata* lyase in the presence of 25 $\mu$M of deoxyjirimycin, using amylopectin as substrate. At 100 $\mu$M, the activity of both lyases was completely lost.

9.3. Irreversible Inhibitor: PCMB

Under the same assay conditions and in the presence of 2 mM PCMB, the activity decreased by 60% for the *M. costata* lyase and 98% for the lyase from the fungal infected red algae. This means that the fungal lyase was much less sensitive to heavy metal inhibition.

7.10. Examples of Laboratory Scale Production of AF

10.1. Production of AF Using Dextrin as Substrate

The reactor contained 1000 g dextrins (obtained by treatment of starch with Termamyl to a final reducing matter of 10%) in a final volume of 4.6 liter (HOAC-NaOAC, pH 3.9, containing 5 mM $Na_2$-EDTA). The reaction was initiated by adding 3 mg lyase purified from fungal infected algae. The reaction was performed at room temperature. At day 19, another batch of lyase (4 mg) was added.

| Reaction time (days) | | | | | | |
|---|---|---|---|---|---|---|
| 0 | 1 | 7 | 13 | 19 | 24 | 31 |
| AF produced (grams) | | | | | | |
| 0 | 18 | 116 | 195 | 264 | 500 | 668 |

10.2. Using $^4$C-Starch for the Production of $^{14}$C-AF

The uniformly labelled $^{14}$C-starch (340 $\mu$Ci obtained from Sigma) was vaccum-dried to remove the ethanol it contained and then dissolved in 2 ml water. The reaction was initiated by adding 20 $\mu$l lyase purified from the fungal infected algae and 20 $\mu$l pullulanase (MegaZyme Ltd.) The reaction was performed overnight at 30° C. At the end of the reaction, the reaction mixture was filtered using a filter with a molecular mass cut off of 10,000 to remove the enzymes and unreacted starch molecules.

The filtrate was applied on a $Ca_2$ carbohydrate column (Chrompack) using a Waters HPLC. Water was used as eluent. The flow rate was 0.5 ml/min. AF was efficiently separated from glucose and maltosaccharides. The pooled AF fractions were freeze-dried and totally 140 $\mu$Ci $^{14}$C-AF was obtained.

These findings relate to an even further aspect of the present invention, namely the use of a reagent that can increase the hydrophobicity of the reaction medium (preferably an alcohol) to increase the stability and activity of the lyase according to the present invention. This increased stability leads to a increased AF yield.

Other modifications of the present invention will be apparent to those skilled in the art without departing from the scope of the invention.

---

What is claimed is:

1. A method of preparing 1,5-D-anhydrofructose comprising treating an α-1,4-glucan with a purified α-1,4-glucan lyase, said α-1,4-glucan lyase comprising an amino acid sequence selected from the group consisting of SEQ ID NO:1, SEQ ID NO:2, and SEQ ID NO:5.

2. A method according to claim 1, the treating with α-1,4-glucan lyase further comprises treating with an additional glucan-degrading reagent.

3. A method according to claim 2, wherein the α-1,4-glucan is starch and said glucan-degrading agent is a hydrolase.

4. A method according to claim 3, wherein the hydrolase is at least one of pullanase or isoamylase.

5. A method according to claim 1, wherein the α-1,4-glucan lyase is bound to a support.

6. A method according to claim 1, wherein said α-1,4-glucan lyase is isolated from an organism selected from the group consisting of a fungus, a fungally infected algae, and an algae alone.

7. A method according to claim 6, wherein said α-1,4-glucan lyase is isolated and/or further purified from the fungus, the fungally infected algae, or the algae alone using a gel that is not degraded by α-1,4-glucan lyase.

8. A method according to claim 7, wherein the gel comprises dextrin or derivatives thereof.

9. A method according to claim 1, wherein said α-1,4-glucan lyase is obtained from expression of a nucleotide sequence coding for α-1,4-glucan lyase.

10. A method according to claim 9, wherein the nucleotide sequence is a DNA sequence.

11. A method according to claim 10, wherein the DNA sequence comprises a sequence that is the same as, is complementary to, or contains any codon substitutions which still encode the same amino acid for any of those of, a sequence selected from the group consisting of SEQ ID NO:3, SEQ ID NO:4, and SEQ ID NO:7.

12. A method according to claim 3, wherein the starch is present at a concentration of about 25% by weight.

13. A method according to claim 1, wherein the α-1,4-glucan is treated with α-1,4-glucan lyase in the presence of a buffer.

14. A method according to claim 1, wherein the α-1,4-glucan is treated with α-1,4-glucan lyase in pure water.

15. A method according to claim 1, wherein the α-1,4-glucan is treated with α-1,4-glucan lyase in the absence of a co-factor.

16. A method according to claim 1, wherein α-1,4-glucan lyase is used in combination with amylopectin or dextrin.

17. A method according to claim 1, wherein the α-1,4-glucan lyase is in a dissolved form.

18. A method according to claim 3, wherein the hydrolase is a glucan hydrolase.

19. A method according to claim 6, wherein said fungus is *Morchella costata*.

20. A method according to claim 6, said fungally infected algae is *Gracilariopsis lemaneiformis*.

21. A method according to claim 6, wherein said algae is *Gracilariopsis lemaneiformis*.

22. A method according to claim 8, wherein the gel comprises a cyclodextrin.

23. A method according to claim 22, wherein the gel comprises beta-cyclodextrin.

24. A method according to claim 12, wherein the starch is used in a concentration up to about 25% by weight.

* * * * *

SEQUENCE LISTING (1) GENERAL INFORMATION:

(iii) NUMBER OF SEQUENCES: 39

(2) INFORMATION FOR SEQ ID NO: 1:

(i) SEQUENCE CHARACTERISTICS:
      (A) LENGTH: 1088 amino acids
      (B) TYPE: amino acid
      (D) TOPOLOGY: linear (ii) MOLECULE TYPE: protein (xi) SEQUENCE DESCRIPTION: SEQ ID NO: 1:

Met Phe Ser Thr Leu Ala Phe Val Ala Pro Ser Ala Leu Gly Ala Ser
1          5               10              15

-continued

```
Thr Phe Val Gly Ala Glu Val Arg Ser Asn Val Arg Ile His Ser Ala
             20                  25                  30
Phe Pro Ala Val His Thr Ala Thr Arg Lys Thr Asn Arg Leu Asn Val
             35                  40                  45
Ser Met Thr Ala Leu Ser Asp Lys Gln Thr Thr Ala Gly Ser Thr
 50                  55                  60
Asp Asn Pro Asp Gly Ile Asp Tyr Lys Thr Tyr Asp Tyr Val Gly Val
 65                  70                  75                  80
Trp Gly Phe Ser Pro Leu Ser Asn Thr Asn Trp Phe Ala Ala Gly Ser
                 85                  90                  95
Ser Thr Pro Gly Gly Ile Thr Asp Trp Thr Ala Thr Met Asn Val Asn
            100                 105                 110
Phe Asp Arg Ile Asp Asn Pro Ser Ile Thr Val Gln His Pro Val Gln
            115                 120                 125
Val Gln Val Thr Ser Tyr Asn Asn Ser Tyr Arg Val Arg Phe Asn
            130                 135                 140
Pro Asp Gly Pro Ile Arg Asp Val Thr Arg Gly Pro Ile Leu Lys Gln
145                 150                 155                 160
Gln Leu Asp Trp Ile Arg Thr Gln Glu Leu Ser Glu Gly Cys Asp Pro
                165                 170                 175
Gly Met Thr Phe Thr Ser Glu Gly Phe Leu Thr Phe Glu Thr Lys Asp
            180                 185                 190
Leu Ser Val Ile Ile Tyr Gly Asn Phe Lys Thr Arg Val Thr Arg Lys
            195                 200                 205
Ser Asp Gly Lys Val Ile Met Glu Asn Asp Glu Val Gly Thr Ala Ser
210                 215                 220
Ser Gly Asn Lys Cys Arg Gly Leu Met Phe Val Asp Arg Leu Tyr Gly
225                 230                 235                 240
Asn Ala Ile Ala Ser Val Asn Lys Asn Phe Arg Asn Asp Ala Val Lys
                245                 250                 255
Gln Glu Gly Phe Tyr Gly Ala Gly Glu Val Asn Cys Lys Tyr Gln Asp
            260                 265                 270
Thr Tyr Ile Leu Glu Arg Thr Gly Ile Ala Met Thr Asn Tyr Asn Tyr
            275                 280                 285
Asp Asn Leu Asn Tyr Asn Gln Trp Asp Leu Arg Pro Pro His His Asp
290                 295                 300
Gly Ala Leu Asn Pro Asp Tyr Tyr Ile Pro Met Tyr Ala Ala Pro
305                 310                 315                 320
Trp Leu Ile Val Asn Gly Cys Ala Gly Thr Ser Glu Gln Tyr Ser Tyr
                325                 330                 335
Gly Trp Phe Met Asp Asn Val Ser Gln Ser Tyr Met Asn Thr Gly Asp
            340                 345                 350
Thr Thr Trp Asn Ser Gly Gln Glu Asp Leu Ala Tyr Met Gly Ala Gln
            355                 360                 365
Tyr Gly Pro Phe Asp Gln His Phe Val Tyr Gly Ala Gly Gly Met
            370                 375                 380
Glu Cys Val Val Thr Ala Phe Ser Leu Leu Gln Gly Lys Glu Phe Glu
385                 390                 395                 400
Asn Gln Val Leu Asn Lys Arg Ser Val Met Pro Pro Lys Tyr Val Phe
                405                 410                 415
Gly Phe Phe Gln Gly Val Phe Gly Thr Ser Ser Leu Leu Arg Ala His
            420                 425                 430
```

```
Met Pro Ala Gly Glu Asn Asn Ile Ser Val Glu Glu Ile Val Glu Gly
        435                 440                 445

Tyr Gln Asn Asn Asn Phe Pro Phe Glu Gly Leu Ala Val Asp Val Asp
        450                 455                 460

Met Gln Asp Asn Leu Arg Val Phe Thr Thr Lys Gly Glu Phe Trp Thr
465                 470                 475                 480

Ala Asn Arg Val Gly Thr Gly Asp Pro Asn Asn Arg Ser Val Phe
                485                 490                 495

Glu Trp Ala His Asp Lys Gly Leu Val Cys Gln Thr Asn Ile Thr Cys
            500                 505                 510

Phe Leu Arg Asn Asp Asn Glu Gly Gln Asp Tyr Glu Val Asn Gln Thr
        515                 520                 525

Leu Arg Glu Arg Gln Leu Tyr Thr Lys Asn Asp Ser Leu Thr Gly Thr
        530                 535                 540

Asp Phe Gly Met Thr Asp Asp Gly Pro Ser Asp Ala Tyr Ile Gly His
545                 550                 555                 560

Leu Asp Tyr Gly Gly Gly Val Glu Cys Asp Ala Leu Phe Pro Asp Trp
                565                 570                 575

Gly Arg Pro Asp Val Ala Glu Trp Trp Gly Asn Asn Tyr Lys Lys Leu
            580                 585                 590

Phe Ser Ile Gly Leu Asp Phe Val Trp Gln Asp Met Thr Val Pro Ala
        595                 600                 605

Met Met Pro His Lys Ile Gly Asp Asp Ile Asn Val Lys Pro Asp Gly
610                 615                 620

Asn Trp Pro Asn Ala Asp Asp Pro Ser Asn Gly Gln Tyr Asn Trp Lys
625                 630                 635                 640

Thr Tyr His Pro Gln Val Leu Val Thr Asp Met Arg Tyr Glu Asn His
                645                 650                 655

Gly Arg Glu Pro Met Val Thr Gln Arg Asn Ile His Ala Tyr Thr Leu
            660                 665                 670

Cys Glu Ser Thr Arg Lys Glu Gly Ile Val Glu Asn Ala Asp Thr Leu
        675                 680                 685

Thr Lys Phe Arg Arg Ser Tyr Ile Ile Ser Arg Gly Gly Tyr Ile Gly
690                 695                 700

Asn Gln His Phe Gly Gly Met Trp Val Gly Asp Asn Ser Thr Thr Ser
705                 710                 715                 720

Asn Tyr Ile Gln Met Met Ile Ala Asn Asn Ile Asn Met Asn Met Ser
                725                 730                 735

Cys Leu Pro Leu Val Gly Ser Asp Ile Gly Gly Phe Thr Ser Tyr Asp
            740                 745                 750

Asn Glu Asn Gln Arg Thr Pro Cys Thr Gly Asp Leu Met Val Arg Tyr
        755                 760                 765

Val Gln Ala Gly Cys Leu Leu Pro Trp Phe Arg Asn His Tyr Asp Arg
        770                 775                 780

Trp Ile Glu Ser Lys Asp His Gly Lys Asp Tyr Gln Glu Leu Tyr Met
785                 790                 795                 800

Tyr Pro Asn Glu Met Asp Thr Leu Arg Lys Phe Val Glu Phe Arg Tyr
                805                 810                 815

Arg Trp Gln Glu Val Leu Tyr Thr Ala Met Tyr Gln Asn Ala Ala Phe
            820                 825                 830

Gly Lys Pro Ile Ile Lys Ala Ala Ser Met Tyr Asn Asn Asp Ser Asn
        835                 840                 845

Val Arg Arg Ala Gln Asn Asp His Phe Leu Leu Gly Gly His Asp Gly
```

```
                850               855                860
Tyr Arg Ile Leu Cys Ala Pro Val Val Trp Glu Asn Ser Thr Glu Arg
865                 870                875                880

Glu Leu Tyr Leu Pro Val Leu Thr Gln Trp Tyr Lys Phe Gly Pro Asp
                885                890                895

Phe Asp Thr Lys Pro Leu Glu Gly Ala Met Asn Gly Gly Asp Arg Ile
                900                905                910

Tyr Asn Tyr Pro Val Pro Gln Ser Glu Ser Pro Ile Phe Val Arg Glu
                915                920                925

Gly Ala Ile Leu Pro Thr Arg Tyr Thr Leu Asn Gly Glu Asn Lys Ser
930                 935                940

Leu Asn Thr Tyr Thr Asp Glu Asp Pro Leu Val Phe Glu Val Phe Pro
945                 950                955                960

Leu Gly Asn Asn Arg Ala Asp Gly Met Cys Tyr Leu Asp Asp Gly Gly
                965                970                975

Val Thr Thr Asn Ala Glu Asp Asn Gly Lys Phe Ser Val Val Lys Val
                980                985                990

Ala Ala Glu Gln Asp Gly Gly Thr Glu Thr Ile Thr Phe Thr Asn Asp
                995                1000               1005

Cys Tyr Glu Tyr Val Phe Gly Gly Pro Phe Tyr Arg Val Arg Gly
                1010                1015                1020

Ala Gln Ser Pro Ser Asn Ile His Val Ser Ser Gly Ala Gly Ser Gln
1025                1030                1035                1040

Asp Met Lys Val Ser Ser Ala Thr Ser Arg Ala Ala Leu Phe Asn Asp
                1045                1050                1055

Gly Glu Asn Gly Asp Phe Trp Val Asp Gln Glu Thr Asp Ser Leu Trp
                1060                1065                1070

Leu Lys Leu Pro Asn Val Val Leu Pro Asp Ala Val Ile Thr Ile Thr
                1075                1080                1085

(2) INFORMATION FOR SEQ ID NO: 2:

(i) SEQUENCE CHARACTERISTICS:
        (A) LENGTH: 1091 amino acids
        (B) TYPE: amino acid
        (D) TOPOLOGY: linear (ii) MOLECULE TYPE: protein (xi) SEQUENCE DESCRIPTION: SEQ ID NO: 2:

Met Tyr Pro Thr Leu Thr Phe Val Ala Pro Ser Ala Leu Gly Ala Arg
1                 5                  10                 15

Thr Phe Thr Cys Val Gly Ile Phe Arg Ser His Ile Leu Ile His Ser
                20                 25                 30

Val Val Pro Ala Val Arg Leu Ala Val Arg Lys Ser Asn Arg Leu Asn
                35                 40                 45

Val Ser Met Ser Ala Leu Phe Asp Lys Pro Thr Ala Val Thr Gly Gly
50                 55                 60

Lys Asp Asn Pro Asp Asn Ile Asn Tyr Thr Thr Tyr Asp Tyr Val Pro
65                 70                 75                 80

Val Trp Arg Phe Asp Pro Leu Ser Asn Thr Asn Trp Phe Ala Ala Gly
                85                 90                 95

Ser Ser Thr Pro Gly Asp Ile Asp Asp Trp Thr Ala Thr Met Asn Val
                100                105                110

Asn Phe Asp Arg Ile Asp Asn Pro Ser Phe Thr Leu Glu Lys Pro Val
                115                120                125
```

```
Gln Val Gln Val Thr Ser Tyr Lys Asn Asn Cys Phe Arg Val Arg Phe
    130                 135                 140
Asn Pro Asp Gly Pro Ile Arg Asp Val Asp Arg Gly Pro Ile Leu Gln
145                 150                 155                 160
Gln Gln Leu Asn Trp Ile Arg Lys Gln Glu Gln Ser Lys Gly Phe Asp
                165                 170                 175
Pro Lys Met Gly Phe Thr Lys Glu Gly Phe Leu Lys Phe Glu Thr Lys
            180                 185                 190
Asp Leu Asn Val Ile Ile Tyr Gly Asn Phe Lys Thr Arg Val Thr Arg
        195                 200                 205
Lys Arg Asp Gly Lys Gly Ile Met Glu Asn Asn Glu Val Pro Ala Gly
    210                 215                 220
Ser Leu Gly Asn Lys Cys Arg Gly Leu Met Phe Val Asp Arg Leu Tyr
225                 230                 235                 240
Gly Thr Ala Ile Ala Ser Val Asn Glu Asn Tyr Arg Asn Asp Pro Asp
                245                 250                 255
Arg Lys Glu Gly Phe Tyr Gly Ala Gly Glu Val Asn Cys Glu Phe Trp
            260                 265                 270
Asp Ser Glu Gln Asn Arg Asn Lys Tyr Ile Leu Glu Arg Thr Gly Ile
        275                 280                 285
Ala Met Thr Asn Tyr Asn Tyr Asp Asn Tyr Asn Tyr Asn Gln Ser Asp
    290                 295                 300
Leu Ile Ala Pro Gly Tyr Pro Ser Asp Pro Asn Phe Tyr Ile Pro Met
305                 310                 315                 320
Tyr Phe Ala Ala Pro Trp Val Val Lys Gly Cys Ser Gly Asn Ser
                325                 330                 335
Asp Glu Gln Tyr Ser Tyr Gly Trp Phe Met Asp Asn Val Ser Gln Thr
            340                 345                 350
Tyr Met Asn Thr Gly Gly Thr Ser Trp Asn Cys Gly Glu Glu Asn Leu
        355                 360                 365
Ala Tyr Met Gly Ala Gln Cys Gly Pro Phe Asp Gln His Phe Val Tyr
    370                 375                 380
Gly Asp Gly Asp Gly Leu Glu Asp Val Val Gln Ala Phe Ser Leu Leu
385                 390                 395                 400
Gln Gly Lys Glu Phe Glu Asn Gln Val Leu Asn Lys Arg Ala Val Met
                405                 410                 415
Pro Pro Lys Tyr Val Phe Gly Tyr Phe Gln Gly Val Phe Gly Ile Ala
            420                 425                 430
Ser Leu Leu Arg Glu Gln Arg Pro Glu Gly Gly Asn Asn Ile Ser Val
        435                 440                 445
Gln Glu Ile Val Glu Gly Tyr Gln Ser Asn Asn Phe Pro Leu Glu Gly
    450                 455                 460
Leu Ala Val Asp Val Asp Met Gln Gln Asp Leu Arg Val Phe Thr Thr
465                 470                 475                 480
Lys Ile Glu Phe Trp Thr Ala Asn Lys Val Gly Thr Gly Gly Asp Ser
                485                 490                 495
Asn Asn Lys Ser Val Phe Glu Trp Ala His Asp Lys Gly Leu Val Cys
            500                 505                 510
Gln Thr Asn Val Thr Cys Phe Leu Arg Asn Asp Asn Gly Gly Ala Asp
        515                 520                 525
Tyr Glu Val Asn Gln Thr Leu Arg Glu Lys Gly Leu Tyr Thr Lys Asn
    530                 535                 540
```

```
Asp Ser Leu Thr Asn Thr Asn Phe Gly Thr Thr Asn Asp Gly Pro Ser
545                 550                 555                 560

Asp Ala Tyr Ile Gly His Leu Asp Tyr Gly Gly Gly Asn Cys Asp
            565                 570                 575

Ala Leu Phe Pro Asp Trp Gly Arg Pro Gly Val Ala Glu Trp Trp Gly
            580                 585                 590

Asp Asn Tyr Ser Lys Leu Phe Lys Ile Gly Leu Asp Phe Val Trp Gln
            595                 600                 605

Asp Met Thr Val Pro Ala Met Met Pro His Lys Val Gly Asp Ala Val
        610                 615                 620

Asp Thr Arg Ser Pro Tyr Gly Trp Pro Asn Glu Asn Asp Pro Ser Asn
625                 630                 635                 640

Gly Arg Tyr Asn Trp Lys Ser Tyr His Pro Gln Val Leu Val Thr Asp
            645                 650                 655

Met Arg Tyr Glu Asn His Gly Arg Glu Pro Met Phe Thr Gln Arg Asn
            660                 665                 670

Met His Ala Tyr Thr Leu Cys Glu Ser Thr Arg Lys Glu Gly Ile Val
            675                 680                 685

Ala Asn Ala Asp Thr Leu Thr Lys Phe Arg Arg Ser Tyr Ile Ile Ser
690                 695                 700

Arg Gly Gly Tyr Ile Gly Asn Gln His Phe Gly Gly Met Trp Val Gly
705                 710                 715                 720

Asp Asn Ser Ser Ser Gln Arg Tyr Leu Gln Met Met Ile Ala Asn Ile
                725                 730                 735

Val Asn Met Asn Met Ser Cys Leu Pro Leu Val Gly Ser Asp Ile Gly
            740                 745                 750

Gly Phe Thr Ser Tyr Asp Gly Arg Asn Val Cys Pro Gly Asp Leu Met
            755                 760                 765

Val Arg Phe Val Gln Ala Gly Cys Leu Leu Pro Trp Phe Arg Asn His
770                 775                 780

Tyr Gly Arg Leu Val Glu Gly Lys Gln Glu Gly Lys Tyr Tyr Gln Glu
785                 790                 795                 800

Leu Tyr Met Tyr Lys Asp Glu Met Ala Thr Leu Arg Lys Phe Ile Glu
                805                 810                 815

Phe Arg Tyr Arg Trp Gln Glu Val Leu Tyr Thr Ala Met Tyr Gln Asn
            820                 825                 830

Ala Ala Phe Gly Lys Pro Ile Ile Lys Ala Ala Ser Met Tyr Asp Asn
            835                 840                 845

Asp Arg Asn Val Arg Gly Ala Gln Asp Asp His Phe Leu Leu Gly Gly
850                 855                 860

His Asp Gly Tyr Arg Ile Leu Cys Ala Pro Val Val Trp Glu Asn Thr
865                 870                 875                 880

Thr Ser Arg Asp Leu Tyr Leu Pro Val Leu Thr Lys Trp Tyr Lys Phe
                885                 890                 895

Gly Pro Asp Tyr Asp Thr Lys Arg Leu Asp Ser Ala Leu Asp Gly Gly
            900                 905                 910

Gln Met Ile Lys Asn Tyr Ser Val Pro Gln Ser Asp Ser Pro Ile Phe
            915                 920                 925

Val Arg Glu Gly Ala Ile Leu Pro Thr Arg Tyr Thr Leu Asp Gly Ser
            930                 935                 940

Asn Lys Ser Met Asn Thr Tyr Thr Asp Lys Asp Pro Leu Val Phe Glu
945                 950                 955                 960

Val Phe Pro Leu Gly Asn Asn Arg Ala Asp Gly Met Cys Tyr Leu Asp
```

```
                    965                 970                 975
Asp Gly Gly Ile Thr Thr Asp Ala Glu Asp His Gly Lys Phe Ser Val
                980                 985                 990
Ile Asn Val Glu Ala Leu Arg Lys Gly Val Thr Thr Ile Lys Phe
                995                 1000                1005
Ala Tyr Asp Thr Tyr Gln Tyr Val Phe Asp Gly Pro Phe Tyr Val Arg
    1010                1015                1020
Ile Arg Asn Leu Thr Thr Ala Ser Lys Ile Asn Val Ser Ser Gly Ala
1025                1030                1035                1040
Gly Glu Glu Asp Met Thr Pro Thr Ser Ala Asn Ser Arg Ala Ala Leu
                1045                1050                1055
Phe Ser Asp Gly Gly Val Gly Gly Tyr Trp Ala Asp Asn Asp Thr Ser
                1060                1065                1070
Ser Leu Trp Met Lys Leu Pro Asn Leu Val Leu Gln Asp Ala Val Ile
                1075                1080                1085
Thr Ile Thr
    1090
```

(2) INFORMATION FOR SEQ ID NO: 3:

(i) SEQUENCE CHARACTERISTICS:
        (A) LENGTH: 3267 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 3:

```
ATGTTTTCAA CCCTTGCGTT TGTCGCACCT AGTGCGCTGG GAGCCAGTAC CTTCGTAGGG    60
GCGGAGGTCA GGTCAAATGT TCGTATCCAT TCCGCTTTTC CAGCTGTGCA CACAGCTACT   120
CGCAAAACCA ATCGCCTCAA TGTATCCATG ACCGCATTGT CCGACAAACA AACGGCTACT   180
GCGGGTAGTA CAGACAATCC GGACGGTATC GACTACAAGA CCTACGATTA CGTCGGAGTA   240
TGGGGTTTCA GCCCCCTCTC CAACACGAAC TGGTTTGCTG CCGGCTCTTC TACCCCGGGT   300
GGCATCACTG ATTGGACGGC TACAATGAAT GTCAACTTCG ACCGTATCGA CAATCCGTCC   360
ATCACTGTCC AGCATCCCGT TCAGGTTCAG GTCACGTCAT ACAACAACAA CAGCTACAGG   420
GTTCGCTTCA ACCCTGATGG CCCTATTCGT GATGTGACTC GTGGGCCTAT CCTCAAGCAG   480
CAACTAGATT GGATTCGAAC GCAGGAGCTG TCAGAGGGAT GTGATCCCGG AATGACTTTC   540
ACATCAGAAG GTTTCTTGAC TTTTGAGACC AAGGATCTAA GCGTCATCAT CTACGGAAAT   600
TTCAAGACCA GAGTTACGAG AAAGTCTGAC GGCAAGGTCA TCATGGAAAA TGATGAAGTT   660
GGAACTGCAT CGTCCGGGAA CAAGTGCCGG GGATTGATGT TCGTTGATAG ATTATACGGT   720
AACGCTATCG CTTCCGTCAA CAAGAACTTC CGCAACGACG CGGTCAAGCA GGAGGGATTC   780
TATGGTGCAG GTGAAGTCAA CTGTAAGTAC CAGGACACCT ACATCTTAGA ACGCACTGGA   840
ATCGCCATGA CAAATTACAA CTACGATAAC TTGAACTATA ACCAGTGGGA CCTTAGACCT   900
CCGCATCATG ATGGTGCCCT CAACCCAGAC TATTATATTC AATGTACTA CGCAGCACCT   960
TGGTTGATCG TTAATGGATG CGCCGGTACT TCGGAGCAGT ACTCGTATGG ATGGTTCATG  1020
GACAATGTCT CTCAATCTTA CATGAATACT GGAGATACTA CCTGGAATTC TGGACAAGAG  1080
GACCTGGCAT ACATGGGCGC GCAGTATGGA CCATTTGACC AACATTTTGT TTACGGTGCT  1140
GGGGGTGGGA TGGAATGTGT GGTCACAGCG TTCTCTCTTC TACAAGGCAA GGAGTTCGAG  1200
```

```
AACCAAGTTC TCAACAAACG TTCAGTAATG CCTCCGAAAT ACGTCTTTGG TTTCTTCCAG    1260

GGTGTTTTCG GGACTTCTTC CTTGTTGAGA GCGCATATGC CAGCAGGTGA GAACAACATC    1320

TCAGTCGAAG AAATTGTAGA AGGTTATCAA ACAACAATT TCCCTTTCGA GGGGCTCGCT     1380

GTGGACGTGG ATATGCAAGA CAACTTGCGG GTGTTCACCA CGAAGGGCGA ATTTTGGACC    1440

GCAAACAGGG TGGGTACTGG CGGGGATCCA ACAACCGAT CGGTTTTTGA ATGGGCACAT     1500

GACAAAGGCC TTGTTTGTCA GACAAATATA ACTTGCTTCC TGAGGAATGA TAACGAGGGG    1560

CAAGACTACG AGGTCAATCA GACGTTAAGG GAGAGGCAGT TGTACACGAA GAACGACTCC    1620

CTGACGGGTA CGGATTTTGG AATGACCGAC GACGGCCCCA GCGATGCGTA CATCGGTCAT    1680

CTGGACTATG GGGGTGGAGT AGAATGTGAT GCACTTTTCC CAGACTGGGG ACGGCCTGAC    1740

GTGGCCGAAT GGTGGGGAAA TAACTATAAG AAACTGTTCA GCATTGGTCT CGACTTCGTC    1800

TGGCAAGACA TGACTGTTCC AGCAATGATG CCGCACAAAA TTGGCGATGA CATCAATGTG    1860

AAACCGGATG GGAATTGGCC GAATGCGGAC GATCCGTCCA ATGGACAATA CAACTGGAAG    1920

ACGTACCATC CCCAAGTGCT TGTAACTGAT ATGCGTTATG AGAATCATGG TCGGGAACCG    1980

ATGGTCACTC AACGCAACAT TCATGCGTAT ACACTGTGCG AGTCTACTAG GAAGGAAGGG    2040

ATCGTGGAAA ACGCAGACAC TCTAACGAAG TTCCGCCGTA GCTACATTAT CAGTCGTGGT    2100

GGTTACATTG GTAACCAGCA TTTCGGGGGT ATGTGGGTGG GAGACAACTC TACTACATCA    2160

AACTACATCC AAATGATGAT TGCCAACAAT ATTAACATGA ATATGTCTTG CTTGCCTCTC    2220

GTCGGCTCCG ACATTGGAGG ATTCACCTCA TACGACAATG AGAATCAGCG AACGCCGTGT    2280

ACCGGGGACT TGATGGTGAG GTATGTGCAG GCGGGCTGCC TGTTGCCGTG GTTCAGGAAC    2340

CACTATGATA GGTGGATCGA GTCCAAGGAC CACGGAAAGG ACTACCAGGA GCTGTACATG    2400

TATCCGAATG AAATGGATAC GTTGAGGAAG TTCGTTGAAT TCCGTTATCG CTGGCAGGAA    2460

GTGTTGTACA CGGCCATGTA CCAGAATGCG GCTTTCGGAA AGCCGATTAT CAAGGCTGCT    2520

TCGATGTACA ATAACGACTC AAACGTTCGC AGGGCGCAGA ACGATCATTT CCTTCTTGGT    2580

GGACATGATG GATATCGCAT TCTGTGCGCG CCTGTTGTGT GGGAGAATTC GACCGAACGC    2640

GAATTGTACT TGCCCGTGCT GACCCAATGG TACAAATTCG GTCCCGACTT TGACACCAAG    2700

CCTCTGGAAG GAGCGATGAA CGGAGGGGAC CGAATTTACA ACTACCCTGT ACCGCAAAGT    2760

GAATCACCAA TCTTCGTGAG AGAAGGTGCG ATTCTCCCTA CCCGCTACAC GTTGAACGGT    2820

GAAAACAAAT CATTGAACAC GTACACGGAC GAAGATCCGT TGGTGTTTGA AGTATTCCCC    2880

CTCGGAAACA ACCGTGCCGA CGGTATGTGT TATCTTGATG ATGGCGGTGT GACCACCAAT    2940

GCTGAAGACA ATGGCAAGTT CTCTGTCGTC AAGGTGGCAG CGGAGCAGGA TGGTGGTACG    3000

GAGACGATAA CGTTTACGAA TGATTGCTAT GAGTACGTTT TCGGTGGACC GTTCTACGTT    3060

CGAGTGCGCG GCGCTCAGTC GCCGTCGAAC ATCCACGTGT CTTCTGGAGC GGGTTCTCAG    3120

GACATGAAGG TGAGCTCTGC CACTTCCAGG GCTGCGCTGT TCAATGACGG GGAGAACGGT    3180

GATTTCTGGG TTGACCAGGA GACAGATTCT CTGTGGCTGA AGTTGCCCAA CGTTGTTCTC    3240

CCGGACGCTG TGATCACAAT TACCTAA                                       3267
```

(2) INFORMATION FOR SEQ ID NO: 4:

(i) SEQUENCE CHARACTERISTICS:
        (A) LENGTH: 3276 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 4:

| | | | | | |
|---|---|---|---|---|---|
| ATGTATCCAA | CCCTCACCTT | CGTGGCGCCT | AGTGCGCTAG | GGGCCAGAAC | TTTCACGTGT | 60 |
| GTGGGCATTT | TTAGGTCACA | CATTCTTATT | CATTCGGTTG | TTCCAGCGGT | GCGTCTAGCT | 120 |
| GTGCGCAAAA | GCAACCGCCT | CAATGTATCC | ATGTCCGCTT | TGTTCGACAA | ACCGACTGCT | 180 |
| GTTACTGGAG | GGAAGGACAA | CCCGGACAAT | ATCAATTACA | CCACTTATGA | CTACGTCCCT | 240 |
| GTGTGGCGCT | TCGACCCCCT | CAGCAATACG | AACTGGTTTG | CTGCCGGATC | TTCCACTCCC | 300 |
| GGCGATATTG | ACGACTGGAC | GGCGACAATG | AATGTGAACT | TCGACCGTAT | CGACAATCCA | 360 |
| TCCTTCACTC | TCGAGAAACC | GGTTCAGGTT | CAGGTCACGT | CATACAAGAA | CAATTGTTTC | 420 |
| AGGGTTCGCT | TCAACCCTGA | TGGTCCTATT | CGCGATGTGG | ATCGTGGGCC | TATCCTCCAG | 480 |
| CAGCAACTAA | ATTGGATCCG | GAAGCAGGAG | CAGTCGAAGG | GGTTTGATCC | TAAGATGGGC | 540 |
| TTCACAAAAG | AAGGTTTCTT | GAAATTTGAG | ACCAAGGATC | TGAACGTTAT | CATATATGGC | 600 |
| AATTTTAAGA | CTAGAGTTAC | GAGGAAGAGG | GATGGAAAAG | GGATCATGGA | GAATAATGAA | 660 |
| GTGCCGGCAG | GATCGTTAGG | GAACAAGTGC | CGGGGATTGA | TGTTTGTCGA | CAGGTTGTAC | 720 |
| GGCACTGCCA | TCGCTTCCGT | TAATGAAAAT | TACCGCAACG | ATCCCGACAG | GAAAGAGGGG | 780 |
| TTCTATGGTG | CAGGAGAAGT | AAACTGCGAG | TTTTGGGACT | CCGAACAAAA | CAGGAACAAG | 840 |
| TACATCTTAG | AACGAACTGG | AATCGCCATG | ACAAATTACA | ATTATGACAA | CTATAACTAC | 900 |
| AACCAGTCAG | ATCTTATTGC | TCCAGGATAT | CCTTCCGACC | CGAACTTCTA | CATTCCCATG | 960 |
| TATTTTGCAG | CACCTTGGGT | AGTTGTTAAG | GGATGCAGTG | GCAACAGCGA | TGAACAGTAC | 1020 |
| TCGTACGGAT | GGTTTATGGA | TAATGTCTCC | CAAACTTACA | TGAATACTGG | TGGTACTTCC | 1080 |
| TGGAACTGTG | GAGAGGAGAA | CTTGGCATAC | ATGGGAGCAC | AGTGCGGTCC | ATTTGACCAA | 1140 |
| CATTTTGTGT | ATGGTGATGG | AGATGGTCTT | GAGGATGTTG | TCCAAGCGTT | CTCTCTTCTG | 1200 |
| CAAGGCAAAG | AGTTTGAGAA | CCAAGTTCTG | AACAAACGTG | CCGTAATGCC | TCCGAAATAT | 1260 |
| GTGTTTGGTT | ACTTTCAGGG | AGTCTTTGGG | ATTGCTTCCT | TGTTGAGAGA | GCAAAGACCA | 1320 |
| GAGGGTGGTA | ATAACATCTC | TGTTCAAGAG | ATTGTCGAAG | GTTACCAAAG | CAATAACTTC | 1380 |
| CCTTTAGAGG | GGTTAGCCGT | AGATGTGGAT | ATGCAACAAG | ATTTGCGCGT | GTTCACCACG | 1440 |
| AAGATTGAAT | TTTGGACGGC | AAATAAGGTA | GGCACCGGGG | GAGACTCGAA | TAACAAGTCG | 1500 |
| GTGTTTGAAT | GGGCACATGA | CAAAGGCCTT | GTATGTCAGA | CGAATGTTAC | TTGCTTCTTG | 1560 |
| AGAAACGACA | ACGGCGGGGC | AGATTACGAA | GTCAATCAGA | CATTGAGGGA | GAAGGGTTTG | 1620 |
| TACACGAAGA | ATGACTCACT | GACGAACACT | AACTTCGGAA | CTACCAACGA | CGGGCCGAGC | 1680 |
| GATGCGTACA | TTGGACATCT | GGACTATGGT | GGCGGAGGGA | ATTGTGATGC | ACTTTTCCCA | 1740 |
| GACTGGGGTC | GACCGGGTGT | GGCTGAATGG | TGGGGTGATA | ACTACAGCAA | GCTCTTCAAA | 1800 |
| ATTGGTCTGG | ATTTCGTCTG | GCAAGACATG | ACAGTTCCAG | CTATGATGCC | ACACAAAGTT | 1860 |
| GGCGACGCAG | TCGATACGAG | ATCACCTTAC | GGCTGGCCGA | ATGAGAATGA | TCCTTCGAAC | 1920 |
| GGACGATACA | ATTGGAAATC | TTACCATCCA | CAAGTTCTCG | TAACTGATAT | GCGATATGAG | 1980 |
| AATCATGGAA | GGGAACCGAT | GTTCACTCAA | CGCAATATGC | ATGCGTACAC | ACTCTGTGAA | 2040 |
| TCTACGAGGA | AGGAAGGGAT | TGTTGCAAAT | GCAGACACTC | TAACGAAGTT | CCGCCGCAGT | 2100 |
| TATATTATCA | GTCGTGGAGG | TTACATTGGC | AACCAGCATT | TTGGAGGAAT | GTGGGTTGGA | 2160 |
| GACAACTCTT | CCTCCCAAAG | ATACCTCCAA | ATGATGATCG | CGAACATCGT | CAACATGAAC | 2220 |
| ATGTCTTGCC | TTCCACTAGT | TGGGTCCGAC | ATTGGAGGTT | TTACTTCGTA | TGATGGACGA | 2280 |

-continued

```
AACGTGTGTC CCGGGGATCT AATGGTAAGA TTCGTGCAGG CGGGTTGCTT ACTACCGTGG    2340

TTCAGAAACC ACTATGGTAG GTTGGTCGAG GGCAAGCAAG AGGGAAAATA CTATCAAGAA    2400

CTGTACATGT ACAAGGACGA GATGGCTACA TTGAGAAAAT TCATTGAATT CCGTTACCGC    2460

TGGCAGGAGG TGTTGTACAC TGCTATGTAC CAGAATGCGG CTTTCGGGAA ACCGATTATC    2520

AAGGCAGCTT CCATGTACGA CAACGACAGA AACGTTCGCG GCGCACAGGA TGACCACTTC    2580

CTTCTCGGCG ACACGATGG ATATCGTATT TTGTGTGCAC CTGTTGTGTG GGAGAATACA     2640

ACCAGTCGCG ATCTGTACTT GCCTGTGCTG ACCAAATGGT ACAAATTCGG CCCTGACTAT    2700

GACACCAAGC GCCTGGATTC TGCGTTGGAT GGAGGGCAGA TGATTAAGAA CTATTCTGTG    2760

CCACAAAGCG ACTCTCCGAT ATTTGTGAGG GAAGGAGCTA TTCTCCCTAC CCGCTACACG    2820

TTGGACGGTT CGAACAAGTC AATGAACACG TACACAGACA AGACCCGTT GGTGTTTGAG     2880

GTATTCCCTC TTGAAACAA CCGTGCCGAC GGTATGTGTT ATCTTGATGA TGGCGGTATT     2940

ACTACAGATG CTGAGGACCA TGGCAAATTC TCTGTTATCA ATGTCGAAGC CTTACGGAAA    3000

GGTGTTACGA CGACGATCAA GTTTGCGTAT GACACTTATC AATACGTATT TGATGGTCCA    3060

TTCTACGTTC GAATCCGTAA TCTTACGACT GCATCAAAAA TTAACGTGTC TTCTGGAGCG    3120

GGTGAAGAGG ACATGACACC GACCTCTGCG AACTCGAGGG CAGCTTTGTT CAGTGATGGA    3180

GGTGTTGGAG AATACTGGGC TGACAATGAT ACGTCTTCTC TGTGGATGAA GTTGCCAAAC    3240

CTGGTTCTGC AAGACGCTGT GATTACCATT ACGTAG                              3276
```

(2) INFORMATION FOR SEQ ID NO: 5:

(i) SEQUENCE CHARACTERISTICS:
        (A) LENGTH: 1066 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Ala Gly Phe Ser Asp Pro Leu Asn Phe Cys Lys Ala Glu Asp Tyr
1               5                   10                  15

Tyr Ser Val Ala Leu Asp Trp Lys Gly Pro Gln Lys Ile Ile Gly Val
            20                  25                  30

Asp Thr Thr Pro Pro Lys Ser Thr Lys Phe Pro Lys Asn Trp His Gly
        35                  40                  45

Val Asn Leu Arg Phe Asp Asp Gly Thr Leu Gly Val Val Gln Phe Ile
    50                  55                  60

Arg Pro Cys Val Trp Arg Val Arg Tyr Asp Pro Gly Phe Lys Thr Ser
65                  70                  75                  80

Asp Glu Tyr Gly Asp Glu Asn Thr Arg Thr Ile Val Gln Asp Tyr Met
            85                  90                  95

Ser Thr Leu Ser Asn Lys Leu Asp Thr Tyr Arg Gly Leu Thr Trp Glu
            100                 105                 110

Thr Lys Cys Glu Asp Ser Gly Asp Phe Thr Phe Ser Ser Lys Val
            115                 120                 125

Thr Ala Val Glu Lys Ser Glu Arg Thr Arg Asn Lys Val Gly Asp Gly
            130                 135                 140

Leu Arg Ile His Leu Trp Lys Ser Pro Phe Arg Ile Gln Val Val Arg
145                 150                 155                 160

Thr Leu Thr Pro Leu Lys Asp Pro Tyr Pro Ile Pro Asn Val Ala Ala
                165                 170                 175
```

-continued

Ala Glu Ala Arg Val Ser Asp Lys Val Val Trp Gln Thr Ser Pro Lys
            180                 185                 190

Thr Phe Arg Lys Asn Leu His Pro Gln His Lys Met Leu Lys Asp Thr
        195                 200                 205

Val Leu Asp Ile Val Lys Pro Gly His Gly Glu Tyr Val Gly Trp Gly
    210                 215                 220

Glu Met Gly Gly Ile Gln Phe Met Lys Glu Pro Thr Phe Met Asn Tyr
225                 230                 235                 240

Phe Asn Phe Asp Asn Met Gln Tyr Gln Val Tyr Ala Gln Gly Ala
                245                 250                 255

Leu Asp Ser Arg Glu Pro Leu Tyr His Ser Asp Pro Phe Tyr Leu Asp
            260                 265                 270

Val Asn Ser Asn Pro Glu His Lys Asn Ile Thr Ala Thr Phe Ile Asp
        275                 280                 285

Asn Tyr Ser Gln Ile Ala Ile Asp Phe Gly Lys Thr Asn Ser Gly Tyr
    290                 295                 300

Ile Lys Leu Gly Thr Arg Tyr Gly Gly Ile Asp Cys Tyr Gly Ile Ser
305                 310                 315                 320

Ala Asp Thr Val Pro Glu Ile Val Arg Leu Tyr Thr Gly Leu Val Gly
            325                 330                 335

Arg Ser Lys Leu Lys Pro Arg Tyr Ile Leu Gly Ala His Gln Ala Cys
        340                 345                 350

Tyr Gly Tyr Gln Gln Glu Ser Asp Leu Tyr Ser Val Val Gln Gln Tyr
    355                 360                 365

Arg Asp Cys Lys Phe Pro Leu Asp Gly Ile His Val Asp Val Asp Val
            370                 375                 380

Gln Asp Gly Phe Arg Thr Phe Thr Thr Asn Pro His Thr Phe Pro Asn
385                 390                 395                 400

Pro Lys Glu Met Phe Thr Asn Leu Arg Asn Asn Gly Ile Lys Cys Ser
                405                 410                 415

Thr Asn Ile Thr Pro Val Ile Ser Ile Asn Asn Arg Glu Gly Gly Tyr
            420                 425                 430

Ser Thr Leu Leu Glu Gly Val Asp Lys Lys Tyr Phe Ile Met Asp Asp
        435                 440                 445

Arg Tyr Thr Glu Gly Thr Ser Gly Asn Ala Lys Asp Val Arg Tyr Met
    450                 455                 460

Tyr Tyr Gly Gly Gly Asn Lys Val Glu Val Asp Pro Asn Asp Val Asn
465                 470                 475                 480

Gly Arg Pro Asp Phe Lys Asp Asn Tyr Asp Phe Pro Ala Asn Phe Asn
                485                 490                 495

Ser Lys Gln Tyr Pro Tyr His Gly Gly Val Ser Tyr Gly Tyr Gly Asn
            500                 505                 510

Gly Ser Ala Gly Phe Tyr Pro Asp Leu Asn Arg Lys Glu Val Arg Ile
        515                 520                 525

Trp Trp Gly Met Gln Tyr Lys Tyr Leu Phe Asp Met Gly Leu Glu Phe
    530                 535                 540

Val Trp Gln Asp Met Thr Thr Pro Ala Ile His Thr Ser Tyr Gly Asp
545                 550                 555                 560

Met Lys Gly Leu Pro Thr Arg Leu Leu Val Thr Ser Asp Ser Val Thr
                565                 570                 575

Asn Ala Ser Glu Lys Lys Leu Ala Ile Glu Thr Trp Ala Leu Tyr Ser
            580                 585                 590

-continued

```
Tyr Asn Leu His Lys Ala Thr Trp His Gly Leu Ser Arg Leu Glu Ser
        595                 600                 605

Arg Lys Asn Lys Arg Asn Phe Ile Leu Gly Arg Gly Ser Tyr Ala Gly
610                 615                 620

Ala Tyr Arg Phe Ala Gly Leu Trp Thr Gly Asp Asn Ala Ser Asn Trp
625                 630                 635                 640

Glu Phe Trp Lys Ile Ser Val Ser Gln Val Leu Ser Leu Gly Leu Asn
                    645                 650                 655

Gly Val Cys Ile Ala Gly Ser Asp Thr Gly Gly Phe Glu Pro Tyr Arg
                660                 665                 670

Asp Ala Asn Gly Val Glu Glu Lys Tyr Cys Ser Pro Glu Leu Leu Ile
                675                 680                 685

Arg Trp Tyr Thr Gly Ser Phe Leu Leu Pro Trp Leu Arg Asn His Tyr
690                 695                 700

Val Lys Lys Asp Arg Lys Trp Phe Gln Glu Pro Tyr Ser Tyr Pro Lys
705                 710                 715                 720

His Leu Glu Thr His Pro Glu Leu Ala Asp Gln Ala Trp Leu Tyr Lys
                    725                 730                 735

Ser Val Leu Glu Ile Cys Arg Tyr Tyr Val Glu Leu Arg Tyr Ser Leu
                740                 745                 750

Ile Gln Leu Leu Tyr Asp Cys Met Phe Gln Asn Val Val Asp Gly Met
                755                 760                 765

Pro Ile Thr Arg Ser Met Leu Leu Thr Asp Thr Glu Asp Thr Thr Phe
770                 775                 780

Phe Asn Glu Ser Gln Lys Phe Leu Asp Asn Gln Tyr Met Ala Gly Asp
785                 790                 795                 800

Asp Ile Leu Val Ala Pro Ile Leu His Ser Arg Lys Glu Ile Pro Gly
                    805                 810                 815

Glu Asn Arg Asp Val Tyr Leu Pro Leu Tyr His Thr Trp Tyr Pro Ser
                820                 825                 830

Asn Leu Arg Pro Trp Asp Asp Gln Gly Val Ala Leu Gly Asn Pro Val
                835                 840                 845

Glu Gly Gly Ser Val Ile Asn Tyr Thr Ala Arg Ile Val Ala Pro Glu
850                 855                 860

Asp Tyr Asn Leu Phe His Ser Val Val Pro Val Tyr Val Arg Glu Gly
865                 870                 875                 880

Ala Ile Ile Pro Gln Ile Glu Val Arg Gln Trp Thr Gly Gln Gly Gly
                    885                 890                 895

Ala Asn Arg Ile Lys Phe Asn Ile Tyr Pro Gly Lys Asp Lys Glu Tyr
                900                 905                 910

Cys Thr Tyr Leu Asp Asp Gly Val Ser Arg Asp Ser Ala Pro Glu Asp
                915                 920                 925

Leu Pro Gln Tyr Lys Glu Thr His Glu Gln Ser Lys Val Glu Gly Ala
        930                 935                 940

Glu Ile Ala Lys Gln Ile Gly Lys Lys Thr Gly Tyr Asn Ile Ser Gly
945                 950                 955                 960

Thr Asp Pro Glu Ala Lys Gly Tyr His Arg Lys Val Ala Val Thr Gln
                    965                 970                 975

Thr Ser Lys Asp Lys Thr Arg Thr Val Thr Ile Glu Pro Lys His Asn
                980                 985                 990

Gly Tyr Asp Pro Ser Lys Glu Val Gly Asp Tyr Thr Ile Ile Leu
                995                 1000                1005

Trp Tyr Ala Pro Gly Phe Asp Gly Ser Ile Val Asp Val Ser Lys Thr
```

-continued

```
               1010                1015                1020

Thr Val Asn Val Glu Gly Gly Val Glu His Gln Val Tyr Lys Asn Ser
1025                1030                1035                1040

Asp Leu His Thr Val Val Ile Asp Val Lys Glu Val Ile Gly Thr Thr
                1045                1050                1055

Lys Ser Val Lys Ile Thr Cys Thr Ala Ala
                1060                1065

(2) INFORMATION FOR SEQ ID NO: 6:

(i) SEQUENCE CHARACTERISTICS:
        (A) LENGTH: 1070 amino acids
        (B) TYPE: amino acid
        (D) TOPOLOGY: linear (ii) MOLECULE TYPE: protein (xi) SEQUENCE DESCRIPTION: SEQ ID NO: 6:

Met Ala Gly Leu Ser Asp Pro Leu Asn Phe Cys Lys Ala Glu Asp Tyr
1               5                   10                  15

Tyr Ala Ala Lys Gly Trp Ser Gly Pro Gln Lys Ile Ile Arg Tyr
            20                  25                  30

Asp Gln Thr Pro Pro Gln Gly Thr Lys Asp Pro Lys Ser Trp His Ala
            35                  40                  45

Val Asn Leu Pro Phe Asp Asp Gly Thr Met Cys Val Gln Phe Val
50                  55                  60

Arg Pro Cys Val Trp Arg Val Arg Tyr Asp Pro Ser Val Lys Thr Ser
65              70                  75                  80

Asp Glu Tyr Gly Asp Glu Asn Thr Arg Thr Ile Val Gln Asp Tyr Met
                85                  90                  95

Thr Thr Leu Val Gly Asn Leu Asp Ile Phe Arg Gly Leu Thr Trp Val
                100                 105                 110

Ser Thr Leu Glu Asp Ser Gly Glu Tyr Tyr Thr Phe Lys Ser Glu Val
            115                 120                 125

Thr Ala Val Asp Glu Thr Glu Arg Thr Arg Asn Lys Val Gly Asp Gly
        130                 135                 140

Leu Lys Ile Tyr Leu Trp Lys Asn Pro Phe Arg Ile Gln Val Val Arg
145             150                 155                 160

Leu Leu Thr Pro Leu Val Asp Pro Phe Pro Ile Pro Asn Val Ala Asn
                165                 170                 175

Ala Thr Ala Arg Val Ala Asp Lys Val Val Trp Gln Thr Ser Pro Lys
            180                 185                 190

Thr Phe Arg Lys Asn Leu His Pro Gln His Lys Met Leu Lys Asp Thr
        195                 200                 205

Val Leu Asp Ile Ile Lys Pro Gly His Gly Glu Tyr Val Gly Trp Gly
210                 215                 220

Glu Met Gly Gly Ile Glu Phe Met Lys Glu Pro Thr Phe Met Asn Tyr
225                 230                 235                 240

Phe Asn Phe Asp Asn Met Gln Tyr Gln Gln Val Tyr Ala Gln Gly Ala
                245                 250                 255

Leu Asp Ser Arg Glu Pro Leu Tyr His Ser Asp Pro Phe Tyr Leu Asp
            260                 265                 270

Val Asn Ser Asn Pro Glu His Lys Asn Ile Thr Ala Thr Phe Ile Asp
        275                 280                 285

Asn Tyr Ser Gln Ile Ala Ile Asp Phe Gly Lys Thr Asn Ser Gly Tyr
        290                 295                 300
```

-continued

```
Ile Lys Leu Gly Thr Arg Tyr Gly Gly Ile Asp Cys Tyr Gly Ile Ser
305                 310                 315                 320

Ala Asp Thr Val Pro Glu Ile Val Arg Leu Tyr Thr Gly Leu Val Gly
                325                 330                 335

Arg Ser Lys Leu Lys Pro Arg Tyr Ile Leu Gly Ala His Gln Ala Cys
            340                 345                 350

Tyr Gly Tyr Gln Gln Glu Ser Asp Leu His Ala Val Val Gln Gln Tyr
        355                 360                 365

Arg Asp Thr Lys Phe Pro Leu Asp Gly Leu His Val Asp Val Asp Phe
370                 375                 380

Gln Asp Asn Phe Arg Thr Phe Thr Thr Asn Pro Ile Thr Phe Pro Asn
385                 390                 395                 400

Pro Lys Glu Met Phe Thr Asn Leu Arg Asn Asn Gly Ile Lys Cys Ser
                405                 410                 415

Thr Asn Ile Thr Pro Val Ile Ser Ile Arg Asp Arg Pro Asn Gly Tyr
            420                 425                 430

Ser Thr Leu Asn Glu Gly Tyr Asp Lys Lys Tyr Phe Ile Met Asp Asp
        435                 440                 445

Arg Tyr Thr Glu Gly Thr Ser Gly Asp Pro Gln Asn Val Arg Tyr Ser
450                 455                 460

Phe Tyr Gly Gly Gly Asn Pro Val Glu Val Asn Pro Asn Asp Val Trp
465                 470                 475                 480

Ala Arg Pro Asp Phe Gly Asp Asn Tyr Asp Phe Pro Thr Asn Phe Asn
                485                 490                 495

Cys Lys Asp Tyr Pro Tyr His Gly Gly Val Ser Tyr Gly Tyr Gly Asn
            500                 505                 510

Gly Thr Pro Gly Tyr Tyr Pro Asp Leu Asn Arg Glu Glu Val Arg Ile
        515                 520                 525

Trp Trp Gly Leu Gln Tyr Glu Tyr Leu Phe Asn Met Gly Leu Glu Phe
530                 535                 540

Val Trp Gln Asp Met Thr Thr Pro Ala Ile His Ser Ser Tyr Gly Asp
545                 550                 555                 560

Met Lys Gly Leu Pro Thr Arg Leu Leu Val Thr Ala Asp Ser Val Thr
                565                 570                 575

Asn Ala Ser Glu Lys Lys Leu Ala Ile Glu Ser Trp Ala Leu Tyr Ser
            580                 585                 590

Tyr Asn Leu His Lys Ala Thr Phe His Gly Leu Gly Arg Leu Glu Ser
        595                 600                 605

Arg Lys Asn Lys Arg Asn Phe Ile Leu Gly Arg Gly Ser Tyr Ala Gly
610                 615                 620

Ala Tyr Arg Phe Ala Gly Leu Trp Thr Gly Asp Asn Ala Ser Thr Trp
625                 630                 635                 640

Glu Phe Trp Lys Ile Ser Val Ser Gln Val Leu Ser Leu Gly Leu Asn
                645                 650                 655

Gly Val Cys Ile Ala Gly Ser Asp Thr Gly Gly Phe Glu Pro Ala Arg
            660                 665                 670

Thr Glu Ile Gly Glu Glu Lys Tyr Cys Ser Pro Glu Leu Leu Ile Arg
        675                 680                 685

Trp Tyr Thr Gly Ser Phe Leu Leu Pro Trp Leu Arg Asn His Tyr Val
690                 695                 700

Lys Lys Asp Arg Lys Trp Phe Gln Glu Pro Tyr Ala Tyr Pro Lys His
705                 710                 715                 720
```

```
Leu Glu Thr His Pro Glu Leu Ala Asp Gln Ala Trp Leu Tyr Lys Ser
                725                 730                 735

Val Leu Glu Ile Cys Arg Tyr Trp Val Glu Leu Arg Tyr Ser Leu Ile
            740                 745                 750

Gln Leu Leu Tyr Asp Cys Met Phe Gln Asn Val Val Asp Gly Met Pro
        755                 760                 765

Leu Ala Arg Ser Met Leu Leu Thr Asp Thr Glu Asp Thr Thr Phe Phe
    770                 775                 780

Asn Glu Ser Gln Lys Phe Leu Asp Asn Gln Tyr Met Ala Gly Asp Asp
785                 790                 795                 800

Ile Leu Val Ala Pro Ile Leu His Ser Arg Asn Glu Val Pro Gly Glu
                805                 810                 815

Asn Arg Asp Val Tyr Leu Pro Leu Phe His Thr Trp Tyr Pro Ser Asn
            820                 825                 830

Leu Arg Pro Trp Asp Asp Gln Gly Val Ala Leu Gly Asn Pro Val Glu
        835                 840                 845

Gly Gly Ser Val Ile Asn Tyr Thr Ala Arg Ile Val Ala Pro Glu Asp
    850                 855                 860

Tyr Asn Leu Phe His Asn Val Val Pro Val Tyr Ile Arg Glu Gly Ala
865                 870                 875                 880

Ile Ile Pro Gln Ile Gln Val Arg Gln Trp Ile Gly Glu Gly Gly Pro
                885                 890                 895

Asn Pro Ile Lys Phe Asn Ile Tyr Pro Gly Lys Asp Lys Glu Tyr Val
            900                 905                 910

Thr Tyr Leu Asp Asp Gly Val Ser Arg Asp Ser Ala Pro Asp Asp Leu
        915                 920                 925

Pro Gln Tyr Arg Glu Ala Tyr Glu Gln Ala Lys Val Glu Gly Lys Asp
    930                 935                 940

Val Gln Lys Gln Leu Ala Val Ile Gln Gly Asn Lys Thr Asn Asp Phe
945                 950                 955                 960

Ser Ala Ser Gly Ile Asp Lys Glu Ala Lys Gly Tyr His Arg Lys Val
                965                 970                 975

Ser Ile Lys Gln Glu Ser Lys Asp Lys Thr Arg Thr Val Thr Ile Glu
            980                 985                 990

Pro Lys His Asn Gly Tyr Asp Pro Ser Lys Glu Val Gly Asn Tyr Tyr
        995                 1000                1005

Thr Ile Ile Leu Trp Tyr Ala Pro Gly Phe Asp Gly Ser Ile Val Asp
    1010                1015                1020

Val Ser Gln Ala Thr Val Asn Ile Glu Gly Gly Val Glu Cys Glu Ile
1025                1030                1035                1040

Phe Lys Asn Thr Gly Leu His Thr Val Val Asn Val Lys Glu Val
            1045                1050                1055

Ile Gly Thr Thr Lys Ser Val Lys Ile Thr Cys Thr Thr Ala
        1060                1065                1070

(2) INFORMATION FOR SEQ ID NO: 7:

(i) SEQUENCE CHARACTERISTICS:
        (A) LENGTH: 3201 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 7:
```

-continued

```
ATGGCAGGAT TTTCTGATCC TCTCAACTTT TGCAAAGCAG AAGACTACTA CAGTGTTGCG    60
CTAGACTGGA AGGGCCCTCA AAAAATCATT GGAGTAGACA CTACTCCTCC AAAGAGCACC   120
AAGTTCCCCA AAAACTGGCA TGGAGTGAAC TTGAGATTCG ATGATGGGAC TTTAGGTGTG   180
GTTCAGTTCA TTAGGCCGTG CGTTTGGAGG GTTAGATACG ACCCTGGTTT CAAGACCTCT   240
GACGAGTATG GTGATGAGAA TACGAGGACA ATTGTGCAAG ATTATATGAG TACTCTGAGT   300
AATAAATTGG ATACTTATAG AGGTCTTACG TGGGAAACCA AGTGTGAGGA TTCGGGAGAT   360
TTCTTTACCT TCTCATCCAA GGTCACCGCC GTTGAAAAAT CCGAGCGGAC CCGCAACAAG   420
GTCGGCGATG GCCTCAGAAT TCACCTATGG AAAAGCCCTT TCCGCATCCA AGTAGTGCGC   480
ACCTTGACCC CTTTGAAGGA TCCTTACCCC ATTCCAAATG TAGCCGCAGC CGAAGCCCGT   540
GTGTCCGACA AGGTCGTTTG GCAAACGTCT CCCAAGACAT TCAGAAAGAA CCTGCATCCG   600
CAACACAAGA TGCTAAAGGA TACAGTTCTT GACATTGTCA AACCTGGACA TGGCGAGTAT   660
GTGGGGTGGG GAGAGATGGG AGGTATCCAG TTTATGAAGG AGCCAACATT CATGAACTAT   720
TTTAACTTCG ACAATATGCA ATACCAGCAA GTCTATGCCC AAGGTGCTCT CGATTCTCGC   780
GAGCCACTGT ACCACTCGGA TCCCTTCTAT CTTGATGTGA ACTCCAACCC GGAGCACAAG   840
AATATCACGG CAACCTTTAT CGATAACTAC TCTCAAATTG CCATCGACTT TGGAAAGACC   900
AACTCAGGCT ACATCAAGCT GGGAACCAGG TATGGTGGTA TCGATTGTTA CGGTATCAGT   960
GCGGATACGG TCCCGGAAAT TGTACGACTT TATACAGGTC TTGTTGGACG TTCAAAGTTG  1020
AAGCCCAGAT ATATTCTCGG GGCCCATCAA GCCTGTTATG GATACCAACA GGAAAGTGAC  1080
TTGTATTCTG TGGTCCAGCA GTACCGTGAC TGTAAATTTC CACTTGACGG GATTCACGTC  1140
GATGTCGATG TTCAGGACGG CTTCAGAACT TTCACCACCA ACCCACACAC TTTCCCTAAC  1200
CCCAAAGAGA TGTTTACTAA CTTGAGGAAT AATGGAATCA AGTGCTCCAC CAATATCACT  1260
CCTGTTATCA GCATTAACAA CAGAGAGGGT GGATACAGTA CCCTCCTTGA GGGAGTTGAC  1320
AAAAAATACT TTATCATGGA CGACAGATAT ACCGAGGGAA CAAGTGGGAA TGCGAAGGAT  1380
GTTCGGTACA TGTACTACGG TGGTGGTAAT AAGGTTGAGG TCGATCCTAA TGATGTTAAT  1440
GGTCGGCCAG ACTTTAAAGA CAACTATGAC TTCCCCGCGA ACTTCAACAG CAAACAATAC  1500
CCCTATCATG GTGGTGTGAG CTACGGTTAT GGGAACGGTA GTGCAGGTTT TACCCGGAC   1560
CTCAACAGAA AGGAGGTTCG TATCTGGTGG GGAATGCAGT ACAAGTATCT CTTCGATATG  1620
GGACTGGAAT TTGTGTGGCA AGACATGACT ACCCCAGCAA TCCACACATC ATATGGAGAC  1680
ATGAAAGGGT TGCCCACCCG TCTACTCGTC ACCTCAGACT CCGTCACCAA TGCCTCTGAG  1740
AAAAAGCTCG CAATTGAAAC TTGGGCTCTC TACTCCTACA ATCTCCACAA AGCAACTTGG  1800
CATGGTCTTA GTCGTCTCGA ATCTCGTAAG AACAAACGAA ACTTCATCCT CGGGCGTGGA  1860
AGTTATGCCG GAGCCTATCG TTTTGCTGGT CTCTGGACTG GGGATAATGC AAGTAACTGG  1920
GAATTCTGGA AGATATCGGT CTCTCAAGTT CTTTCTCTGG GCCTCAATGG TGTGTGCATC  1980
GCGGGGTCTG ATACGGGTGG TTTTGAACCC TACCGTGATG CAAATGGGGT CGAGGAGAAA  2040
TACTGTAGCC CAGAGCTACT CATCAGGTGG TATACTGGTT CATTCCTCTT GCCGTGGCTC  2100
AGGAACCATT ATGTCAAAAA GGACAGGAAA TGGTTCCAGG AACCATACTC GTACCCCAAG  2160
CATCTTGAAA CCCATCCAGA ACTCGCAGAC CAAGCATGGC TCTATAAATC CGTTTTGGAG  2220
ATCTGTAGGT ACTATGTGGA GCTTAGATAC TCCCTCATCC AACTACTTTA CGACTGCATG  2280
TTTCAAAACG TAGTCGACGG TATGCCAATC ACCAGATCTA TGCTCTTGAC CGATACTGAG  2340
GATACCACCT TCTTCAACGA GAGCCAAAAG TTCCTCGACA ACCAATATAT GGCTGGTGAC  2400
```

```
GACATTCTTG TTGCACCCAT CCTCCACAGT CGCAAAGAAA TTCCAGGCGA AAACAGAGAT    2460

GTCTATCTCC CTCTTTACCA CACCTGGTAC CCCTCAAATT TGAGACCATG GGACGATCAA    2520

GGAGTCGCTT TGGGGAATCC TGTCGAAGGT GGTAGTGTCA TCAATTATAC TGCTAGGATT    2580

GTTGCACCCG AGGATTATAA TCTCTTCCAC AGCGTGGTAC CAGTCTACGT TAGAGAGGGT    2640

GCCATCATCC CGCAAATCGA AGTACGCCAA TGGACTGGCC AGGGGGGAGC CAACCGCATC    2700

AAGTTCAACA TCTACCCTGG AAAGGATAAG GAGTACTGTA CCTATCTTGA TGATGGTGTT    2760

AGCCGTGATA GTGCGCCGGA AGACCTCCCA CAGTACAAAG AGACCCACGA ACAGTCGAAG    2820

GTTGAAGGCG CGGAAATCGC AAAGCAGATT GGAAAGAAGA CGGGTTACAA CATCTCAGGA    2880

ACCGACCCAG AAGCAAAGGG TTATCACCGC AAAGTTGCTG TCACACAAAC GTCAAAAGAC    2940

AAGACGCGTA CTGTCACTAT TGAGCCAAAA CACAATGGAT ACGACCCTTC CAAAGAGGTG    3000

GGTGATTATT ATACCATCAT TCTTTGGTAC GCACCAGGTT TCGATGGCAG CATCGTCGAT    3060

GTGAGCAAGA CGACTGTGAA TGTTGAGGGT GGGGTGGAGC ACCAAGTTTA TAAGAACTCC    3120

GATTTACATA CGGTTGTTAT CGACGTGAAG GAGGTGATCG GTACCACAAA GAGCGTCAAG    3180

ATCACATGTA CTGCCGCTTA A                                               3201

(2) INFORMATION FOR SEQ ID NO: 8:

(i) SEQUENCE CHARACTERISTICS:
        (A) LENGTH: 3213 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 8:

ATGGCAGGAT TATCCGACCC TCTCAATTTC TGCAAAGCAG AGGACTACTA CGCTGCTGCC      60

AAAGGCTGGA GTGGCCCTCA GAAGATCATT CGCTATGACC AGACCCCTCC TCAGGGTACA    120

AAAGATCCGA AAAGCTGGCA TGCGGTAAAC CTTCCTTTCG ATGACGGGAC TATGTGTGTA    180

GTGCAATTCG TCAGACCCTG TGTTTGGAGG GTTAGATATG ACCCCAGTGT CAAGACTTCT    240

GATGAGTACG GCGATGAGAA TACGAGGACT ATTGTACAAG ACTACATGAC TACTCTGGTT    300

GGAAACTTGG ACATTTTCAG AGGTCTTACG TGGGTTTCTA CGTTGGAGGA TTCGGGCGAG    360

TACTACACCT TCAAGTCCGA AGTCACTGCC GTGGACGAAA CCGAACGGAC TCGAAACAAG    420

GTCGGCGACG GCCTCAAGAT TTACCTATGG AAAAATCCCT TTCGCATCCA GGTAGTGCGT    480

CTCTTGACCC CCCTGGTGGA CCCTTTCCCC ATTCCCAACG TAGCCAATGC CACAGCCCGT    540

GTGGCCGACA AGGTTGTTTG GCAGACGTCC CCGAAGACGT TCAGGAAAAA CTTGCATCCG    600

CAGCATAAGA TGTTGAAGGA TACAGTTCTT GATATTATCA AGCCGGGGCA CGGAGAGTAT    660

GTGGGTTGGG GAGAGATGGG AGGCATCGAG TTTATGAAGG AGCCAACATT CATGAATTAT    720

TTCAACTTTG ACAATATGCA ATATCAGCAG GTCTATGCAC AAGGCGCTCT TGATAGTCGT    780

GAGCCGTTGT ATCACTCTGA TCCCTTCTAT CTCGACGTGA ACTCCAACCC AGAGCACAAG    840

AACATTACGG CAACCTTTAT CGATAACTAC TCTCAGATTG CCATCGACTT TGGGAAGACC    900

AACTCAGGCT ACATCAAGCT GGGTACCAGG TATGGCGGTA TCGATTGTTA CGGTATCAGC    960

GCGGATACGG TCCCGGAGAT TGTGCGACTT TATACTGGAC TTGTTGGGCG TTCGAAGTTG   1020

AAGCCCAGGT ATATTCTCGG AGCCCACCAA GCTTGTTATG GATACCAGCA GGAAAGTGAC   1080

TTGCATGCTG TTGTTCAGCA GTACCGTGAC ACCAAGTTTC GCTTGATGGG GTTGCATGTC   1140
```

```
GATGTCGACT TTCAGGACAA TTTCAGAACG TTTACCACTA ACCCGATTAC GTTCCCTAAT    1200

CCCAAAGAAA TGTTTACCAA TCTAAGGAAC AATGGAATCA AGTGTTCCAC CAACATCACC    1260

CCTGTTATCA GTATCAGAGA TCGCCCGAAT GGGTACAGTA CCCTCAATGA GGGATATGAT    1320

AAAAAGTACT TCATCATGGA TGACAGATAT ACCGAGGGGA CAAGTGGGGA CCCGCAAAAT    1380

GTTCGATACT CTTTTTACGG CGGTGGGAAC CCGGTTGAGG TTAACCCTAA TGATGTTTGG    1440

GCTCGGCCAG ACTTTGGAGA CAATTATGAC TTCCCTACGA ACTTCAACTG CAAAGACTAC    1500

CCCTATCATG GTGGTGTGAG TTACGGATAT GGGAATGGCA CTCCAGGTTA CTACCCTGAC    1560

CTTAACAGAG AGGAGGTTCG TATCTGGTGG GGATTGCAGT ACGAGTATCT CTTCAATATG    1620

GGACTAGAGT TTGTATGGCA AGATATGACA ACCCCAGCGA TCCATTCATC ATATGGAGAC    1680

ATGAAAGGGT TGCCCACCCG TCTGCTCGTC ACCGCCGACT CAGTTACCAA TGCCTCTGAG    1740

AAAAAGCTCG CAATTGAAAG TTGGGCTCTT TACTCCTACA ACCTCCATAA AGCAACCTTC    1800

CACGGTCTTG GTCGTCTTGA GTCTCGTAAG AACAAACGTA ACTTCATCCT CGGACGTGGT    1860

AGTTACGCCG GTGCCTATCG TTTTGCTGGT CTCTGGACTG GAGATAACGC AAGTACGTGG    1920

GAATTCTGGA AGATTTCGGT CTCCCAAGTT CTTTCTCTAG GTCTCAATGG TGTGTGTATA    1980

GCGGGGTCTG ATACGGGTGG TTTTGAGCCC GCACGTACTG AGATTGGGGA GGAGAAATAT    2040

TGCAGTCCGG AGCTACTCAT CAGGTGGTAT ACTGGATCAT TCCTTTTGCC ATGGCTTAGA    2100

AACCACTACG TCAAGAAGGA CAGGAAATGG TTCCAGGAAC CATACGCGTA CCCCAAGCAT    2160

CTTGAAACCC ATCCAGAGCT CGCAGATCAA GCATGGCTTT ACAAATCTGT TCTAGAAATT    2220

TGCAGATACT GGGTAGAGCT AAGATATTCC CTCATCCAGC TCCTTTACGA CTGCATGTTC    2280

CAAAACGTGG TCGATGGTAT GCCACTTGCC AGATCTATGC TCTTGACCGA TACTGAGGAT    2340

ACGACCTTCT TCAATGAGAG CCAAAAGTTC CTCGATAACC AATATATGGC TGGTGACGAC    2400

ATCCTTGTAG CACCCATCCT CCACAGCCGT AACGAGGTTC CGGGAGAGAA CAGAGATGTC    2460

TATCTCCCTC TATTCCACAC CTGGTACCCC TCAAACTTGA GACCGTGGGA CGATCAGGGA    2520

GTCGCTTTAG GGAATCCTGT CGAAGGTGGC AGCGTTATCA ACTACACTGC CAGGATTGTT    2580

GCCCCAGAGG ATTATAATCT CTTCCACAAC GTGGTGCCGG TCTACATCAG AGAGGGTGCC    2640

ATCATTCCGC AAATTCAGGT ACGCCAGTGG ATTGGCGAAG GAGGGCCTAA TCCCATCAAG    2700

TTCAATATCT ACCCTGGAAA GGACAAGGAG TATGTGACGT ACCTTGATGA TGGTGTTAGC    2760

CGCGATAGTG CACCAGATGA CCTCCCGCAG TACCGCGAGG CCTATGAGCA AGCGAAGGTC    2820

GAAGGCAAAG ACGTCCAGAA GCAACTTGCG GTCATTCAAG GGAATAAGAC TAATGACTTC    2880

TCCGCCTCCG GGATTGATAA GGAGGCAAAG GGTTATCACC GCAAAGTTTC TATCAAACAG    2940

GAGTCAAAAG ACAAGACCCG TACTGTCACC ATTGAGCCAA AACACAACGG ATACGACCCC    3000

TCTAAGGAAG TTGGTAATTA TTATACCATC ATTCTTTGGT ACGCACCGGG CTTTGACGGC    3060

AGCATCGTCG ATGTGAGCCA GGCGACCGTG AACATCGAGG GCGGGGTGGA ATGCGAAATT    3120

TTCAAGAACA CCGGCTTGCA TACGGTTGTA GTCAACGTGA AAGAGGTGAT CGGTACCACA    3180

AAGTCCGTCA AGATCACTTG CACTACCGCT TAG                                  3213
```

(2) INFORMATION FOR SEQ ID NO: 9:

(i) SEQUENCE CHARACTERISTICS:
        (A) LENGTH: 317 amino acids
        (B) TYPE: amino acid
        (D) TOPOLOGY: linear (ii) MOLECULE TYPE: peptide (ix) FEATURE:
    (A) NAME/KEY: Modified-site
    (B) LOCATION: 201
    (D) OTHER INFORMATION: /note= "X denotes a misc. amino acid"

(xi) SEQUENCE DESCRIPTION: SEQ ID NO: 9:

```
Met Thr Asn Tyr Asn Tyr Asp Asn Leu Asn Tyr Asn Gln Pro Asp Leu
1               5                   10                  15
Ile Pro Pro Gly His Asp Ser Asp Pro Asp Tyr Ile Pro Met Tyr
            20                  25                  30
Phe Ala Ala Pro Trp Val Ile Ala His Gly Tyr Arg Gly Thr Ser Asp
            35                  40                  45
Gln Tyr Ser Tyr Gly Trp Phe Leu Asp Asn Val Ser Gln Ser Tyr Thr
50                      55                  60
Asn Thr Gly Asp Asp Ala Trp Ala Gly Gln Lys Asp Leu Ala Tyr Met
65                  70                  75                  80
Gly Ala Gln Cys Gly Pro Phe Asp Gln His Phe Val Tyr Glu Ala Gly
                85                  90                  95
Asp Gly Leu Glu Asp Val Val Thr Ala Phe Ser Tyr Leu Gln Gly Lys
                100                 105                 110
Glu Tyr Glu Asn Gln Gly Leu Asn Ile Arg Ser Ala Met Pro Pro Lys
            115                 120                 125
Tyr Val Phe Gly Phe Phe Gln Gly Val Phe Gly Ala Thr Ser Leu Leu
            130                 135                 140
Arg Asp Asn Leu Pro Ala Gly Glu Asn Asn Val Ser Leu Glu Glu Ile
145                 150                 155                 160
Val Glu Gly Tyr Gln Asn Gln Asn Val Pro Phe Glu Gly Leu Ala Val
                165                 170                 175
Asp Val Asp Met Gln Asp Asp Leu Arg Val Phe Thr Thr Arg Pro Ala
                180                 185                 190
Phe Trp Thr Ala Asn Lys Val Gly Xaa Gly Gly Asp Pro Asn Asn Lys
            195                 200                 205
Ser Val Phe Glu Trp Ala His Asp Arg Gly Leu Val Cys Gln Thr Asn
210                 215                 220
Val Thr Cys Phe Leu Lys Asn Glu Lys Asn Pro Tyr Glu Val Asn Gln
225                 230                 235                 240
Ser Leu Arg Glu Lys Gln Leu Tyr Thr Lys Ser Asp Ser Leu Asp Asn
                245                 250                 255
Ile Asp Phe Gly Thr Thr Pro Asp Gly Pro Ser Asp Ala Tyr Ile Gly
            260                 265                 270
His Leu Asp Tyr Gly Gly Gly Val Glu Cys Asp Ala Leu Phe Pro Asp
                275                 280                 285
Trp Gly Arg Pro Asp Val Ala Gln Trp Trp Gly Asp Asn Tyr Lys Lys
            290                 295                 300
Leu Phe Ser Ile Gly Leu Asp Phe Val Trp Gln Asp Met
305                 310                 315
```

(2) INFORMATION FOR SEQ ID NO: 10:

(i) SEQUENCE CHARACTERISTICS:
        (A) LENGTH: 323 amino acids
        (B) TYPE: amino acid
        (D) TOPOLOGY: linear (ii) MOLECULE TYPE: peptide

```
        (ix) FEATURE:
              (A) NAME/KEY: Modified-site
              (B) LOCATION: 272
              (D) OTHER INFORMATION: /note= "X is a misc. amino acid"

(ix) FEATURE:
              (A) NAME/KEY: Modified-site
              (B) LOCATION: 273
              (D) OTHER INFORMATION: /note= "X is a misc. amino acids"

(ix) FEATURE:
              (A) NAME/KEY: Modified-site
              (B) LOCATION: 274
              (D) OTHER INFORMATION: /note= "X is a misc. amino acid"

(xi) SEQUENCE DESCRIPTION: SEQ ID NO: 10:

Met Thr Asn Tyr Asn Tyr Asp Asn Tyr Asn Tyr Asn Gln Ser Asp Leu
 1               5                  10                  15

Ile Ala Pro Gly Tyr Pro Ser Asp Pro Asn Phe Tyr Ile Pro Met Tyr
                20                  25                  30

Phe Ala Ala Pro Trp Val Val Val Lys Gly Cys Ser Gly Asn Ser Asp
            35                  40                  45

Glu Gln Tyr Ser Tyr Gly Trp Phe Met Asp Asn Val Ser Gln Thr Tyr
        50                  55                  60

Met Asn Thr Gly Gly Thr Ser Trp Asn Cys Gly Glu Glu Asn Leu Ala
65                  70                  75                  80

Tyr Met Gly Ala Gln Cys Gly Pro Phe Asp Gln His Phe Val Tyr Gly
                85                  90                  95

Asp Gly Asp Gly Leu Glu Asp Val Val Gln Ala Phe Ser Leu Leu Gln
                100                 105                 110

Gly Lys Glu Phe Glu Asn Gln Val Leu Asn Lys Arg Ala Val Met Pro
            115                 120                 125

Pro Lys Tyr Val Phe Gly Tyr Phe Gln Gly Val Phe Gly Ile Ala Ser
        130                 135                 140

Leu Leu Arg Glu Gln Arg Pro Glu Gly Gly Asn Asn Ile Ser Val Ser
145                 150                 155                 160

Glu Ile Val Glu Gly Tyr Gln Ser Asn Asn Phe Pro Leu Glu Gly Leu
                165                 170                 175

Ala Val Asp Val Asp Met Gln Gln Asp Leu Arg Cys Ser Ser Pro Leu
                180                 185                 190

Lys Ile Glu Phe Trp Thr Ala Asn Lys Val Gly Thr Gly Asp Ser
            195                 200                 205

Asn Asn Lys Ser Val Phe Glu Trp Ala His Asp Lys Gly Leu Val Cys
        210                 215                 220

Gln Thr Asn Val Thr Cys Phe Leu Arg Asn Asp Asn Gly Gly Ala Asp
225                 230                 235                 240

Tyr Glu Val Asn Gln Thr Leu Arg Glu Lys Gly Leu Tyr Thr Lys Asn
                245                 250                 255

Asp Ser Leu Thr Asn Thr Asn Phe Gly Thr Thr Asn Asp Gly Pro Xaa
                260                 265                 270

Xaa Xaa Tyr Ile Gly His Leu Asp Tyr Gly Gly Gly Asn Cys Asp
            275                 280                 285

Ala Leu Phe Pro Asp Trp Gly Arg Pro Gly Val Ala Glu Trp Trp Gly
290                 295                 300

Asp Asn Tyr Ser Lys Leu Phe Lys Ile Gly Leu Asp Phe Val Trp Gln
305                 310                 315                 320

Asp Met Thr
```

(2) INFORMATION FOR SEQ ID NO: 11:

(i) SEQUENCE CHARACTERISTICS:
        (A) LENGTH: 202 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 43
        (D) OTHER INFORMATION: /note= "X is a misc. amino acid"

(ix) FEATURE:
        (A) NAME/KEY: Modified-site
        (B) LOCATION: 176
        (D) OTHER INFORMATION: /note= "X is a misc. amino acid"

(xi) SEQUENCE DESCRIPTION: SEQ ID NO: 11:

```
Met Thr Asn Tyr Asn Tyr Asp Asn Leu Asn Tyr Asn Gln Pro Asp Val
1               5                   10                  15

Val Pro Pro Gly Tyr His Asp His Pro Asn Tyr Tyr Ile Pro Met Tyr
            20                  25                  30

Tyr Ala Ala Pro Trp Leu Val Val Gln Gly Xaa Ala Gly Thr Ser Lys
        35                  40                  45

Gln Tyr Ser Tyr Gly Trp Phe Met Asp Asn Val Ser Gln Ser Tyr Met
    50                  55                  60

Asn Thr Gly Asp Thr Ala Trp Asn Cys Gly Gln Glu Asn Leu Ala Tyr
65                  70                  75                  80

Met Gly Ala Gln Tyr Gly Pro Phe Asp Gln His Phe Val Tyr Gly Asp
                85                  90                  95

Gly Asp Gly Leu Glu Asp Val Val Lys Ala Phe Ser Phe Leu Gln Gly
                100                 105                 110

Lys Glu Phe Glu Asp Lys Lys Leu Asn Lys Arg Ser Val Met Pro Pro
            115                 120                 125

Lys Tyr Val Phe Gly Phe Phe Gln Gly Val Phe Gly Ala Leu Ser Leu
    130                 135                 140

Leu Lys Gln Asn Leu Pro Ala Gly Glu Asn Asn Ile Ser Val Gln Glu
145                 150                 155                 160

Ile Val Glu Gly Tyr Gln Asp Asn Asp Tyr Pro Phe Glu Gly Leu Xaa
                165                 170                 175

Val Asp Val Asp Met Gln Asp Asp Leu Arg Val Phe Thr Thr Lys Pro
                180                 185                 190

Glu Tyr Trp Ser Ala Asn Met Val Gly Glu
            195                 200
```

(2) INFORMATION FOR SEQ ID NO: 12:

(i) SEQUENCE CHARACTERISTICS:
        (A) LENGTH: 953 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_difference
        (B) LOCATION: replace(573, "")
        (D) OTHER INFORMATION: /note= "g is a misc nucleic acid"

(ix) FEATURE:

(A) NAME/KEY: misc_difference
        (B) LOCATION: replace(601, "")
        (D) OTHER INFORMATION: /note= "g is a misc. nucleic acid"

(xi) SEQUENCE DESCRIPTION: SEQ ID NO: 12:

```
ATGACAAACT ATAATTATGA CAATTTGAAC TACAATCAAC CGGACCTCAT CCCACCTGGC      60

CATGATTCAG ATCCTGACTA CTATATTCCG ATGTACTTTG CGGCACCATG GGTGATCGCA     120

CATGGATATC GTGGCACCAG CGACCAGTAC TCTTATGGAT GGTTTTTGGA CAATGTATCC     180

CAGTCCTACA CAAACACTGG CGATGATGCA TGGGCTGGTC AGAAGGATTT GGCGTACATG     240

GGGGCACAAT GTGGGCCTTT CGATCAACAT TTTGTGTATG AGGCTGGAGA TGGACTTGAA     300

GACGTTGTGA CCGCATTCTC TTATTTGCAA GGCAAGGAAT ATGAGAACCA GGGACTGAAT     360

ATACGTTCTG CAATGCCTCC GAAGTACGTT TTCGGATTTT TCCAAGGCGT ATTCGGAGCC     420

ACATCGCTGC TAAGGGACAA CTTACCTGCC GGCGAGAACA ACGTCTCTTT GGAAGAAATT     480

GTTGAAGGAT ATCAAAATCA GAACGTGCCA TTTGAAGGTC TTGCTGTGGA TGTTGATATG     540

CAAGATGACT TGAGAGTGTT CACTACGAGA CCGGCGTTTT GGACGGCAAA CAAGGTGGGG     600

GAAGGCGGTG ATCCAAACAA CAAGTCAGTG TTTGAGTGGG CACATGACAG GGGCCTTGTC     660

TGCCAGACGA ATGTAACTTG CTTCTTGAAG AACGAGAAAA ATCCTTACGA AGTGAATCAG     720

TCATTGAGGG AGAAGCAGTT GTATACGAAG AGTGATTCCT TGGACAACAT TGATTTTGGA     780

ACTACTCCAG ATGGGCCTAG CGATGCGTAC ATTGGACACT TAGACTACGG TGGTGGTGTG     840

GAGTGTGATG CACTATTCCC AGACTGGGGT CGACCAGACG TGGCTCAATG GTGGGCGAT      900

AACTACAAGA AACTATTCAG CATTGGTCTC GACTTCGTAT GGCAAGACAT GAC           953
```

(2) INFORMATION FOR SEQ ID NO: 13:

(i) SEQUENCE CHARACTERISTICS:
        (A) LENGTH: 969 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_difference
        (B) LOCATION: replace(814..821, "")
        (D) OTHER INFORMATION: /note= "Each g between (and
            including) 814 and 821 is a misc. nucleic acid."

(xi) SEQUENCE DESCRIPTION: SEQ ID NO: 13:

```
ATGACAAACT ACAACTACGA CAACTATAAC TACAACCAGT CAGATCTTAT TGCTCCAGGA      60

TATCCTTCCG ACCCGAACTT CTACATTCCC ATGTATTTTG CAGCACCTTG GGTAGTTGTT     120

AAGGGATGCA GTGGCAACAG CGATGAACAG TACTCGTACG GATGGTTTAT GGATAATGTC     180

TCCCAAACTT ACATGAATAC TGGTGGTACT TCCTGGAACT GTGGAGAGGA GAACTTGGCA     240

TACATGGGAG CACAGTGCGG TCCATTTGAC CAACATTTTG TGTATGGTGA TGGAGATGGT     300

CTTGAGGATG TTGTCCAAGC GTTCTCTCTT CTGCAAGGCA AGAGTTTGA GAACCAAGTT      360

CTGAACAAAC GTGCCGTAAT GCCTCCGAAA TATGTGTTTG GTTACTTTCA GGGAGTCTTT     420

GGGATTGCTT CCTTGTTGAG AGAGCAAAGA CCAGAGGGTG GTAATAACAT CTCTGTTTCA     480

GAGATTGTCG AAGGTTACCA AAGCAATAAC TTCCCTTTAG AGGGGTTAGC CGTAGATGTG     540

GATATGCAAC AAGATTGCG GTGTAGTTCA CCACTGAAGA TTGAATTTTG GACGGCAAAT      600

AAGGTAGGCA CCGGGGGAGA CTCGAATAAC AAGTCGGTGT TTGAATGGGC ACATGACAAA     660
```

```
GGCCTTGTAT GTCAGACGAA TGTTACTTGC TTCTTGAGAA ACGACAACGG CGGGGCAGAT      720

TACGAAGTCA ATCAGACATT GAGGGAGAAG GGTTTGTACA CGAAGAATGA CTCACTGACG      780

AACACTAACT TCGGAACTAC CAACGACGGG CCGGGGGGGG GGTACATTGG ACATCTGGAC      840

TATGGTGGCG GAGGGAATTG TGATGCACTT TTCCCAGATT GGGGTCGACC GGGTGTGGCT      900

GAATGGTGGG GTGATAACTA CAGCAAGCTC TTCAAAATTG GTCTGGACTT CGTGTGGCAA      960

GATATGACA                                                             969
```

(2) INFORMATION FOR SEQ ID NO: 14:

(i) SEQUENCE CHARACTERISTICS:
        (A) LENGTH: 607 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_difference
        (B) LOCATION: replace(128, "")
        (D) OTHER INFORMATION: /note= "g is a misc. nucleic acid"

(ix) FEATURE:
        (A) NAME/KEY: misc_difference
        (B) LOCATION: replace(232, "")
        (D) OTHER INFORMATION: /note= "g is a misc. nucleic acid"

(ix) FEATURE:
        (A) NAME/KEY: misc_difference
        (B) LOCATION: replace(249, "")
        (D) OTHER INFORMATION: /note= "g is a misc. nucleic acid"

(ix) FEATURE:
        (A) NAME/KEY: misc_difference
        (B) LOCATION: replace(526, "")
        (D) OTHER INFORMATION: /note= "g is a misc. nucleic acid"

(xi) SEQUENCE DESCRIPTION: SEQ ID NO: 14:

```
ATGACAAACT ACAATTACGA CAACTTGAAC TACAACCAAC CAGACGTCGT TCCTCCAGGT       60

TATCACGACC ATCCCAACTA CTACATTCCA ATGTACTACG CAGCACCGTG GTTGGTCGTT      120

CAGGGATGCG CGGGGACATC GAAGCAATAC TCGTACGGTT GGTTTATGGA CAATGTCTCT      180

CAGTCGTACA TGAACACTGG AGATACGGCG TGGAACTGCG GACAGGAAAA CGTGGCATAC      240

ATGGGCGCGC AATACGGGCC ATTTGATCAG CACTTTGTGT ATGGTGATGG AGATGGCCTT      300

GAAGATGTCG TCAAAGCGTT CTCCTTTCTT CAAGGAAAGG AGTTCGAAGA CAAAAAACTC      360

AACAAGCGTT CTGTAATGCC TCCGAAGTAC GTGTTTGGTT TCTTCCAGGG TGTTTTCGGT      420

GCACTTTCAC TGTTGAAGCA GAATCTGCCT GCCGGAGAGA ACAACATCTC AGTGCAAGAG      480

ATTGTGGAGG GTTACCAGGA TAACGACTAC CCCTTTGAAG GGCTCGCGGT AGATGTTGAT      540

ATGCAAGATG ATCTGCGAGT GTTTACTACC AAACCAGAAT ATTGGTCGGC AAACATGGTA      600

GGCGAAG                                                               607
```

(2) INFORMATION FOR SEQ ID NO: 15:

(i) SEQUENCE CHARACTERISTICS:
        (A) LENGTH: 90 amino acids
        (B) TYPE: amino acid
        (D) TOPOLOGY: linear (ii) MOLECULE TYPE: peptide (xi) SEQUENCE DESCRIPTION: SEQ ID NO: 15:

```
Tyr Arg Trp Gln Glu Val Leu Tyr Thr Ala Met Tyr Gln Asn Ala Ala
1               5                   10                  15

Phe Gly Lys Pro Ile Ile Lys Ala Ala Ser Met Tyr Asn Asn Asp Ser
            20                  25                  30

Asn Val Arg Arg Ala Gln Asn Asp His Phe Leu Leu Gly Gly His Asp
        35                  40                  45

Gly Tyr Arg Ile Leu Cys Ala Pro Val Val Trp Glu Asn Ser Thr Glu
    50                  55                  60

Arg Glu Leu Tyr Leu Pro Val Leu Thr Gln Trp Tyr Lys Phe Gly Pro
65                  70                  75                  80

Asp Phe Asp Thr Lys Pro Leu Glu Gly Ala
                85                  90
```

(2) INFORMATION FOR SEQ ID NO: 16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_difference
        (B) LOCATION: replace(6, "")
        (D) OTHER INFORMATION: /note= "N is T OR C"

(ix) FEATURE:
        (A) NAME/KEY: misc_difference
        (B) LOCATION: replace(9, "")
        (D) OTHER INFORMATION: /note= "N IS C OR T"

(ix) FEATURE:
        (A) NAME/KEY: misc_difference
        (B) LOCATION: replace(12, "")
        (D) OTHER INFORMATION: /note= "N IS C OR T"

(ix) FEATURE:
        (A) NAME/KEY: misc_difference
        (B) LOCATION: replace(15, "")
        (D) OTHER INFORMATION: /note= "N IS C OR T"

(ix) FEATURE:
        (A) NAME/KEY: misc_difference
        (B) LOCATION: replace(18, "")
        (D) OTHER INFORMATION: /note= "N IS G OR A OR T OR C"

(ix) FEATURE:
        (A) NAME/KEY: misc_difference
        (B) LOCATION: replace(21, "")
        (D) OTHER INFORMATION: /note= "N IS C OR T"

(xi) SEQUENCE DESCRIPTION: SEQ ID NO: 16:

ATGTANAAANA ANGANTCNAA NGT                                  23

(2) INFORMATION FOR SEQ ID NO: 17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_difference
        (B) LOCATION: replace(6, "")
        (D) OTHER INFORMATION: /note= "N IS T OR C"

```
    (ix) FEATURE:
         (A) NAME/KEY: misc_difference
         (B) LOCATION: replace(9, "")
         (D) OTHER INFORMATION: /note= "N IS C OR T"

(ix) FEATURE:
         (A) NAME/KEY: misc_difference
         (B) LOCATION: replace(12, "")
         (D) OTHER INFORMATION: /note= "N IS C OR T"

(ix) FEATURE:
         (A) NAME/KEY: misc_difference
         (B) LOCATION: replace(15, "")
         (D) OTHER INFORMATION: /note= "N IS C OR T"

(ix) FEATURE:
         (A) NAME/KEY: misc_difference
         (B) LOCATION: replace(18, "")
         (D) OTHER INFORMATION: /note= "N IS C OR T"

(ix) FEATURE:
         (A) NAME/KEY: misc_difference
         (B) LOCATION: replace(21, "")
         (D) OTHER INFORMATION: /note= "N IS C OR T"

(xi) SEQUENCE DESCRIPTION: SEQ ID NO: 17:

ATGTANAAANA ANGANAGNAA NGT                                           23

(2) INFORMATION FOR SEQ ID NO: 18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: misc_difference
         (B) LOCATION: replace(3, "")
         (D) OTHER INFORMATION: /note= "N IS G OR A OR T OR C"

(ix) FEATURE:
         (A) NAME/KEY: misc_difference
         (B) LOCATION: replace(6, "")
         (D) OTHER INFORMATION: /note= "N IS G OR A"

(ix) FEATURE:
         (A) NAME/KEY: misc_difference
         (B) LOCATION: replace(9, "")
         (D) OTHER INFORMATION: /note= "N IS G OR A"

(ix) FEATURE:
         (A) NAME/KEY: misc_difference
         (B) LOCATION: replace(12, "")
         (D) OTHER INFORMATION: /note= "N IS G OR A OR T OR C"

(ix) FEATURE:
         (A) NAME/KEY: misc_difference
         (B) LOCATION: replace(15, "")
         (D) OTHER INFORMATION: /note= "N IS G OR A OR T OR C"

(xi) SEQUENCE DESCRIPTION: SEQ ID NO: 18:

TANCCNTCNT GNCCNCC                                                   17

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)
```

```
       (ix) FEATURE:
             (A) NAME/KEY: misc_difference
             (B) LOCATION: replace(3, "")
             (D) OTHER INFORMATION: /note= "N IS G OR A OR T OR C"

(ix) FEATURE:
             (A) NAME/KEY: misc_difference
             (B) LOCATION: replace(6, "")
             (D) OTHER INFORMATION: /note= "N IS G OR A"

(ix) FEATURE:
             (A) NAME/KEY: misc_difference
             (B) LOCATION: replace(9, "")
             (D) OTHER INFORMATION: /note= "N IS C OR T"

(ix) FEATURE:
             (A) NAME/KEY: misc_difference
             (B) LOCATION: replace(12, "")
             (D) OTHER INFORMATION: /note= "N IS G OR A"

(ix) FEATURE:
             (A) NAME/KEY: misc_difference
             (B) LOCATION: replace(18, "")
             (D) OTHER INFORMATION: /note= "N IS C OR T"

(xi) SEQUENCE DESCRIPTION: SEQ ID NO: 19:

GGNCCNAANT TNTACCANTG                                                        20

(2) INFORMATION FOR SEQ ID NO: 20:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: misc_difference
             (B) LOCATION: replace(3, "")
             (D) OTHER INFORMATION: /note= "N IS T OR C"

(ix) FEATURE:
             (A) NAME/KEY: misc_difference
             (B) LOCATION: replace(6, "")
             (D) OTHER INFORMATION: /note= "N IS G OR A OR T OR C"

(ix) FEATURE:
             (A) NAME/KEY: misc_difference
             (B) LOCATION: replace(12, "")
             (D) OTHER INFORMATION: /note= "N IS G OR A"

(ix) FEATURE:
             (A) NAME/KEY: misc_difference
             (B) LOCATION: replace(15, "")
             (D) OTHER INFORMATION: /note= "N IS G OR A"

(xi) SEQUENCE DESCRIPTION: SEQ ID NO: 20:

TANCGNTGGC ANGANGT                                                           17

(2) INFORMATION FOR SEQ ID NO: 21:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: misc_difference
             (B) LOCATION: replace(3, "")
```

(D) OTHER INFORMATION: /note= "N IS T OR C"

(ix) FEATURE:
            (A) NAME/KEY: misc_difference
            (B) LOCATION: replace(6, "")
            (D) OTHER INFORMATION: /note= "N IS G OR A"

(ix) FEATURE:
            (A) NAME/KEY: misc_difference
            (B) LOCATION: replace(12, "")
            (D) OTHER INFORMATION: /note= "N IS G OR A"

(ix) FEATURE:
            (A) NAME/KEY: misc_difference
            (B) LOCATION: replace(15, "")
            (D) OTHER INFORMATION: /note= "N IS G OR A"

(xi) SEQUENCE DESCRIPTION: SEQ ID NO: 21:

TANAGNTGGC ANGANGT                                                              17

(2) INFORMATION FOR SEQ ID NO: 22:

(i) SEQUENCE CHARACTERISTICS:
            (A) LENGTH: 71 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO: 22:

ATGTACAACA ACGACTCGAA CGTTCGCAGG GCGCAGAACG ATCATTTCCT TCTTGGCGGC               60

CACGACGGTT A                                                                    71

(2) INFORMATION FOR SEQ ID NO: 23:

(i) SEQUENCE CHARACTERISTICS:
            (A) LENGTH: 23 amino acids
            (B) TYPE: amino acid
            (D) TOPOLOGY: linear (ii) MOLECULE TYPE: peptide (xi) SEQUENCE DESCRIPTION: SEQ ID NO: 23:

Met Tyr Asn Asn Asp Ser Asn Val Arg Arg Ala Gln Asn Asp His Phe
1               5                   10                  15

Leu Leu Gly Gly His Asp Gly
            20

(2) INFORMATION FOR SEQ ID NO: 24:

(i) SEQUENCE CHARACTERISTICS:
            (A) LENGTH: 160 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO: 24:

ATGTACAACA ACGACTCGAA CGTTCGCAGG GCGCAGAACG ATCATTTCCT TCTTGGTGGA               60

CATGATGGAT ATCGCATTCT GTGCGCGCCT GTTGTGTGGG AGAATTCGAC CGAACGGAAT              120

TGTACTTGCC CGTGCTGACC CAATGGTACA AATTCGGCCC                                    160

(2) INFORMATION FOR SEQ ID NO: 25:

(i) SEQUENCE CHARACTERISTICS:

(A) LENGTH: 54 amino acids
        (B) TYPE: amino acid
        (D) TOPOLOGY: linear (ii) MOLECULE TYPE: peptide (xi) SEQUENCE DESCRIPTION: SEQ ID NO: 25:

Met Tyr Asn Asn Asp Ser Asn Val Arg Arg Ala Gln Asn Asp His Phe
1               5                   10                  15

Leu Leu Gly Gly His Asp Gly Tyr Arg Ile Leu Cys Ala Pro Val Val
            20                  25                  30

Trp Glu Asn Ser Thr Glu Arg Glu Leu Tyr Leu Pro Val Leu Thr Gln
            35                  40                  45

Trp Tyr Lys Phe Gly Pro
            50

(2) INFORMATION FOR SEQ ID NO: 26:

(i) SEQUENCE CHARACTERISTICS:
        (A) LENGTH: 238 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 26:

TACAGGTGGC AGGAGGTGTT GTACACTGCT ATGTACCAGA ATGCGGCTTT CGGGAAACCG      60

ATTATCAAGG CAGCTTCCAT GTACGACAAC GACAGAAACG TTCGCGGCGC ACAGGATGAC     120

CACTTCCTTC TCGGCGGACA CGATGGATAT CGTATTTTGT GTGCACCTGT TGTGTGGGAG     180

AATACAACCA GTCGCGATCT GTACTTGCCT GTGCTGACCA GTGGTACAAA TTCGGCCC      238

(2) INFORMATION FOR SEQ ID NO: 27:

(i) SEQUENCE CHARACTERISTICS:
        (A) LENGTH: 79 amino acids
        (B) TYPE: amino acid
        (D) TOPOLOGY: linear (ii) MOLECULE TYPE: peptide (xi) SEQUENCE DESCRIPTION: SEQ ID NO: 27:

Tyr Arg Trp Gln Glu Val Leu Tyr Thr Ala Met Tyr Gln Asn Ala Ala
1               5                   10                  15

Phe Gly Lys Pro Ile Ile Lys Ala Ala Ser Met Tyr Asp Asn Asp Arg
            20                  25                  30

Asn Val Arg Gly Ala Gln Asp Asp His Phe Leu Leu Gly Gly His Asp
            35                  40                  45

Gly Tyr Arg Ile Leu Cys Ala Pro Val Val Trp Glu Asn Thr Thr Ser
            50                  55                  60

Arg Asp Leu Tyr Leu Pro Val Leu Thr Lys Trp Tyr Lys Phe Gly
65                  70                  75

(2) INFORMATION FOR SEQ ID NO: 28:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

GCTCTAGAGC ATGTTTTCAA CCCTTGCG                28

(2) INFORMATION FOR SEQ ID NO: 29:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 29:

AGCTTGTTAA CATGTATCCA ACCCTCACCT TCGTGG        36

(2) INFORMATION FOR SEQ ID NO: 30:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 30:

ACAATTGTAC ATAGGTTGGG AGTGGAAGCA CCGC           34

(2) INFORMATION FOR SEQ ID NO: 31:

(i) SEQUENCE CHARACTERISTICS:
        (A) LENGTH: 75 amino acids
        (B) TYPE: amino acid
        (D) TOPOLOGY: linear (ii) MOLECULE TYPE: peptide (xi) SEQUENCE DESCRIPTION: SEQ ID NO: 31:

Lys Asn Leu His Pro Gln His Lys Met Leu Lys Asp Thr Val Leu Asp
1               5                   10                  15

Ile Val Lys Pro Gly His Gly Glu Tyr Val Gly Trp Gly Glu Met Gly
            20                  25                  30

Gly Ile Gln Phe Met Lys Glu Pro Thr Phe Met Asn Tyr Phe Asn Phe
        35                  40                  45

Asp Asn Met Gln Tyr Gln Val Tyr Ala Gln Gly Ala Leu Asp Ser
    50                  55                  60

Arg Glu Pro Leu Tyr His Ser Asp Pro Phe Tyr
65                  70                  75

(2) INFORMATION FOR SEQ ID NO: 32:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_difference
        (B) LOCATION: replace(3, "")
        (D) OTHER INFORMATION: /note= "N IS G OR A"

(ix) FEATURE:
        (A) NAME/KEY: misc_difference

```
        (B) LOCATION: replace(6, "")
        (D) OTHER INFORMATION: /note= "N IS C OR T"

(ix) FEATURE:
        (A) NAME/KEY: misc_difference
        (B) LOCATION: replace(9, "")
        (D) OTHER INFORMATION: /note= "N IS G OR A"

(ix) FEATURE:
        (A) NAME/KEY: misc_difference
        (B) LOCATION: replace(15, "")
        (D) OTHER INFORMATION: /note= "N IS G OR A OT T OR C"

(ix) FEATURE:
        (A) NAME/KEY: misc_difference
        (B) LOCATION: replace(18, "")
        (D) OTHER INFORMATION: /note= "N IS G OR A"

(ix) FEATURE:
        (A) NAME/KEY: misc_difference
        (B) LOCATION: replace(21, "")
        (D) OTHER INFORMATION: /note= "N IS C OR T"

(xi) SEQUENCE DESCRIPTION: SEQ ID NO: 32:

CANCANAAANA TGCTNAANGA NAC                                               23

(2) INFORMATION FOR SEQ ID NO: 33:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_difference
        (B) LOCATION: replace(3, "")
        (D) OTHER INFORMATION: /note= "N IS G OR A"

(ix) FEATURE:
        (A) NAME/KEY: misc_difference
        (B) LOCATION: replace(6, "")
        (D) OTHER INFORMATION: /note= "N IS C OR T"

(ix) FEATURE:
        (A) NAME/KEY: misc_difference
        (B) LOCATION: replace(9, "")
        (D) OTHER INFORMATION: /note= "N IS G OR A"

(ix) FEATURE:
        (A) NAME/KEY: misc_difference
        (B) LOCATION: replace(15, "")
        (D) OTHER INFORMATION: /note= "N IS G OR A"

(ix) FEATURE:
        (A) NAME/KEY: misc_difference
        (B) LOCATION: replace(18, "")
        (D) OTHER INFORMATION: /note= "N IS G OR A"

(ix) FEATURE:
        (A) NAME/KEY: misc_difference
        (B) LOCATION: replace(21, "")
        (D) OTHER INFORMATION: /note= "N IS C OR T"

(xi) SEQUENCE DESCRIPTION: SEQ ID NO: 33:

CANCANAAANA TGTTNAANGA NAC                                               23

(2) INFORMATION FOR SEQ ID NO: 34:

(i) SEQUENCE CHARACTERISTICS:
        (A) LENGTH: 20 base pairs
        (B) TYPE: nucleic acid
        (C) STRANDEDNESS: single
```

(D) TOPOLOGY: linear (ii) MOLECULE TYPE: cDNA (ix) FEATURE:
        (A) NAME/KEY: misc_difference
        (B) LOCATION: replace(3, "")
        (D) OTHER INFORMATION: /note= "N IS G OR A"

(ix) FEATURE:
        (A) NAME/KEY: misc_difference
        (B) LOCATION: replace(6, "")
        (D) OTHER INFORMATION: /note= "N IS G OR A OR T OR C"

(ix) FEATURE:
        (A) NAME/KEY: misc_difference
        (B) LOCATION: replace(9, "")
        (D) OTHER INFORMATION: /note= "N IS G OR A"

(ix) FEATURE:
        (A) NAME/KEY: misc_difference
        (B) LOCATION: replace(12, "")
        (D) OTHER INFORMATION: /note= "N IS G OR A"

(ix) FEATURE:
        (A) NAME/KEY: misc_difference
        (B) LOCATION: replace(15, "")
        (D) OTHER INFORMATION: /note= "N IS G OR A"

(ix) FEATURE:
        (A) NAME/KEY: misc_difference
        (B) LOCATION: replace(18, "")
        (D) OTHER INFORMATION: /note= "N IS G OR A"

(xi) SEQUENCE DESCRIPTION: SEQ ID NO: 34:

TANAANGGNT CNCTNTGNTA                                                           20

(2) INFORMATION FOR SEQ ID NO: 35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_difference
        (B) LOCATION: replace(3, "")
        (D) OTHER INFORMATION: /note= "N IS G OR A"

(ix) FEATURE:
        (A) NAME/KEY: misc_difference
        (B) LOCATION: replace(6, "")
        (D) OTHER INFORMATION: /note= "N IS G OR A OR T OR C"

(ix) FEATURE:
        (A) NAME/KEY: misc_difference
        (B) LOCATION: replace(9, "")
        (D) OTHER INFORMATION: /note= "N IS G OR A"

(ix) FEATURE:
        (A) NAME/KEY: misc_difference
        (B) LOCATION: replace(12, "")
        (D) OTHER INFORMATION: /note= "N IS G OR A OR T OR C"

(ix) FEATURE:
        (A) NAME/KEY: misc_difference
        (B) LOCATION: replace(15, "")
        (D) OTHER INFORMATION: /note= "N IS G OR A"

(ix) FEATURE:
        (A) NAME/KEY: misc_difference
        (B) LOCATION: replace(18, "")
        (D) OTHER INFORMATION: /note= "N IS G OR A"

(xi) SEQUENCE DESCRIPTION: SEQ ID NO: 35:

TANAANGGNT CNGANTGNTA                                                  20

(2) INFORMATION FOR SEQ ID NO: 36:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 36:

AAACTGCAGC TGGCGCGCCA TGGCAGGATT TTCTGAT                                37

(2) INFORMATION FOR SEQ ID NO: 37:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_difference
        (B) LOCATION: replace(6, "")
        (D) OTHER INFORMATION: /note= "N IS G OR A OR T OR C"

(ix) FEATURE:
        (A) NAME/KEY: misc_difference
        (B) LOCATION: replace(9, "")
        (D) OTHER INFORMATION: /note= "N IS C OR T"

(ix) FEATURE:
        (A) NAME/KEY: misc_difference
        (B) LOCATION: replace(12, "")
        (D) OTHER INFORMATION: /note= "N IS C OR T"

(ix) FEATURE:
        (A) NAME/KEY: misc_difference
        (B) LOCATION: replace(15, "")
        (D) OTHER INFORMATION: /note= "N IS C OR T"

(ix) FEATURE:
        (A) NAME/KEY: misc_difference
        (B) LOCATION: replace(18, "")
        (D) OTHER INFORMATION: /note= "N IS C OR T"

(ix) FEATURE:
        (A) NAME/KEY: misc_difference
        (B) LOCATION: replace(21, "")
        (D) OTHER INFORMATION: /note= "N IS C OR T"

(xi) SEQUENCE DESCRIPTION: SEQ ID NO: 37:

ATGACNAANT ANAANTANGA NAA                                              23

(2) INFORMATION FOR SEQ ID NO: 38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_difference
        (B) LOCATION: replace(1, "")
        (D) OTHER INFORMATION: /note= "N IS A OR G"

(ix) FEATURE:
        (A) NAME/KEY: misc_difference
        (B) LOCATION: replace(4, "")
        (D) OTHER INFORMATION: /note= "N IS G OR A OR T OR C"

(ix) FEATURE:
        (A) NAME/KEY: misc_difference
        (B) LOCATION: replace(13, "")
        (D) OTHER INFORMATION: /note= "N IS G OR A OR T OR C"

(ix) FEATURE:
        (A) NAME/KEY: misc_difference
        (B) LOCATION: replace(16, "")
        (D) OTHER INFORMATION: /note= "N IS G OR A OR T OR C"

(ix) FEATURE:
        (A) NAME/KEY: misc_difference
        (B) LOCATION: replace(19, "")
        (D) OTHER INFORMATION: /note= "N IS G OR A OR T OR C"

(xi) SEQUENCE DESCRIPTION: SEQ ID NO: 38:

NTGNGGCATC ATNGCNGGNA C                                                         21

(2) INFORMATION FOR SEQ ID NO: 39:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_difference
        (B) LOCATION: replace(6, "")
        (D) OTHER INFORMATION: /note= "N IS G OR A"

(ix) FEATURE:
        (A) NAME/KEY: misc_difference
        (B) LOCATION: replace(9, "")
        (D) OTHER INFORMATION: /note= "N IS C OR T"

(ix) FEATURE:
        (A) NAME/KEY: misc_difference
        (B) LOCATION: replace(15, "")
        (D) OTHER INFORMATION: /note= "N IS G OR A OR T OR C"

(ix) FEATURE:
        (A) NAME/KEY: misc_difference
        (B) LOCATION: replace(18, "")
        (D) OTHER INFORMATION: /note= "N IS G OR A"

(ix) FEATURE:
        (A) NAME/KEY: misc_difference
        (B) LOCATION: replace(21, "")
        (D) OTHER INFORMATION: /note= "N IS G OR A"

(xi) SEQUENCE DESCRIPTION: SEQ ID NO: 39:

GTCATNTCNT GCCANACNAA NTC                                                       23